(12) United States Patent
Das Neves Ferreira Da Silva et al.

(10) Patent No.: US 11,834,684 B2
(45) Date of Patent: Dec. 5, 2023

(54) VACCINE FOR IMMUNOCOMPROMISED HOSTS

(71) Applicant: Universidade do Porto—Reitoria, Oporto (PT)

(72) Inventors: Paula Maria Das Neves Ferreira Da Silva, Oporto (PT); Pedro Jorge Fonseca Madureira, Oporto (PT)

(73) Assignee: Universidade do Porto—Reitoria, Oporto (PT)

( * ) Notice: Subject to any disclaimer, the term of this patent is extended or adjusted under 35 U.S.C. 154(b) by 0 days.

(21) Appl. No.: 17/331,536

(22) Filed: May 26, 2021

(65) Prior Publication Data

US 2022/0049229 A1    Feb. 17, 2022

Related U.S. Application Data

(63) Continuation of application No. 15/313,327, filed as application No. PCT/EP2015/063243 on Jun. 12, 2015, now Pat. No. 11,066,652.

(30) Foreign Application Priority Data

Jun. 12, 2014 (EP) .................................... 14398006
Mar. 30, 2015 (EP) .................................... 15398003

(51) Int. Cl.
  *C12N 9/02* (2006.01)
  *A01K 67/027* (2006.01)
  *A61K 39/108* (2006.01)
  *A61K 39/085* (2006.01)
  *A61K 39/09* (2006.01)
  *A61K 39/095* (2006.01)
  *A61K 39/104* (2006.01)
  *C07K 16/40* (2006.01)
  *A61K 39/00* (2006.01)

(52) U.S. Cl.
  CPC ........ *C12N 9/0008* (2013.01); *A01K 67/0275* (2013.01); *A61K 39/0258* (2013.01); *A61K 39/0266* (2013.01); *A61K 39/085* (2013.01); *A61K 39/092* (2013.01); *A61K 39/095* (2013.01); *A61K 39/104* (2013.01); *C07K 16/40* (2013.01); *C12Y 102/01012* (2013.01); *A01K 2217/00* (2013.01); *A61K 2039/505* (2013.01); *A61K 2039/55* (2013.01); *A61K 2039/57* (2013.01); *C07K 2317/76* (2013.01)

(58) Field of Classification Search
  CPC .............. C12N 9/0008; A61K 67/0275; A61K 39/0258; A61K 39/0266; A61K 39/085; A61K 39/092; A61K 39/104; A61K 2039/505; A61K 2039/55; A61K 2039/57; C07K 16/40; C07K 2317/76; C12Y 102/01012; A01K 2217/00

See application file for complete search history.

(56) References Cited

U.S. PATENT DOCUMENTS

| 10,706,955 B2 * | 7/2020 | Bremel | G16B 40/20 |
| 2013/0332133 A1 * | 12/2013 | Horn | G16B 50/00 |
| | | | 703/11 |

FOREIGN PATENT DOCUMENTS

| WO | WO 99/55893 A1 | 11/1999 |
| WO | WO 2006/086561 A2 | 8/2006 |
| WO | WO 2008/020108 A1 | 2/2008 |
| WO | WO 2010/150242 A2 | 12/2010 |
| WO | WO 2011/025524 A1 | 3/2011 |
| WO | WO 2011/067758 A2 | 6/2011 |
| WO | WO 2014/055897 A2 | 4/2014 |
| WO | WO 2015/189422 A1 | 12/2015 |

OTHER PUBLICATIONS

UniProtKB/Swiss-Prot:P04406.3, [online], Apr. 16, 2014 https://www.ncbi.nlm.nih.gov/protein/120649?sat=18&satkey=5637490.
GenBank CAD44376.1, [online], Apr. 15, 2005 https://www.ncbi.nlm.nih.gov/protein/CAD44376.1.
Ayres, C. et al. "Structure of *Streptococcus agalactiae* glyceraldehyde-3-phosphate dehydrogenase holoenzyme reveals a novel surface", Acta Crystallographica Section F, Structural Biology Communications, 2014, F70, p. 1333-1339.
Aguilera et al., "NAD+-Dependent Post-Translational modification of *Escherichia coli* Glyceraldehyde-3-phosphate dehydrogenase", International Microbiology, vol. 12, pp. 187-192 (2009).
Aguilera et al., "Secretion of the housekeeping protein glyceraldehyde-3-phosphate dehydrogenase by the LEE-encoded type III secretion system in enteropathogenic *Escherichia coli*", Int. Microbiol 12(3); pp. 187-192 (2009).
Andrade et al., "TLR2-Induced IL-10 Produciton Impairs Neutrophil Recruitment to Infected Tissues during Neonatal Bacterial Sepsis", J immunol, vol. 191, pp. 4759-4768 (2013).
Argiro L. et al. "Identification of a candidate vaccine peptide on the 37 kDa *Schistosoma mansoni* GAPDH", Vaccine, vol. 18, No. 19, 2000, p. 2039-2048.
Barton, MD, et al., "Causes of Death in the Exremely Low Birth Weight Infant", Pediatrics, vol. 103, No. 2, pp. 446-451, Feb. 1999.

(Continued)

*Primary Examiner* — Robert A Zeman
(74) *Attorney, Agent, or Firm* — COOLEY LLP; Matthew Pavao; Andrew R. Henderson

(57) ABSTRACT

The invention provides peptides derived from a ubiquitous protein, and nucleic acids encoding such peptides. The invention extends to various uses of these peptides and nucleic acids, for example, as antigens for use in vaccines per se and in the generation of antibodies for use in therapeutic drugs for the prevention, amelioration or treatment of infections caused by sepsis-inducing bacteria. The invention particularly benefits immunocompromised hosts such as neonates, babies, children, women of fertile age, pregnant women, foetuses, the elderly and diabetics.

2 Claims, 21 Drawing Sheets

Specification includes a Sequence Listing.

(56) References Cited

OTHER PUBLICATIONS

Bishton et al., "The role of granulocyte transfusions in neutropenic patients", Br. J. Haematol, vol. 127, pp. 501-508 (2004).
Bourgeois-Nicolaos, et al., "Evaluation of the Cepheid Xpert GBS Assay for Rapid Detection of Group B Streptococci in Amnoitics Fluids from Pregnant Women with Premature Rupture of Membranes", Journal of Clinical Microbiology, pp. 1305-1306, (Apr. 2013).
Brocklehurest P., et al., "Granulocyte transfusions for neonates with confirmed or suspected sepsis and neutropenia", Cochrante Database of Systematic Reviews, Issue 10, pp. 1-25, (2011).
Brun-Buisson, MD, et al., "Incidence, Risk Factors, and Outcome of Severe Sepsis and Septic Shock in Adults" JAMA, vol. 274, No. 12, pp. 968-974, (1995).
Calderon-Gonzalez et al., "Cellular vaccines in listeriosis: role of the *Listeria* antigen GAPDH", Frontiers in Cellular and Infection Microbiology, vol. 4, p. 1-11, 2014.
Carr "Granulocyte-macrophage colony stimulating factor administered as prophylaxis for reduction of sepsis in extremely preterm, small for gestational age neonates (the PROGRAMS trial): a single-blind, mutlicentre, randomised controlled trial", www.thelancet.com, vol. 373, pp. 226-233, (2009).
Dellinger MD., et al., Surviving Sepsis Campaign: International guidelines for management of severe sepsis and septic shock: Crit Care Med, vol. 36, pp. 296-327 (2008).
Doran et al., "Molecular pathogenesis of neonatal group B streptococcal infection: no longer in its infancy", Molecular Microbiology, vol. 54(1), pp. 23-31, (2004).
Edmond et al., "Group B streptococcal disease in infants aged younger than 3 months: systematic reviw and meta-analysis", www.thelancet.com, vol. 379, pp. 547-556, (2012).
Edmond et al., "New Approaches to Preventing, Diagnosing, and Treating Neonatal Sepsis", PloS Medicing, vol. 7, Issue 3, pp. 1-8 (2010).
Egea et al., "Role of secreted glyceraldehyde-3-phosphate dehydrogenase in the infection mechanism of enterohemorrhagic and enteropathogenic *Escherichia coli*: Interaction of the extracellular enzyme with human plasminogen and fibrinogen", Int J Biochem Cell Biol, 39(6), pp. 1190-1203 (2007).
Ellis, "New Technology for Making Vaccines", Vaccines, Ch. 29, 1988, p. 568-574.
Goji et al.,"Characterization of two proteins of *Staphylococcus aureus* isolated from bovine clinical mastitis with homology to glyceraldehyde-3-phosphate dehydrogenase", Vet Microbiol vol. 99 3-4, pp. 269-279 (2004).
Goldberg et al., "Infection-related stillbirths", Lancet, vol. 375, pp. 1482-1490, (2010).
Goldenberg RL, et al., "Intrauterine Infection and Preterm Delivery", The New England Journal of Medicine, pp. 1500-1507, May 18, 2000.
Groselj-Grenc et al., "Neutrophil and monocyte CD64 indexes, lipopolysaccharide-binding protein, procalcitonin and C-reactive protein in sepsis of critically ill neonates and children", Intensive Care Med, vol. 35, pp. 1950-1958 (2009).
Henneke et al., "Lipoproteins are Critical TLR2 Activating Toxins in Group B Streptococcal Sepsis", J Immunol, vol. 180, pp. 6149-6158, (2008).
Heppner, MD, et al., "Infections in the Elderly", Crit Clin Care 29, pp. 757-774, (2013).
Hornik et al., "Early and late onset sepsis in very-low-birth-weight infants from a large group of neonatal intensive care units", Early Human Development 88, pp. 69-74 (2012).
Jacobsson et al., "The epidemiology of and risk factors for invasive *Staphylococcus aureus* infections in western Sweden", Scand J. Infect Dis., vol. 39, pp. 6-13 (2007).
Kaufman D., "Clinical Microbiology of Bacterial and Fungal Sepsis in Very-Low-Birth-Weight Infants", Dept. of Pediatrics Div., vol. 17, No. 3, pp. 638-680 (2004).

Kerro-Dego et al., "Role of GapC in the pathogenesis of *Staphylococcus aureus*", Vaccine and Infections Disease Organization (VIDO), 156(3-4), pp. 443-447 (2012).
Kronforst et al., "A Neonatal Model of Intravenous *Staphylococcus epidermidis* Infection in Mice <24 h Old Enables Characterization of Early Innate Immune Responses", Opn Access Freely, vol. 7, issue 9, pp. 1-10, (2012).
Kumar Johri, et al., "Group B *Streptococcus*: global incidence and vaccine development", Nature Publishing Group, vol. 4, pp. 932-942, (2006).
Lawn et al., "4 million neonatal deaths: When?Where?Why?" Neonatal Survival 1, vol. 365, pp. 891-900, Mar. 5, 2005.
Lin et al., "*Klebsiella pneumonia* liver abscess in diabetic patients: association of glycemic control with the clinical characteristics" BMC Infect Dis, vol. 13:56, pp. 1-7, (2013).
Linden, MD, et al. "Approach to the Imunocompromised Host with Infection in the Intensive Care Unit", Infect Dis Clin N Am 23, pp. 535-556, (Apr. 14, 2009).
Liong et al., "Glycolytic enzymes associated with the cell surface of *Streptococcus pneumonia* are antigenic in humans and elicit protective immune responses in the mouse", Clin Exp Immunol, vol. 138, pp. 290-298, (2004).
Lukacs et al., "Clinical Sepsis in Neonates and Young Infants", The Journal of Pediatrics, vol. 160, No. 6, pp. 960-965, (Jun. 2012).
Machata et al. , "Lipoproteins of *Listeria monocytogenes* are Critical for Virulence and TLR2-Mediated Immune Activation", J. Immunol vol. 181, pp. 2028-2035, (2008).
Madureira et al., "Inhibition of IL-10 Production by Maternal Antibodies against Group B *Streptococcus* GAPDH Confers Immunity to Offspring by Favoring Neutrophil Recruitment", plospathogrens, vol. 7, issue 11, pp. 1-14, (2011).
Madureira et al., "*Streptococcus agalactiae* GAPDH is a Virulence-Associated Immunomodulatory Protein", The Journal of Immunology, vol. 178, pp. 1379-1387 (2007).
Melvan et al., "Neonat Sepsis and Neutrophil Insufficiencies", Int Rev. Immunol 29, pp. 315-348, (2010).
Mullholland, M.D. et al., "Bacterial Infections—A Major Cause of Death among Children in Africa", N.Eng. J. Med 352;1, pp. 75-77, Jan. 6, 2005.
Purves et al. "Comparison of the Regulation, Metabolic Functions, and Roles in Virulence of the Glyceraldehyde-3-Phosphate Dehydrogenase Homologues gapA and gapB in *Staphylococcus aureus*", Infection and Immunity, (Dec. 2010), pp. 5223-5232.
Schrag et al. "Group B streptococcal vaccine for resource-poor courtires", Lancet vol. 378; pp. 11-12, (2011).
Seifert et al. "Characterization of group B streptococcal glyceraldehyde-3-phosphate dehydrogenase: surface localization, enzymatic activity, and protein-protein interactions", Can J. Microbiol (5), pp. 350-356, May 12, 2003.
Shann "Sepsis in Babies: should we stimulate the phagocytes?", Lancet vol. 373, pp. 188-190, (2009).
Skoff et al., "Increasing Burden of Invasive Group B Streptococcal Disease in Nonpregnant Aduelts, 1990-2007", Clin Infect Dis, vol. 49, pp. 58-92, (2009).
Smith, et al., "Concordance of Gastrointestinal Tract Colongization and Subsequent Bloodstream Infections With Gram-negative Bacilli in Very Low Birth Weights Infants in the Neonatal Intensive Care Unit", Pediatr Infect Dis J, vol. 29, pp. 831-835 (2010).
Stoll et al. "Early Onset Neonatal Sepsis: The Burden of Group B Streptococcal and *E. coli* Disease Continue", Pediatrics, vol. 127, No. 5, May 2011.
Stoll MD, et al., "Neurodevelopmental and Growth Impairment Among Extremely Low-Birth-Weight Infants With Neonatal Infection", American Medical Association, vol. 292, No. 19, pp. 817-826, (2004).
Stoll MD, et al., "Very Low Birth Weight Preterm Infants With Early Onset Neonatal Sepsis", Pediatr Infect Dis J, vol. 24, pp. 635-639 (2005).
Stoll, M.D., "Changes in Pathogens Causing Early-Onset Sepsis in Very-Low-Birth-Weight Infants", N. Engl. J. Med, vol. 347, No. 4, pp. 240-247, Jul. 25, 2002.

(56) References Cited

OTHER PUBLICATIONS

Tazi et al., "The surface protein HvgA mediates group B *Streptococcus* hypervirulence and meningeal tropism in neonates", J. Exp. Med, vol. 207, pp. 313-2313-313-2322, (2010).
Thompson, et al., "CLUSTAL W: Improving the sensitivity of progressive multiple sequence alignment through sequence weighting, position-specific gap penalities and weight matrix choice", Nucleic Acids Research, vol. 22, No. 22, pp. 4673-4680, (1994).
Thompson et al., "The CLUSTAL_X windows interface: flexible strategies for multiple sequence alignment aided by quality analysis tools", Nucleic Acides Res. 25(24), pp. 4876-4882 (1997).
Tunio, S.A. et al. "Molecular and immunological characterisation of glycolytic enzymes: FBA and GAPDH-1 of *Neisseria meningitidis*", Molecular Microbiology, vol. 76, 2010, p. 1-294. Retrieved from the Internet: URL:http://eprints.nottingham.ac.uk/13387/1/537790. pdf.
Tunio et al., "The role of glyceraldehyde 3-phosphate dehydrogenase (GapA-1) in *Neisseria meningitides* adherence to human cells", BMC Microbiol, vol. 10, pp. 1-10 (2010).
Tushinski "Survival of Mononuclear Phagocytes Depends on a Lineage-Specific Growth Factor That the Differetiated Cells Selectively Destroy", Dept of Microbiology and Immunology and Dept of Cell Biology, vol. 28, pp. 71-81 (1982).
Van Den Hoogen et al., "Long-Term Trends in the Epidemiology of Neonatal Sepsis and Antibiotic Susceptibility of Causative Agents", Neonatology, vol. 97, pp. 22-28, (2010).
Voßhenrick et al. "Thymic stromal-derived lymphopoietin distinguishes fetal from adult B cell development", Nature Immunology, vol. 4, No. 8, pp. 773-779, (Aug. 2003).
Watson et al., "The Epidemiology of Severe Sepsis in Children in the United States", Am J Respir Crit Care Med 167, pp. 695-701 (2003).
Weidang, Li et al., "Peptide Vaccine: Progress and Challenges", Vaccines (Basel), 2014, 2(3): 515-536.
Wynn MD, et al., "Role of Innate Host Defense in Susceptibility to Early-Onset Neonatal Sepsis", Clin Perinatol, vol. 37, pp. 307-337, (2010).
Yildiz et al., "Sepsis and Meningitis due to *Listeria monocytogenes*", Yonsei Medical Journal, vol. 48, No. 3, p. 433-439, 2007.

\* cited by examiner

SEQ ID NO:

| | | | |
|---|---|---|---|
| 1 | GBS_NEM316 | MVVKVGINGFGRIGRLAFRRIQ--NVEG-VEVTRINDLTDPNMLAHLLKYDTTQGRFDGT | 57 |
| 2 | E_coli_K1 | -MSKVGINGFGRIGRLVLRRLL--EVKSNIDVVAINDLTSPKILAYLLKHDSNYGPFPWS | 57 |
| 3 | S_aureus_Newman | MAVKVAINGFGRIGRLAFRRIQ---EVEG-LEVVAVNDLTDDDMLAHLLKYDTMQGRFTGE | 57 |
| 4 | S_pneumoniae_Tigr4 | MVVKVGINGFGRIGRLAFRRIQ---NVEG-VEVTRINDLTDPVMLAHLLKYDTTQGRFDGT | 57 |
| 5 | K_pneumoniae | -MEKLGINGFGRIGRLVLRRLL--EVDSSLEVVAINDLTSPKVLAYLLKHDSNYGPFPWS | 57 |
| 6 | P_aeruginosa_PA01 | NTIRLAINGFGRIGRNVLRALYTGHYREQLQVVAINDLGDAAVNAHLFQYDSVHGHFPGE | 60 |
| 7 | N_meningitidis_MenB | MSIKVAINGFGRIGRLALRQIE---KAHD-IEVVAVNDLTPAEMLLHLFKYDSTQGRFQGT | 57 |

| | | | |
|---|---|---|---|
| | GBS_NEM316 | VEVKEGGFEVNGQFVKVSAEREPANIDWATDGVEIVLEATGFFASKEKAEQRIHENGAKK | 117 |
| | E_coli_K1 | VDYTEDSLIVNGKSIAVYAEKEAKNIPWKARGAEIIVECTGFYTSAEKSQAHLDA-GAKK | 116 |
| | S_aureus_Newman | VEVUVDGGFRVNGKEVKSFSEPDASRLPWEDLNIDVVLECTGFYTDKDKAQAHIEA-GAKK | 116 |
| | S_pneumoniae_Tigr4 | VEVKEGGFEVNGKFIKVSAERDPEQIDWATDGVETVLEATGFFAKKEAAERHLKG-GAKK | 116 |
| | K_pneumoniae | VDFYEDALIVNGKTITVYAEKEAQKIPWQAAGAEVIVECTGFYTSAERSQAHIQA-GARK | 116 |
| | P_aeruginosa_PA01 | VEHDRESLRVMGDRIAVSAIRNPAELPWKSLGVDIVLECSLFTSRDFAAAAHLQA-GAGK | 119 |
| | N_meningitidis_MenB | AELRDDAIVVNGKEIRVFANPNPEELPWGELGVDVILECTGFFTNKTKAEAHIRA-GAKK | 116 |

| | | | |
|---|---|---|---|
| | GBS_NEM316 | VVITAPGGNDVKTVVFNTNKDILDGTETVISGASCTTNCLAPMARALQDNPGVKQGLMTT | 177 |
| | E_coli_K1 | VLISAPAG-EMKTIVYNVNDDTLDGNKDTIYSVASCTTNCLAPMARAIHDSPGIEVGTMTT | 175 |
| | S_aureus_Newman | VLISAPATGDLKTIVFNTNHQELDGSETVVSGASCTTNSLAPVARVLNDDFGLVEGLMTT | 176 |
| | S_pneumoniae_Tigr4 | VVITAPGGNDVKTVVFNTNHDVLDGTETVISGASCTTNCLAPMAKALQDNFGVVEGLMTT | 176 |
| | K_pneumoniae | VLISAPAG-EMKTIVYNVNDTLTPDDTIISVASCTTNCLAPMAKVLQDAFGITVGTMTT | 175 |
| | P_aeruginosa_PA01 | VLISAPGKDVEATVVYGVNHEVLRASHRIVSNASCTTNCLAPVAQVLHRELGIEHGIMTT | 179 |
| | N_meningitidis_MenB | VVISAPGGNDVKTVVYGVNQDILDGSETVISAASCTTNCLAPMAAVLQKEFGVVEGLMTT | 176 |

| | | | |
|---|---|---|---|
| | GBS_NEM316 | IHAYTGDQMILDGPHRGGDLRRARAGAANIVPNSTGAAKAIGLVIPELNGKLDGAAQRVP | 237 |
| | E_coli_K1 | IHAYTGTQSLVDGP-RGKDLRASRAAAENIIPHTTGAAKAIGLVIPELSGKLKGHAQRVP | 234 |
| | S_aureus_Newman | IHAYTGDQNTQDAPHKKGDKRAARAAAENIIPNSTGAAKAIGRVIPEIDKKLDGSAQRVP | 236 |
| | S_pneumoniae_Tigr4 | IHAYTGDQMILDGPHRGGDLRRARAGAANIVPNSTGAAKAIGLVIPELNGKLDGSAQRVP | 236 |
| | K_pneumoniae | IHAYTGTQSLVDGP-RGKDLRASRAAAEMVIPHTTGAAKAIGLVIPALSGKLKGHAQRVP | 234 |
| | P_aeruginosa_PA01 | IHAYTNDQHLSDVY--HPDLYRARSATQSMIFTKTGAAKEAVGLVLPELAGKLTGLAVRVP | 237 |
| | N_meningitidis_MenB | IHAYTGDQNTILDAPHREGDLRRARAAAALNIVPNSTGAAKAIGLVIPELNGKLDGSAQRVP | 236 |

| | | | |
|---|---|---|---|
| | GBS_NEM316 | VPTGSVTELVATLEK-DVTVEEVNAAMKAAA---NDSYGYTEDPIVSSDIVGISYGSLFDA | 294 |
| | E_coli_K1 | VKIGSVTELVSILGK-KVTAEEVNNALKKAIMNMESFGYTDEEIVSSDIIGSMFGSVFDA | 293 |
| | S_aureus_Newman | VATGSLTELTVVLEKQDVTVEQUNEAMFNAS---NESFGYTEDEIVSSDVVGMTYGSLFDA | 294 |
| | S_pneumoniae_Tigr4 | IPTGSVTELVAVLEK-NVTVDEVNAAMKAAS---NESYGYTEDPIVSSDIVGMSYGSLFDA | 293 |
| | K_pneumoniae | TKIGSVTELVSVLEK-KVTADEVNQAMKQAAEGNESFGYTEPEIVSSDIIGSKFGSIYDA | 293 |
| | P_aeruginosa_PA01 | VINVSLVDLTVQVAR-DTSVDEVNRLLREASEGSPVLGYNTQPLVSVDFNHDFRSSIFDA | 296 |
| | N_meningitidis_MenB | VASGSLTELVSILER-PVTKEEINAAMKAAA---SESYGYMEDQIVSSDVVGIEYGSLFDA | 293 |

| | | | |
|---|---|---|---|
| | GBS_NEM316 | TQTKVQTVDGNQLVKVVSNYDNEMSYTSQLVRTLEYFAKIAK | 336 |
| | E_coli_K1 | TQTEITAVGDLQLVKTVANWYDNEYGFVTQLIRTLEKFAKL-- | 333 |
| | S_aureus_Newman | TQTRVMSVGDRQLVKVAANYDNEMSYTAQLVRTLAYLAELSK | 336 |
| | S_pneumoniae_Tigr4 | TQEKVLDVDGRQLVKVVSWYDNEMSYTAQLVRTLEYFAKIAK | 335 |
| | K_pneumoniae | TQLEIVEAGGVQLVKTVANWYDNEYGFVTQLIRVLEKFAR--- | 332 |
| | P_aeruginosa_PA01 | NHTKVSGR-----LVRAMANYDNEWGFSNRMLDSALALAAARD | 334 |
| | N_meningitidis_MenB | TQTRVMTWSGKQLVKTVANWYDNEMSYTCQLVRTLEYFASKI- | 334 |

Fig. 1

Peptide 1: RIQEVEGLEVTR
Peptide 2: DVTVEEVNAAM

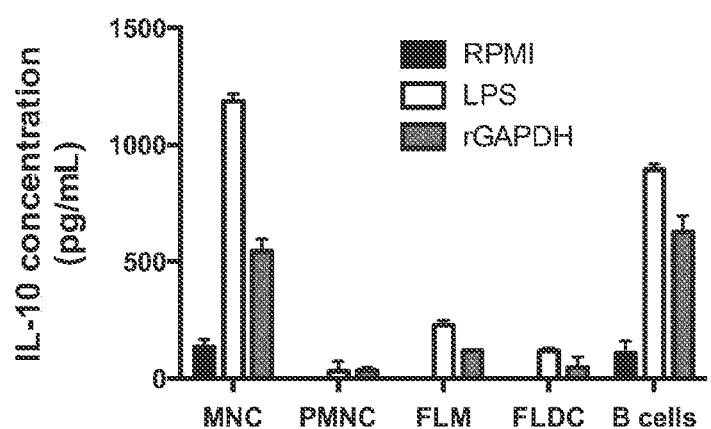
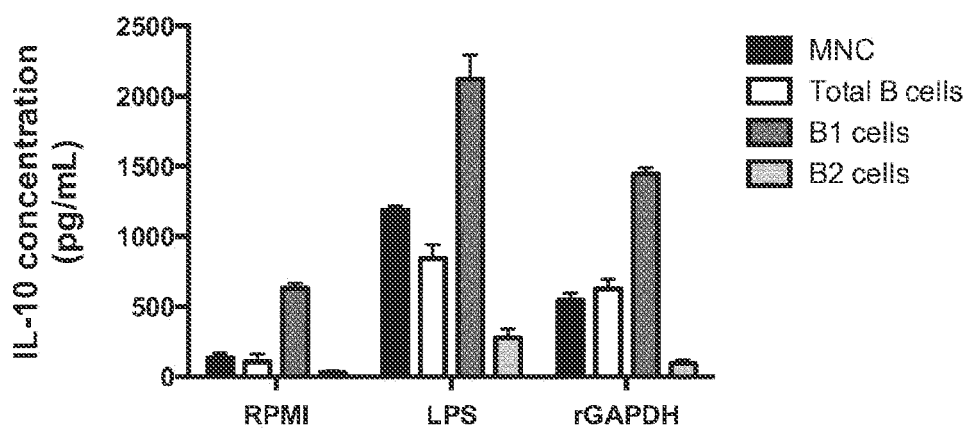
Fig. 4

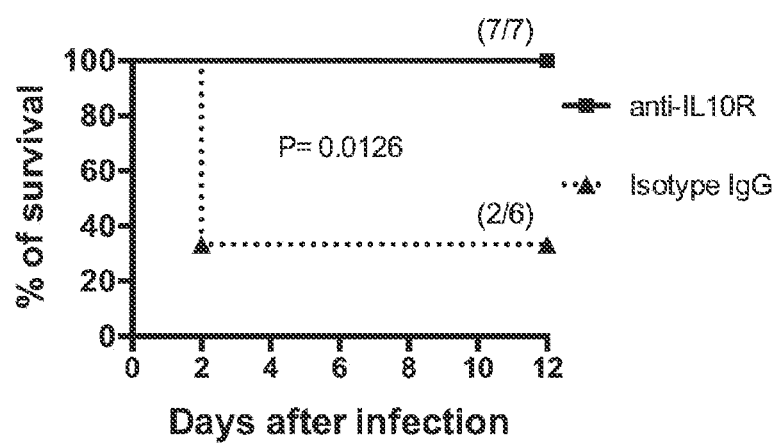
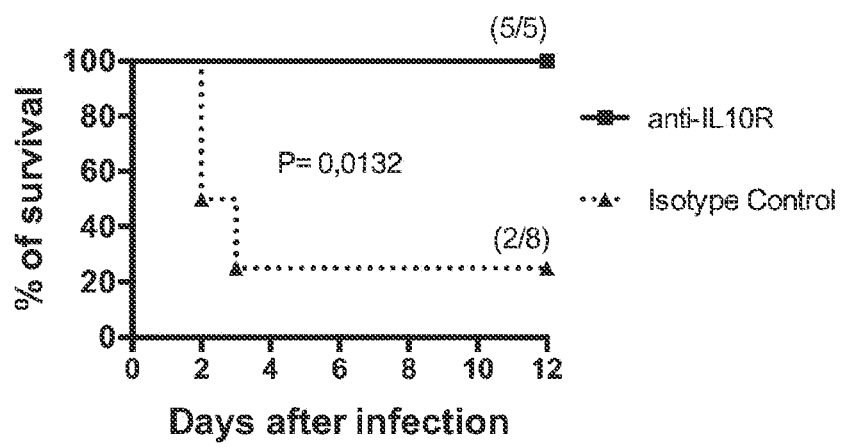
Fig. 8

*E. coli*

Peptide: EVKDGHLIVNGKK

Fig. 12

Peptide 1: TGHYREQLQ
Peptide 2: EHDAESLRVMGDR

Fig. 13

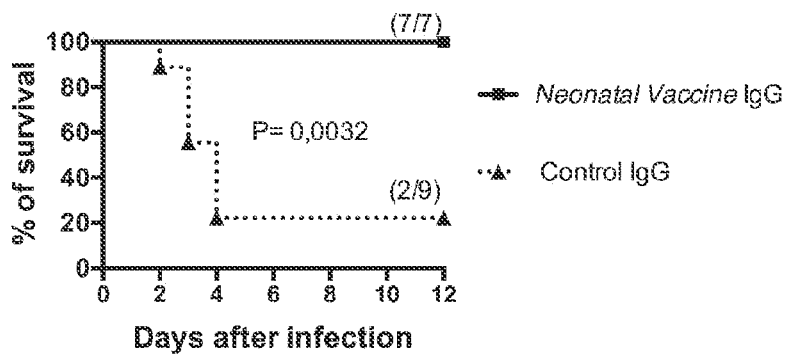
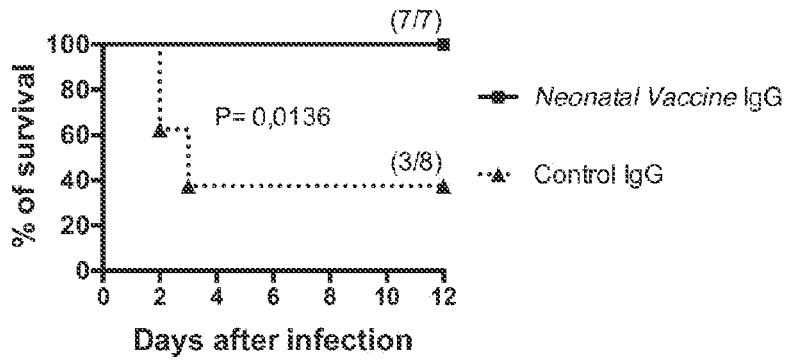
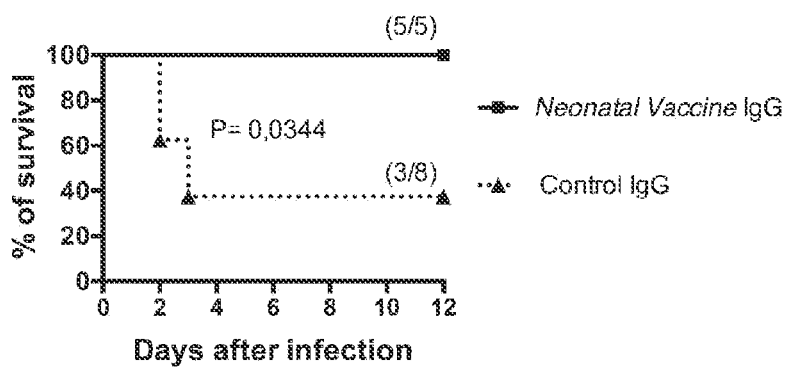
Fig. 18

VACCINE FOR IMMUNOCOMPROMISED HOSTS

CROSS REFERENCE TO RELATED APPLICATIONS

This application is a continuation application of U.S. application Ser. No. 15/313,327, filed Nov. 22, 2016, which is a U.S. National Phase patent application of PCT/EP2015/063243, filed Jun. 12, 2015, which claims priority to European Patent Applications No. 15398003.2, filed Mar. 30, 2015, and Ser. No. 14/398,006.8 filed Jun. 12, 2014, all of which are hereby incorporated by reference in the present disclosure in their entirety.

FIELD OF THE INVENTION

The present invention relates to diseases, disorders and conditions caused by sepsis-inducing bacteria and particularly, although not exclusively, to the treatment and prevention of sepsis and sepsis-related pathologies. The invention extends to novel peptides and their encoding nucleic acids, and to the use of these peptides to create vaccines for the prevention of infection by sepsis-inducing bacteria by immunisation or by passive antibody transfer. This invention particularly benefits immunocompromised hosts such as neonates, babies, children, women of fertile age, pregnant women, foetuses, the elderly and diabetics.

INCORPORATION BY REFERENCE OF SEQUENCE LISTING

The contents of the text file named UDPR-001C01US Sequence Listing.txt, which was created on Oct. 10, 2023 and is 45,056 bytes in size, are hereby incorporated by reference in their entireties.

BACKGROUND OF THE INVENTION

Sepsis is a major cause of neonatal morbidity and mortality. According to the World Health Organization (WHO), approximately one million deaths per year are caused by neonatal sepsis [1-3]. In addition, 30-50% of the surviving neonates suffer from long term sequelae such as cognitive impairments, seizures or deafness [4].

Neonatal infections can occur before birth (in utero), during labour or after birth. In utero infections are caused by the ascending of commensal bacteria from the mother's genital tract into the amniotic fluid [1]. Infections that occur during labour are caused by the aspiration of microbes colonising the mucosa from the mother's genital tract. In both causes, up to 87% of infections are caused by Group B *Streptococcus* (GBS; also known as *Streptococcus agalactiae* (*S. agalactiae*)), *Escherichia coli* (*E. coli*) and *Klebsiella* spp. [5-7]. Although vertical transmission of bacteria may also be the cause of infections occurring after birth, most of these infections are caused by *Staphylococcus* spp., *Streptococcus pneumoniae* (*S. pneumoniae*) or *Pseudomonas* spp. [2,3,7-12].

In utero infections are also an important cause of preterm births. In fact, 50-80% of preterm births at <32 weeks of gestation are caused by ascending bacterial infections [9,13-17].

The current treatment available for neonatal sepsis is based only on antibiotic administration. However, whilst there have been dramatic declines in GBS infections since the implementation of intrapartum antibiotic prophylaxis, the increase of host resistance to the used antibiotics, as well as its questionable use in pregnant humans, highlights the need for an alternative prophylactic strategy. Immunotherapies adopted for neonatal sepsis were, however, so far, completely delusive.

The uniqueness of the neonate's immune system is based on different circumstances. Importantly, birth represents a dramatic passage from the almost sterile environment offered by the mother's womb into a "hostile" antigen- and pathogen-rich outside world, to which the baby's immune system needs to learn to be tolerant. In that sense, the first months of a baby's life are characterised by an active immune-tolerant status in order to control excessive responses to new antigens, which, in turn, may increase risk of infection. On the other hand, due to the limited exposure to antigens in utero and the well-described defects in neonatal adaptive immunity, newborns must rely on their innate immune systems for protection to infections. In fact, neutropenia (a granulocyte disorder characterised by an abnormally low number of neutrophils), is strongly associated with severe sepsis [13,18-23].

Although neutropenia is usually explained by the immaturity of the neonate immune system, the inventors have previously described that neonatal susceptibility to GBS infections is related to neonatal predisposition to produce high amounts of interleukin-10 (IL-10), an immunosuppressive molecule, rapidly after bacterial challenge [24]. Their results demonstrated that this early immunosuppression caused by IL-10 production, and not the immaturity of the neonatal immune system, was the main reason for the neutropenia observed in GBS infections [24]. Moreover, they have identified extracellular glyceraldehyde-3-phosphate dehydrogenase (GAPDH) as the bacterial factor responsible for this early IL-10 production [24,25]. They have used recombinant GAPDH (rGAPDH) in a maternal vaccine and shown it to be highly effective in protecting the progeny against lethal GBS infections [24]. They have shown that this protection can also be obtained either by antibody neutralisation of GBS GAPDH or by blocking IL-10 binding to its receptor [24].

*Neisseria meningitidis* (*N. meningitidis*), often referred to as meningococcus, is a major cause of life-threatening sepsis, meningitis and other forms of meningococcal disease in babies and infants, but it is rarely found during the neonatal period. It is also the main cause of bacterial meningitis in children and young adults. Serotype distribution varies markedly around the world. In the US, for example, serogroup B is the predominant cause of disease and mortality, followed by serogroup C; serogroup A, however, has been the most prevalent in Africa and Asia. The multiple subtypes have hindered development of a universal vaccine for meningococcal disease; a small number of vaccines are, however, available against individual, or in one case, two, serogroups.

Along with neonates, babies, infants and children, immunocompromised adults such as the elderly are also very susceptible to bacterial infections and sepsis [26]. Pneumonia, bacteremia and sepsis are very frequent in the elderly and constitute an important cause of mortality and morbidity. These infections are generally mixed, frequently due to anaerobes, *S. pneumoniae, Staphylococcus aureus* (*S. aureus*) and *Haemophilus influenzae*, although gram-negative intestinal bacteria (*Klebsiella pneumoniae* (*K. pneumoniae*) and other Enterobacteriaceae), *Pseudomonas aeruginosa* (*P. aeruginosa*) (in bedridden patients) and GBS can also be a cause [26].

Thus, the mortality associated with severe sepsis and septic shock observed in intensive care units is around 30% [27]. Importantly, the incidence of immunocompromised patients has increased steadily for the last 20 years [28] and immunodeficiency is a prognostic factor that is more and more often identified as associated with the increased mortality attributed to severe sepsis and septic shock [29].

Also, diabetic patients have increased susceptibility to invasive infections caused by *Staphylococcus* spp. and GBS [30,31]. In East Asia, diabetes is a well-known risk factor for liver abscess caused by *K. pneumoniae* [32].

The data found in the literature therefore indicate that there is a small number of microbial pathogens that are consistently associated with sepsis across these patient groups.

SUMMARY OF THE INVENTION

Having focused their efforts on GAPDH, the inventors have now demonstrated that this enzyme is an extracellular virulence factor of all relevant sepsis-inducing bacteria. The inventors believe that they are the first ever to identify a novel array of GAPDH-derived peptides that are capable of eliciting antibodies that are specific for bacterial, rather than human, GAPDH. As described and exemplified fully herein, these novel peptides are extremely useful for the generation of vaccines for preventing infectious diseases caused by sepsis-inducing bacteria, particularly in immunocompromised hosts such as neonates, babies, children, women of fertile age, pregnant women, foetuses, the elderly and diabetics. In addition, the elicited antibodies can be used as therapeutic agents for treating existing infections, particularly in these patient populations.

Hence, according to a first aspect of the invention, there is provided an isolated peptide that has at least 90% amino acid sequence identity with a peptide found within GAPDH of one or more sepsis-inducing bacteria, and has less than 10% amino acid sequence identity with a peptide found within human GAPDH, or a functional fragment or functional variant thereof.

The inventors were aware from their previous work that susceptibility to sepsis caused by GBS is strongly associated with the host's tendency to produce high levels of IL-10 upon contact with bacterial GAPDH [24]. However, there was no reason for the inventors to consider or suspect the same to be true for other sepsis-inducing bacteria. Indeed, while it was known that other sepsis-inducing bacteria possess GAPDH (because this enzyme is ubiquitous), it was not known or expected that GAPDH from the other sepsis-inducing bacteria causes IL-10 to be produced by host cells. Thus, the discovery by the inventors that GAPDH is an extracellular virulence factor of all relevant sepsis-inducing bacteria was completely surprising.

Furthermore, there is currently no vaccine that efficiently protects neonates and foetuses against infections caused by each of the genera of sepsis-inducing bacteria individually. In addition, the preventive or therapeutic strategies used to combat sepsis in immunocompromised adults such as the elderly and diabetics are far from effective. As explained herein, antibiotics only resolve part of the problem, since in the cases of late-onset sepsis they are often administered too late, and are ineffective in preventing sepsis-associated morbidity. Moreover, antibiotics are not able to prevent in utero infections. The peptides, fragments and variants of the first aspect thus have significant utility in creating a variety of useful and much-needed vaccines, particularly for these patient populations.

A vaccine is the most cost-effective treatment for infectious diseases, even more when the same vaccine could prevent infections caused by different human pathogens in different patient groups. The present invention relates to the prevention, treatment and amelioration of infectious diseases caused by sepsis-inducing bacteria, particularly GBS, *E. coli*, *Staphylococcus* spp., *S. pneumoniae*, *K. pneumoniae*, *N. meningitidis* and/or *Pseudomonas* spp.

DETAILED DESCRIPTION

The invention described herein is based upon the inventors' surprising discovery that the susceptibility to bacterial sepsis is strongly associated with the host's tendency to produce high levels of IL-10 upon contact with bacterial GAPDH, for all sepsis-inducing bacteria.

Susceptibility to sepsis is very frequent in different risk groups. Nevertheless, the microbial pathogens that are associated with sepsis are highly conserved in the different groups of susceptible hosts. The most relevant bacteria associated with sepsis in humans are GBS, *E. coli*, *Staphylococcus* spp., *S. pneumoniae*, *K. pneumoniae*, *Pseudomonas* spp. and *N. meningitidis*, and the inventors have surprisingly found that all of these bacteria secrete GAPDH.

As such, the sepsis-inducing bacteria may preferably be selected from a group of bacteria consisting of GBS, *E. coli*, *Staphylococcus* spp., *S. pneumoniae*, *K. pneumoniae*, and *Pseudomonas* spp. and *N. meningitidis*. In an embodiment, the *Staphylococcus* spp. is *S. aureus*. In another embodiment, the *Pseudomonas* spp. is *Pseudomonas aeruginosa* (*P. aeruginosa*). In another embodiment, the *N. meningitidis* is *N. meningitidis* serotype B (MenB). In an embodiment, the sepsis-inducing bacteria are not GBS.

The amino acid sequences of GAPDH from GBS, *E. coli*, *S. aureus*, *S. pneumoniae*, *K. pneumoniae*, *P. aeruginosa* and MenB (strain MC58) are identified herein as SEQ ID NOs: 1-7, respectively.

The amino acid sequence of GAPDH from GBS (UniProt Accession No. Q8E3E8) is identified herein as SEQ ID NO: 1, as follows:—

[SEQ ID NO: 1]
MVVKVGINGFGRIGRLAFRRIQNVEGVEVTRINDLTDPNMLAHLLKYDTT

QGRFDGTVEVKEGGFEVNGQFVKVSAEREPANIDWATDGVEIVLEATGFF

ASKEKAEQHIHENGAKKVVITAPGGNDVKTVVFNTNHDILDGTETVISGA

SCTTNCLAPMAKALQDNFGVKQGLMTTIHAYTGDQMILDGPHRGGDLRRA

RAGAANIVPNSTGAAKAIGLVIPELNGKLDGAAQRVPVPTGSVTELVATL

EKDVTVEEVNAAMKAAANDSYGYTEDPIVSSDIVGISYGSLFDATQTKVQ

TVDGNQLVKVVSWYDNEMSYTSQLVRTLEYFAKIAK

The amino acid sequence of GAPDH from *E. coli* (UniProt Accession No. D5D2F1) is identified herein as SEQ ID NO: 2, as follows:—

[SEQ ID NO: 2]
MSKVGINGFGRIGRLVLRRLLEVKSNIDVVAINDLTSPKILAYLLKHDSN

YGPFPWSVDYTEDSLIVNGKSIAVYAEKEAKNIPWKAKGAEIIVECTGFY

TSAEKSQAHLDAGAKKVLISAPAGEMKTIVYNVNDDTLDGNDTIVSVASC

TTNCLAPMAKALHDSFGIEVGTMTTIHAYTGTQSLVDGPRGKDLRASRAA

-continued
AENIIPHTTGAAKAIGLVIPELSGKLKGHAQRVPVKTGSVTELVSILGKK

VTAEEVNNALKKATNNNESFGYTDEEIVSSDIIGSHFGSVFDATQTEITA

VGDLQLVKTVAWYDNEYGFVTQLIRTLEKFAKL

The amino acid sequence of GAPDH from *S. aureus* (UniProt Accession No. A6QF81) is identified herein as SEQ ID NO: 3, as follows:—

[SEQ ID NO: 3]
MAVKVAINGFGRIGRLAFRRIQEVEGLEVVAVNDLTDDDMLAHLLKYDTM

QGRFTGEVEVVDGGFRVNGKEVKSFSEPDASKLPWKDLNIDVVLECTGFY

TDKDKAQAHIEAGAKKVLISAPATGDLKTIVFNTNHQELDGSETVVSGAS

CTTNSLAPVAKVLNDDFGLVEGLMTTIHAYTGDQNTQDAPHRKGDKRRAR

AAAENIIPNSTGAAKAIGKVIPEIDGKLDGGAQRVPVATGSLTELTVVLE

KQDVTVEQVNEAMKNASNESFGYTEDEIVSSDVVGMTYGSLFDATQTRVM

SVGDRQLVKVAAWYDNEMSYTAQLVRTLAYLAELSK

Although only the sequence of GAPDH from *S. aureus* is provided here, all of the available GAPDH sequences from *Staphylococcus* spp. possess over 98% sequence similarity.

The amino acid sequence of GAPDH from *S. pneumoniae* (UniProt Accession No. Q97NL1) is identified herein as SEQ ID NO: 4, as follows:—

[SEQ ID NO: 4]
MVVKVGINGFGRIGRLAFRRIQNVEGVEVTRINDLTDPVMLAHLLKYDTT

QGRFDGTVEVKEGGFEVNGKFIKVSAERDPEQIDWATDGVEIVLEATGFF

AKKEAAEKHLKGGAKKVVITAPGGNDVKTVVFNTNHDVLDGTETVISGAS

CTTNCLAPMAKALQDNFGVVEGLMTTIHAYTGDQMILDGPHRGGDLRRAR

AGAANIVPNSTGAAKAIGLVIPELNGKLDGSAQRVPTPTGSVTELVAVLE

KNVTVDEVNAAMKAASNESYGYTEDPIVSSDIVGMSYGSLFDATQTKVLD

VDGKQLVKVVSWYDNEMSYTAQLVRTLEYFAKIAK

The amino acid sequence of GAPDH from *K. pneumoniae* (UniProt Accession No. B5XRG0) is identified herein as SEQ ID NO: 5, as follows:—

[SEQ ID NO: 5]
MSKLGINGFGRIGRLVLRRLLEVDSSLEVVAINDLTSPKVLAYLLKHDSN

YGPFPWSVDFTEDALIVNGKTITVYAEKEAQHIPWQAAGAEVIVECTGFY

TSAEKSQAHIQAGARKVLISAPAGEMKTIVYNVNDDTLTPDDTIISVASC

TTNCLAPMAKVLQDAFGITVGTMTTIHAYTGTQSLVDGPRGKDLRASRAA

AENVIPHTTGAAKAIGLVIPALSGKLKGHAQRVPTKTGSVTELVSVLEKK

VTADEVNQAMKQAAEGNESFGYTEEEIVSSDIIGSHFGSIYDATQLEIVE

AGGVQLVKTVAWYDNEYGFVTQLIRVLEKFAR

The amino acid sequence of GAPDH from *P. aeruginosa* (UniProt Accession No. P27726) is identified herein as SEQ ID NO: 6, as follows:—

[SEQ ID NO: 6]
MTIRLAINGFGRIGRNVLRALYTGHYREQLQVVAINDLGDAAVNAHLFQY

DSVHGHFPGEVEHDAESLRVMGDRIAVSAIRNPAELPWKSLGVDIVLECT

GLFTSRDKAAAHLQAGAGKVLISAPGKDVEATVVYGVNHEVLRASHRIVS

NASCTTNCLAPVAQVLHRELGIEHGLMTTIHAYTNDQNLSDVYHPDLYRA

RSATQSMIPTKTGAAEAVGLVLPELAGKLTGLAVRVPVINVSLVDLTVQV

ARDTSVDEVNRLLREASEGSPVLGYNTQPLVSVDFNHDPRSSIFDANHTK

VSGRLVKAMAWYDNEWGFSNRMLDSALALAAARD

Although only the sequence of GAPDH from *P. aeruginosa* is provided here, all of the available GAPDH sequences from *Pseudomonas* spp. possess over 98% sequence similarity.

The amino acid sequence of GAPDH from MenB (strain MC58) (UniProt Accession No. Q9JX95) is identified herein as SEQ ID NO: 7, as follows:—

[SEQ ID NO: 7]
MSIKVAINGFGRIGRLALRQIEKAHDIEVVAVNDLTPAEMLLHLFKYDST

QGRFQGTAELKDDAIVVNGKEIKVFANPNPEELPWGELGVDVILECTGFF

TNKTKAEAHIRAGARKVVISAPGGNDVKTVVYGVNQDILDGSETVISAAS

CTTNCLAPMAAVLQKEFGVVEGLMTTIHAYTGDQNTLDAPHRKGDLRRAR

AAALNIVPNSTGAAKAIGLVIPELNGKLDGSAQRVPVASGSLTELVSILE

RPVTKEEINAAMKAAASESYGYNEDQIVSSDVVGIEYGSLFDATQTRVMT

VGGKQLVKTVAWYDNEMSYTCQLVRTLEYFAGKI

Although only the sequence of GAPDH from MenB (strain MC58) is provided here, all of the available GAPDH sequences from the different serotypes of *N. meningitidis* possess 97.668% sequence similarity (http://www.uniprot.org/align/A20150610146R8 0D4XR).

The biochemical characterisation, enzymatic activity and surface localisation of GAPDH protein has been described for GBS [33]. Extracellular localisation has also been described for GAPDH from *E. coli* [34-36], *S. aureus* [37-39], and *S. pneumoniae* [40]. The inventors believe that they are the first authors to indicate an extracellular presence of *P. aeruginosa* and *N. meningitidis* GAPDH.

GAPDH is a phylogenetically conserved protein associated with energy metabolism, which is present in every cell type. Microbial GAPDH has approximately 30-40% sequence identity with human GAPDH. The amino acid sequence of human GAPDH (UniProt Accession No. P04406) is identified herein as SEQ ID NO: 8, as follows:—

[SEQ ID NO: 8]
MGKVKVGVNGFGRIGRLVTRAAFNSGKVDIVAINDPFIDLNYMVYMFQYD

STHGKFHGTVKAENGKLVINGNPITIFQERDPSKIKWGDAGAEYVVESTG

VFTTMEKAGAHLQGGAKRVIISAPSADAPMFVMGVNHEKYDNSLKIISNA

SCTTNCLAPLAKVIHDNFGIVEGLMTTVHAITATQKTVDGPSGKLWRDGR

GALQNIIPASTGAAKAVGKVIPELNGKLTGMAFRVPTANVSVVDLTCRLE

-continued

KPAKYDDIKKVVKQASEGPLKGILGYTEHQVVSSDFNSDTHSSTFDAGAG

IALNDHFVKLISWYDNEFGYSNRVVDLMAHMASKE

Surprisingly, bacterial GAPDHs share up to 60% of their amino acid sequences, and the inventors have now demonstrated that, even more surprisingly, the GAPDHs from the preferred sepsis-inducing bacteria described herein (i.e. GBS, E. coli, Staphylococcus spp., S. pneumoniae, K. pneumoniae, Pseudomonas spp. and N. meningitidis) have a particularly high degree of sequence identity (see Example 7). Table 1 below provides the multiple alignment and sequence similarity percentages that were obtained from the ClustalW2 server, after submitting the amino acid sequences identified herein as SEQ ID NOs: 1-7 (according to the FASTA format of the previously indicated UniProt accession numbers). The sequence alignments are also shown in FIG. 1.

TABLE 1

Sequence comparison of bacterial GAPDH (GBS vs other bacteria)

| GAPDH sequence comparison | Sequence similarity (%) |
|---|---|
| GBS-E. coli | 60.61 |
| GBS-Staphylococcus spp. | 69.05 |
| GBS-S. pneumoniae | 91.94 |
| GBS-K. pneumoniae | 58.13 |
| GBS-Pseudomonas spp. | 44.31 |
| GBS-N. meningitidis (MenB) | 70.66 |

Accordingly, in a preferred embodiment, a peptide of the first aspect has at least 95%, at least 98%, at least 99% or 100% amino acid sequence identity with a peptide found within GAPDH of one or more sepsis-inducing bacteria.

Thus, preferably the peptide has at least 90%, at least 95%, at least 98%, at least 99% or even 100% amino acid sequence identity with a peptide found within one or more of the GAPDH sequences identified as SEQ ID NOs: 1-7.

For example, in one preferred embodiment, a peptide of the first aspect may have at least 90% amino acid sequence identity with a peptide found in SEQ ID NO: 1 (i.e. GAPDH from GBS). In another preferred embodiment, a peptide of the first aspect may have at least 95% amino acid sequence identity with a peptide found in SEQ ID NO: 2 (i.e. GAPDH from E. coli). In yet another preferred embodiment, the peptide may have at least 98% amino acid sequence identity with a peptide found in SEQ ID NO: 4 (i.e. GAPDH from S. pneumoniae). In another preferred embodiment, the peptide may have at least 95% amino acid sequence identity with a peptide found in SEQ ID NO: 1 (i.e. GAPDH from GBS), at least 98% amino acid sequence identity with a peptide found in SEQ ID NO: 4 (i.e. GAPDH from S. pneumoniae), and at least 99% amino acid sequence identity with a peptide found in SEQ ID NO: 6 (i.e. GAPDH from Pseudomonas spp.), and so on. It will be appreciated that any combination of possible sequence identities and possible sepsis-inducing bacteria described herein are envisaged and constitute part of the invention.

Having surprisingly discovered that GAPDH is highly conserved amongst sepsis-inducing bacteria, the inventors have identified a number of peptide sequences that are common to the bacterial GAPDHs, but are absent from human GAPDH (the expression "common to" can include consensus amino acid sequences that are borne out of the aligned bacterial sequences). Four preferred examples of these common peptide sequences are identified herein as SEQ ID NOs: 9-12. The peptides having the amino acid sequences of SEQ ID NOs: 9-12 are referred to herein as "Peptides 1-4", respectively, and these are shown below and in Table 2.

The amino acid sequence of Peptide 1 (i.e. common sequence 1) derived from GAPDH is identified herein as SEQ ID NO: 9, as follows:—

[SEQ ID NO: 9]
RIQEVEGLEVTR

The amino acid sequence of Peptide 2 (i.e. common sequence 2) derived from GAPDH is identified herein as SEQ ID NO: 10, as follows:—

[SEQ ID NO: 10]
DVTVEENAAM

The amino acid sequence of Peptide 3 (i.e. common sequence 3) derived from GAPDH is identified herein as SEQ ID NO: 11, as follows:—

[SEQ ID NO: 11]
EVKDGHLIVNGKV

The amino acid sequence of Peptide 4 (i.e. common sequence 4) derived from GAPDH is identified herein as SEQ ID NO: 12, as follows:—

[SEQ ID NO: 12]
EHDAESLRVMGDR

TABLE 2

Peptides derived from bacterial GAPDH for use as a vaccine.

| Bacteria | Amino acid sequence | SEQ ID NO. |
|---|---|---|
| 1 | RIQEVEGLEVTR | 9 |
| 2 | DVTVEENAAM | 10 |
| 3 | EVKDGHLIVNGKV | 11 |
| 4 | EHDAESLRVMGDR | 12 |

As an illustration, the derivation of Peptides 1 and 2 from the native sequences found in GADPH from GBS, S. aureus and S. pneumoniae, and the fact that the same sequences do not exist in GAPDH in humans, is shown in FIGS. 2 and 3. Peptides 3 and 4 were derived from the native sequences found in GADPH from E. coli, K. pneumoniae and/or P. aeruginosa, also as identified in FIGS. 2 and/or 3.

The amino acid sequence of each peptide according to the invention may thus be the same as that found in sepsis-inducing bacteria, or it may vary. However, if it varies, preferably the peptide has an amino acid sequence that is effectively a consensus sequence for the sepsis-inducing bacteria GAPDH, but not for human GADPH.

Accordingly, in one preferred embodiment, a peptide of the first aspect has an amino acid sequence substantially as set out in any one of SEQ ID NOs: 9-12.

It is expected that GAPDH from the different sepsis-inducing bacteria harbour further so consensus sequences, in addition to those identified as SEQ ID NOs: 9-12, that can be used to generate a peptide according to the present invention, for use as a vaccine. The peptides may have any sequence, but the sequence must not be substantively shared by GAPDH in humans.

Alternatively, a native amino acid sequence of GAPDH from sepsis-inducing bacteria can be used to generate a peptide of the invention. Table 3 shows putative peptide sequences taken from GAPDH of the indicated bacteria, which can be used in a vaccine of the invention to target at least the indicated bacteria. The peptides have been identified as bacterial GAPDH peptides that share no common sequence similarity with the human GAPDH isoform, after aligning each bacterial GAPDH amino acid sequence individually with human GAPDH (ClustalW2 server, followed by visual inspection and selection). These peptides are illustrative of many more GAPDH peptides that may be found amongst the surface peptides of the bacteria, and used to create a vaccine of the invention. Any peptide sequence within the native sequence may be used, but the sequence must not be substantively shared by GAPDH in humans.

TABLE 3

Putative GAPDH peptide sequences derived from sepsis-inducing bacteria, for use in vaccine

| Bacteria | Amino acid sequence | SEQ ID NO. |
|---|---|---|
| GBS | AFRRIQNVEGVEVTR | 13 |
| | EVKEGGFEVNGQFVKVSA | 14 |
| | TQTKVQTVDGNQLVK | 15 |
| | HRGGDLRRARAGAA | 16 |
| | VEEVNAAMKAAANDSY | 17 |
| | SQLVRTLEYFAKIAK | 18 |
| E. coli | LRRLLEVKSNIDVV | 19 |
| | PWSVDYTEDSLIVN | 20 |
| | AGEMKTIVYNVNDDTL | 21 |
| | GKKVTAEEVNNALK | 22 |
| | TNNNESFGYTDEEI | 23 |
| | TQTEITAVGDLQLVKTVA | 24 |
| | YGFVTQLIRTLEKFAKL | 25 |
| S. aureus | LTDDDMLAHLLKYDTM | 26 |
| | EVVDGGFRVNGKEVKS | 27 |
| | ATGDLKTIVFNTN | 28 |
| | HRKGDKRRARAAA | 29 |
| | QDVTVEQVNEAMKNASNESF | 30 |
| | VEQVNEAMKNASNESF | 31 |
| | TQTRVMSVGDRQLVKVAA | 32 |
| | SYTAQLVRTLAYLAELSK | 33 |
| S. pneumoniae | AFRRIQNVEGVEVTR | 34 |
| | DLTDPVMLAHLLKY | 35 |
| | EVKEGGFEVNGKFIKVSA | 36 |
| | GGNDVKTVVFNTNHDVL | 37 |
| | PHRGGDLRRARAGAA | 38 |
| | NVTVDEVNAAMKAASNESY | 39 |
| | TQTKVLDVDGKQL | 40 |
| | MSYTQALVRTLEYFAKIAK | 41 |
| K. pneumoniae | LRRLLEVDSSLEV | 42 |
| | DLTSPKVLAYLLKH | 43 |
| | PFPWSVDFTEDALIV | 44 |
| | TVYAEKEAQHIPWQA | 45 |
| | AGEMKTIVYNVNDDTLTPDDT | 46 |
| | VSVLEKKVTADEVNQAM | 47 |
| | IIGSHFGSIYDATQ | 48 |
| | LEIVEAGGVQLVKTVA | 49 |
| | YGFVTQLIRVLEKFAR | 50 |

TABLE 3-continued

Putative GAPDH peptide sequences derived from sepsis-inducing bacteria, for use in vaccine

| Bacteria | Amino acid sequence | SEQ ID NO. |
|---|---|---|
| Pseudomonas spp | LRALYTGHYREQLQV | 51 |
| | DLGDAAVNAHLFQ | 52 |
| | GEVEHDAESLRVMGDRIAVSAI | 53 |
| | SAIRNPAELPWKSLGVDI | 54 |
| | VAQVLHRELGIEH | 55 |
| | TIHAYTNDQNLSDVYHPD | 56 |
| | VYHPDLYRARSATQSMIPTK | 57 |
| | VQVARDTSVDEVNRLLRE | 58 |
| | GSPVLGYNTQPLVSV | 59 |
| | ANHTKVSGRLVKAMA | 60 |
| | MLDSALALAAARD | 61 |
| | TGHYREQLQ | 62 |
| MenB | ALRQIEKAHDIEV | 63 |
| | DLTPAEMLLHLFK | 64 |
| | ELKDDAIVVNGKE | 65 |
| | HRKGDLRRARAAAL | 66 |
| | NAAMKAAASESYG | 67 |
| | TQTRVMTVGGKQL | 68 |
| | TCQLVRTLEYFAGKI | 69 |

Hence, in another preferred embodiment, a peptide of the first aspect has an amino acid sequence substantially as set out in any one of SEQ ID NOs: 13-69.

Suitably, a peptide of the first aspect comprises 150 amino acids, or less. For example, the peptide preferably comprises less than 100 amino acids and more preferably less than 50 amino acids. Even more preferably the peptide comprises less than 30 amino acids and most preferably less than 20 amino acids. Suitably, a peptide of the invention comprises at least 3 amino acids. Preferably, a peptide of the invention comprises at least 5 amino acids, more preferably at least 8 amino acids, and even more preferably at least 10 amino acids. The peptides of the invention can be of any length within the above ranges, but they will typically be 5-100 amino acids in length, preferably will be 5-50 amino acids in length and most preferably will be 10-20 amino acids in length.

Suitably, a peptide of the invention should be located at the surface of each bacterial GAPDH and present a 3D structure (conformation) similar to the one they possess within the whole protein.

The peptides of the invention can be obtained by any means known in the art, including through recombinant means. For example, the production of rGAPDH (the whole protein) from GBS has been previously described [41]. Desired peptides can be produced in a similar manner. The recombinant production of GAPDH (whole protein or peptides) in bacteria other than GBS is also contemplated as part of the invention. Alternatively, the peptides can be obtained by protein truncation or synthesised de novo, using techniques well known in the art (such as solid-phase or liquid-phase synthesis). The invention thus extends to nucleic molecules which encode the peptides of the invention.

Hence, according to a second aspect of the invention, there is provided an isolated nucleic acid encoding a peptide according to the first aspect, or a functional fragment or functional variant thereof.

An experienced investigator in the field would readily be able to identify suitable nucleic acid sequences that encode a peptide according to the first aspect, or a functional fragment or functional variant thereof. The skilled person would hence be readily able to execute this aspect of the invention, based upon the existing knowledge in the art and/or relevant technical details provided in the published literature (see, for example, [25], which describes a useful method for constructing and purifying recombinant GAPH).

In an embodiment, the isolated nucleic acid is recombinant or synthetic. In an embodiment, the isolated nucleic acid is a cDNA molecule encoding a peptide according to the first aspect, or a functional fragment or functional variant thereof. In an embodiment, the isolated nucleic acid is chemically modified, for example, via the inclusion of a known modified nucleotide. In an embodiment, the isolated nucleic acid is operably linked to a heterologous promoter. In an embodiment, the isolated nucleic acid is bound to a substrate or label or such like. Such modifications are usual in the art and will be known to the skilled person.

In a third aspect, there is provided a genetic construct comprising a nucleic acid according to the second aspect.

Genetic constructs of the invention may be in the form of an expression cassette, which may be suitable for expression of the encoded peptide in a host cell. The genetic construct may be introduced into a host cell without it being incorporated in a vector. For instance, the genetic construct, which may be a nucleic acid molecule, may be incorporated within a liposome or a virus particle. Alternatively, a purified nucleic acid molecule (for example, histone-free DNA or naked DNA) may be inserted directly into a host cell by suitable means, for example, direct endocytotic uptake. The genetic construct may be introduced directly into cells of a host subject (for example, a bacterial cell) by transfection, infection, electroporation, microinjection, cell fusion, protoplast fusion or ballistic bombardment. Alternatively, genetic constructs of the invention may be introduced directly into a host cell using a particle gun. Alternatively, the genetic construct may be harboured within a recombinant vector, for expression in a suitable host cell.

Hence, in a fourth aspect of the invention, there is provided a recombinant vector comprising a genetic construct according to the third aspect.

The recombinant vector may be a plasmid, cosmid or phage. Such recombinant vectors are useful for transforming host cells with the genetic construct of the fifth aspect, and for replicating the expression cassette therein. The skilled technician will appreciate that genetic constructs of the invention may be combined with many types of backbone vector for expression purposes. Recombinant vectors may include a variety of other functional elements including a suitable promoter to initiate gene expression. For instance, the recombinant vector may be designed such that it autonomously replicates in the cytosol of the host cell. In this case, elements which induce or regulate DNA replication may be required in the recombinant vector. Alternatively, the recombinant vector may be designed such that it integrates into the genome of a host cell. DNA sequences which favour targeted integration (for example, by homologous recombination) may be used.

The recombinant vector may also comprise DNA coding for a gene that may be used as a selectable marker in the cloning process, i.e. to enable selection of cells that have been transfected or transformed, and to enable the selection of cells harbouring vectors incorporating heterologous DNA. For example, chloramphenicol resistance is envisaged. Alternatively, the selectable marker gene may be in a different vector to be used simultaneously with vector containing the gene of interest. The vector may also comprise DNA involved with regulating expression of the coding sequence, or for targeting the expressed peptide to a certain part of the host cell.

Accordingly, in an fifth aspect, there is provided a host cell comprising a genetic construct according to the third aspect, or a recombinant vector according to the fourth aspect.

The host cell may be a bacterial cell, for example *E. coli*. Alternatively, the host cell may be an animal cell, for example a mouse or rat cell. It is preferred that the host cell is not a human cell. The host cell may be transformed with genetic constructs or vectors according to the invention, using known techniques. Suitable means for introducing the genetic construct into the host cell will depend on the type of cell.

In a sixth aspect, there is provided a transgenic host organism comprising at least one host cell according to the fifth aspect.

The genome of the host cell or the transgenic host organism of the invention may comprise a nucleic acid sequence encoding a peptide, variant or fragment according to the first aspect. The host organism may be a multicellular organism, which is preferably non-human. For example, the host organism may be a mouse or rat. The host may be a bacterium. The host may be used for development of a vaccine for immunising a subject against infections with sepsis-inducing bacteria, such as GBS, *E. coli, Staphylococcus* spp., *S. pneumoniae, K. pneumoniae, N. meningitidis* and/or *Pseudomonas* spp. Indeed, knowledge of the amino acid sequences of GAPDH from the different sepsis-inducing bacteria, as described herein, can be harnessed in the development of a vaccine.

As described herein, the inventors were surprised to find that GAPDH is an extracellular virulence factor of the most harmful bacteria associated with neonatal sepsis and also sepsis in the elderly and diabetics. The inventors have surprisingly revealed that bacterial GAPDH induces, in the host, a production of IL-10 very early upon infection, and that these pathogens are using GAPDH secretion as a form of escape from the host immune system (see Examples 5 and 6).

The inventors have also surprisingly discovered that GAPDH acts on immune cells through interaction with Toll-like receptor 2 (TLR2). Interestingly, the inventors have found that bacterial GAPDH is able to engage TLR2 on the surface of B1 lymphocytes and induce IL-10 production by these cells (see Examples 1 and 2). The inventors have discovered that B1 cells are the major producers of IL-10 upon GAPDH stimulus.

While the inventors were aware from their previous work that TLR2-mediated IL-10 production plays a key role in the pathophysiology of neonatal sepsis caused by GBS [42], it was surprising that this activity is triggered by GAPDH. According to the literature [43,44], it was expected that TLR2 recognise bacterial-associated lipoproteins. The inventors had thus always assumed that TLR2-mediated IL-10 production was associated with a GBS lipoprotein. Hence, it was surprising to discover that bacterial GAPDH could also bind to TLR2 and be responsible for the signaling cascade that induces IL-10 production. Given the aforementioned surprising finding that GAPDH is a shared virulence factor, it was also completely surprising that this activity is shared by sepsis-inducing bacteria other than GBS (see Example 3).

Other leukocytes, like macrophages, have been found to also produce IL-10 upon bacterial GAPDH recognition, although to a lesser extent than B1 cells. In addition, the inventors have surprisingly discovered that GAPDH-induced (i.e. TLR2-mediated) IL-10 production by B1 cells is significantly augmented in the presence of type I interferon produced by dendritic cells or macrophages, which occurs after recognition of bacterial antigens by these cells (see Example 4). This represents a completely novel virulence mechanism, where bacterial structural antigens and a secreted product act synergistically to induce host immunosuppression.

The inventors have also discovered that the tendency of newborns to produce elevated amounts of IL-10 in the presence of bacterial GAPDH is the reason for their increased susceptibility to these infections; whilst this was known for GBS [24], it was not known or expected for other sepsis-inducing bacteria (see Example 5). Immunocompromised adults such as the elderly and diabetics are also protected from sepsis by the neutralisation of bacterial GAPDH, meaning that the same mechanism observed in the neonates is true for these groups too (see Examples 12 and 13). Moreover, the inventors have found that bacterial GAPDH is also a potent inducer of IL-10 in human cordblood and adult leukocytes, proving that the same mechanism observed in mice is translated into human individuals (see Example 6).

As the inventors have studied the main sepsis-inducing bacteria in their work, they hypothesise that the same results would be observed in any other sepsis-inducing bacteria. Taking this into account, the inventors have developed a GAPDH-based vaccine to prevent infectious diseases caused by sepsis-inducing bacteria in immunocompromised hosts such as neonates, babies, children, women of fertile age, pregnant women, foetuses, the elderly and diabetics, in particular.

Therefore, according to a seventh aspect of the invention, there is provided the use of a peptide, fragment or variant according to the first aspect, in the development of a vaccine for preventing an infection with sepsis-inducing bacteria.

The sepsis-inducing bacteria may preferably be selected from a group of bacteria consisting of GBS, *E. coli*, *Staphylococcus* spp., *S. pneumoniae*, *K. pneumoniae*, *Pseudomonas* spp. and *N. meningitidis*. In an embodiment, the *Staphylococcus* spp. is *S. aureus*. In another embodiment, the *Pseudomonas* spp. is *P. aeruginosa*. In another embodiment, the *N. meningitidis* is MenB. In an embodiment, the sepsis-inducing bacteria are not GBS.

In an eighth aspect, there is provided a vaccine comprising a peptide, fragment or variant according to the first aspect.

Since GAPDH is a protein which is also present in humans, a vaccine constituted with the whole bacterial GAPDH protein could raise autoimmune pathologies. Advantageously, and as exemplified in Examples 8-10, when a peptide of the first aspect is used as a vaccine, it results in a strong antibody response to GAPDH from any of the sepsis-inducing bacteria described here, while concomitantly avoiding autoimmune pathologies. In fact, the use of such a peptide is believed to increase the specificity of the vaccine against each of the bacterial GAPDHs, which, in turn, increases the protection afforded against each of the bacteria. As described above (see the sequence comparison in Table 1, in some cases, the degree of sequence similarity between GAPDHs from different bacteria is not that high. By using different peptides, a specific immune response towards any of the bacterial GAPDHs can hence be assured. This would not be possible using a single GAPDH (whole protein) as a vaccine. Surprisingly, therefore, the inventors have found a way in which a GAPDH-derived vaccine can be administered to subjects in need thereof, without causing autoimmune pathologies. With respect to neonates in particular, neonatal B1 cells represent approximately 30% of total spleen cells in neonates. On the other hand, adult B1 cells correspond to 1-5% of total spleen cells [45]. This is believed by the inventors to reinforce the role of bacterial GAPDH in neonatal susceptibility to sepsis.

A vaccine of the eighth aspect (or as developed in the seventh aspect) may comprise any of the different peptides described or envisaged herein, or fragments or variants thereof, in any combination and in any number. In a preferred embodiment therefore, the vaccine may comprise just one type of peptide described herein (for example, SEQ ID NO: 9). In another embodiment, the vaccine may comprise any two (for example, SEQ ID NOs: 9 and 10), three (for example, SEQ ID NOs: 9, 10 and 11), four, five, six, seven, eight, nine, ten or more of the peptides, or fragments or variants thereof, described or envisaged herein, and so on. Any combination of the different peptides, or fragments or variants thereof, are envisaged and form part of the invention.

In one preferred embodiment, the vaccine comprises one or more of the peptides shown in Table 2 (i.e. having SEQ ID NOs: 9-12), or fragments or variants thereof. The vaccine may comprise any one peptide, any two peptides, any three peptides or indeed all four of the peptides, or fragments or variants thereof.

In another preferred embodiment, the vaccine comprises one or more of the peptides shown in Table 3 (i.e. having SEQ ID NOs: 13-69), or fragments or variants thereof. Hence, the vaccine may comprise any one of the peptides, or any two, three, four, five, six, seven, eight, nine, ten or more of the peptides, or fragments or variants thereof.

In yet another preferred embodiment, the vaccine comprises one or more of the peptides shown in Table 2 (i.e. having SEQ ID NOs: 9-12) and one or more of the peptides shown in Table 3 (i.e. having SEQ ID NOs: 13-69), or fragments or variants thereof. The vaccine may comprise any one of the peptides, or any two, three, four, five, six, seven, eight, nine, ten or more of the peptides, or fragments or variants thereof.

In a most preferred embodiment, the vaccine contains all four of the peptides shown in Table 2 (i.e. having SEQ ID NOs: 9-12), or fragments or variants thereof. Purely for convenience, and not to be construed as limiting in any way, the vaccine containing the combination of these four peptides will hereinafter be referred to as Neonatal Vaccine. Although its name refers to neonates in particular, Neonatal Vaccine is intended for use in any of the patient populations described herein and against any of the diseases, so disorders or conditions described herein. In this regard, pre-term births and stillbirths can be caused by an exacerbated inflammatory response induced by bacterial infections. In the cases of bacterial-induced pre-term births and stillbirths, the most common agents are GBS, *E. coli* and *K. pneumoniae*, i.e. the sepsis-inducing bacteria described herein.

In a vaccine as described herein, the peptides, fragments or variants thereof may be linked together to form a larger peptide (or small protein). In one embodiment, two or more different peptides (or fragments or variants) are linked together. In another embodiment, two or more copies of the same peptide (or fragment or variant) are linked together. Linkage may be direct (i.e. having no amino acids in-between the peptides, fragments or variants being linked) or indirect (i.e. having one or more amino acids between the peptides, fragments or variants being linked, so serving as a 'spacer'). A pattern of one or more of the described peptides (or fragments or variants) may be repeated to form the larger peptide/small protein. The repetitions may be directly adjacent to each other, in a so-called tandem repeat, or they may be spaced apart by one or more amino acids in each case. Alternatively the linked peptides, fragments or variants may appear in a random order. Any and all combinations of the above arrangements are also envisaged and form part of the invention. For example, a larger peptide may be formed by linking two or more copies of the same peptide, fragment or variant and two or more different peptides, fragments or variants together, in a pattern, a random order or in a combination of both.

Thus, in a preferred embodiment, the vaccine may comprise just one type of peptide, fragment or variant described herein (for example, SEQ ID NO: 9), but in two or more linked copies of that type. In another embodiment, the vaccine may comprise any two (for example, SEQ ID NOs: 9 and 10), three (for example, SEQ ID NOs: 9, 10 and 11), four, five, six, seven, eight, nine, ten or more linked copies of the described peptides, fragments or variants, in any of the arrangements described immediately above.

In one preferred embodiment, the vaccine comprises one or more linked copies of the peptides shown in Table 2 (i.e. having SEQ ID NOs: 9-12), or fragments or variants thereof. The vaccine may comprise any one peptide, any two peptides, any three peptides or indeed all four of the peptides, or fragments or variants thereof, in any linkage arrangement as described herein.

In another preferred embodiment, the vaccine comprises one or more linked copies of the peptides shown in Table 3 (i.e. having SEQ ID NOs: 13-69), or fragments or variants thereof. Hence, the vaccine may comprise any one of the peptides, or any two, three, four, five, six, seven, eight, nine, ten or more of the peptides, or fragments or variants thereof, in any linkage arrangement as described herein.

In yet another preferred embodiment, the vaccine comprises one or more of the peptides shown in Table 2 (i.e. having SEQ ID NOs: 9-12) and one or more of the peptides shown in Table 3 (i.e. having SEQ ID NOs: 13-69), or fragments or variants thereof, in any linkage arrangement as described herein. The vaccine may comprise any one of the peptides, or any two, three, four, five, six, seven, eight, nine, ten or more of the peptides, or fragments or variants thereof, in any linkage arrangement as described herein.

In a most preferred embodiment, the vaccine is Neonatal Vaccine, i.e. containing all four of the peptides shown in Table 2 (i.e. having SEQ ID NOs: 9-12), or fragments or variants thereof, in any linkage arrangement as described herein.

Thus, a vaccine of the eighth aspect (or as developed in the seventh aspect) may comprise any two, three, four, five, six, seven, eight, nine, ten or more peptides, fragments or variants of the first aspect, wherein at least two of the peptides, fragments and/or variants are linked together. Any two, three, four, five, six, seven, eight, nine, ten or more of the peptides, fragments or variants may be linked together in this respect.

The inventors were surprised to observe that the peptides derived from GAPDH of sepsis-inducing bacteria, and vaccines comprising these peptides, are able to elicit a protective antibody response. In particular, the antibodies raised against the peptides are able to specifically recognise, and neutralise, GAPDH of sepsis-inducing bacteria.

Accordingly, in a ninth aspect, there is provided the use of a peptide, fragment or variant according to the first aspect, or a vaccine according to the eighth aspect, for stimulating an immune response.

Preferably, the immune response includes the production of antibodies that are specific to GAPDH of one or more species of sepsis-inducing bacteria. The sepsis-inducing bacteria may be GBS, *E. coli*, *Staphylococcus* spp., *S. pneumoniae*, *K. pneumoniae*, *N. meningitidis* and/or *Pseudomonas* spp. In an embodiment, the *Staphylococcus* spp. is *S. aureus*. In another embodiment, the *Pseudomonas* spp. is *P. aeruginosa*. In another embodiment, the *N. meningitidis* is MenB. Thus, the GAPDHs for which the antibodies have specificity may be those having the amino acid sequences provided as SEQ ID NOs: 1-7. In an embodiment, the sepsis-inducing bacteria are not GBS.

As GAPDH is a ubiquitous protein and, as demonstrated herein, conserved amongst the sepsis-inducing bacteria, the peptides, fragments and variants of the invention are able to induce protection against all of the different serotypes of sepsis-inducing bacteria, which is advantageous.

Previously, glycoconjugate vaccines against nine GBS serotypes have been shown to be immunogenic in animals, but the existence of distinct epitope-specific capsular serotypes prevented the development of a global GBS vaccine [46,47]. In contrast, GAPDH is structurally conserved in all eight published GBS genomes (identity >99.8%). As the inventors have previously described, anti-GAPDH immunoglobulin G (IgG) antibodies purified from sera of GAPDH-immunised mice or rabbits have thus been used to demonstrate the presence of GAPDH in culture supernatants of 10 unrelated GBS clinical isolates belonging to different serotypes and/or MLSTypes [24]. As GBS GAPDH displays only 44.7, 45.8 and 44.0% amino acid identity with rabbit, mice and human GAPDH, respectively, however, the previously described 'GBS vaccine' does not induce any autoimmunity upon administration in mammals [24]. The same is true for the peptides, fragments and variants described herein, given the inventors' present discovery that GAPDH is conserved between all sepsis-inducing bacteria.

The use of the peptide, fragment or variant may be an in vitro, in vivo or ex vivo use.

Preferably, the use of the peptide, fragment or variant thereof is an in vitro or ex vivo use for the production of antibodies. In a particularly preferred embodiment, the in vitro or ex vivo use is for the production of monoclonal or polyclonal antibodies.

Such uses may involve the interaction of a peptide, fragment or variant of the first aspect with antibody-producing cells in vitro or ex vivo, such that antibodies that are specific for GAPDH of one or more species of sepsis-inducing bacteria may be produced. Suitable antibody-producing cells and techniques for contacting the same with the peptides, fragments or variants of the invention in order to produce antibodies are described in the art and will be known to the skilled person. For example, blood products of immune people and/or non-human immune animals may be used to generate the antibodies. Alternatively, the peptides, fragments or variants of the first aspect may be used to produce hybridomas specific for different epitopes of bacterial GAPDH. Standard techniques available in the art could be used to produce the hybridoma.

In another preferred embodiment, the use of the peptide, fragment or variant thereof is an in vivo use, i.e. for stimulating an immune response in a subject.

The peptide, fragment or variant may be administered directly into a subject to be vaccinated on its own, i.e. just one or more isolated peptides having at least 90% amino acid sequence identity with a peptide found within GAPDH of one or more sepsis-inducing bacteria, and having less than 10% amino acid sequence identity with a peptide found within human GAPDH, or a functional fragment or functional variant thereof.

The peptide, fragment or variant may be administered by any means, including by injection or mucosally. Preferably, the peptide, fragment or variant is administered intra-muscularly, sub-cutaneously, intra-venously or intra-dermically. It will be appreciated that administration, into a subject to be vaccinated, of a peptide, fragment or variant of the invention will result in the production of corresponding antibodies exhibiting immunospecificity for the peptide, fragment or variant, and that these antibodies aide in ameliorating or treating an existing infection, and preventing a subsequent infection, with sepsis-inducing bacteria.

In a preferred embodiment, therefore, the peptides, fragments or variants thereof are for stimulating the production of antibodies that are specific to GAPDH of sepsis-inducing bacteria, such as GBS, *E. coli, Staphylococcus* spp., *S. pneumoniae, K. pneumoniae, N. meningitidis* and/or *Pseudomonas* spp.

The skilled person will appreciate that there are various ways in which a vaccine could be made based on the antigenic peptides, fragments and variants described herein, such as the peptides represented as SEQ ID NOs: 9-69, and fragments and variants thereof. For example, genetically engineered vaccines may be constructed where the heterologous antigen (i.e. the peptide, fragment or variant thereof) is fused to a promoter or gene that facilitates expression in a host vector (for example, a bacterium, such as *E. coli*, or a virus such as Adenovirus).

The vaccine may comprise an excipient, which may act as an adjuvant. Thus, in an embodiment, the antigenic peptides, fragments or variants in the vaccine may be combined with a microparticulate adjuvant, for example a liposome or an immune stimulating complex (ISCOM). The peptides, fragments or variants may be combined with an adjuvant, such as cholera toxin, or a squalene-like molecule. Any adjuvant may be used, such as, for example, aluminium hydroxide (alum), tetanus toxoid or diphtheria toxin. A vehicle may suitably be used for the adjuvant, which may include, but is not limited to, water, phosphate buffered saline (PBS), a polyol or a dextrose solution.

The peptides, fragments or variants thereof may also suitably be used in conjunction with a carrier protein, so as to increase the effective size of the peptide, fragment or variant. In this manner the immune system will not only recognise the peptide or fragment or variant thereof, but will have memory to it too. The peptides, fragments or variants thereof may be associated with any carrier protein, such as, for example, hemocyanin from keyhole limpet (KLH).

A vaccine of the invention thus suitably comprises one or more peptides as described herein, or one or more fragments or variants thereof, together with an adjuvant and/or a carrier protein. Any of the described peptides may be used, whether alone or in combination with any of the other described peptides. As described herein, Neonatal Vaccine contains all four of the peptides shown in Table 2 (i.e. having SEQ ID NOs: 9-12), or fragments or variants thereof. However, any combination of the described peptides may instead be used. The adjuvant may be any that is licensed for human use, such as alum, tetanus toxoid (TT) or diphtheria toxin (DT). The carrier protein(s) can be KLH, bovine serum albumin (BSA), ovalbumin (OVA), TT and/or DT. Any other carrier protein suitable for use in humans may also or alternatively be used in the vaccine.

Example 7 describes one way in which a vaccine may be prepared. Firstly, one or more of the peptides, fragments or variants thereof according to the first aspect may be chosen as an antigen against which a subsequently vaccinated subject will produce corresponding antibodies. The sequence of the designated gene or nucleic acid molecule encoding the designated peptide, fragment or variant may then be cloned into a suitable vector to form a genetic construct of the third aspect of the invention, using techniques known in the art.

The DNA sequence encoding the designated antigen may be inserted into any known target gene from the host bacterial cell that encodes a known protein. The DNA sequence encoding the antigen may be inserted into a multiple cloning site. It will be appreciated that insertion into any gene is permissible as long as the growth and function of the host organism is not impaired, i.e. the insertion is functionally redundant.

The thus created genetic construct may be used to transform a vegetative mother cell by double cross-over recombination. Alternatively, the genetic construct may be an integrative vector, which may be used to transform a vegetative mother cell by single cross-over recombination.

The construct may comprise a drug-resistance gene that is selectable in the host cell, for example chloramphenicol resistance. After confirmation of the plasmid clone, the plasmid may then be introduced into a host cell by suitable means. Transformation may be DNA-mediated transformation or by electroporation. Selection may be achieved by testing for drug resistance carried by the plasmid, and now introduced into the genome.

Expression of the hybrid or chimeric gene may be confirmed using Western blotting and probing of size-fractionated proteins (sodium dodecyl sulphate polyacrylamide gel electrophoresis; SDS-PAGE) using antibodies that recognise the introduced antigen (i.e. the peptide, fragment or variant derived from bacterial GAPDH). If the antigenic gene or nucleic acid fused to the host gene is correctly expressed, a new band appears so which is recognised only by the antibody, and not normally found in the host. Other techniques that may be used are immunofluorescence microscopy and fluorescence-activated cell sorting (FACS) analysis that can show surface expression of antigens on the host's surface.

The resultant vaccines may be administered to a subject by any route, including intramuscular, subcutaneous, intradermic, oral, inhalable, intranasal, rectal and intravenous routes. Oral administration may be suitably via a tablet, a capsule or a liquid suspension or emulsion. Alternatively the vaccines may be administered in the form of a fine powder or aerosol via a Dischaler® or Turbohaler®. Intranasal administration may suitably be in the form of a fine powder or aerosol nasal spray or modified Dischaler® or Turbohaler®. Rectal administration may suitably be via a suppository.

A vaccine of the invention is formulated for administration to any subject in need thereof, and particularly an immunocompromised host such as a neonate, baby, child, woman of fertile age, pregnant woman, foetus, an elderly subject or a diabetic. The vaccines need not only be administered to those already showing signs of an infection, or those considered to be immunocompromised or at greater risk of an infection, by sepsis-inducing bacteria. Rather, a vaccine can be administered to apparently healthy subjects as a purely preventative measure against the possibility of such an infection in future. For example, it can be administered as part of a general vaccination programme to immunocompromised hosts such as neonates, babies, children, women of fertile age, pregnant women, foetuses, the elderly and diabetics.

As used herein, "immunocompromised" means having a compromised immune system, as exemplified by neonates, babies, children, women of fertile age, pregnant women, foetuses, the elderly and diabetics.

A vaccine of the invention can be formulated for administration to the indicated subjects at any age. It is intended that it will be administered to children of any age, including neonates, babies, toddlers and children of school age. It is intended that it will be administered to pregnant women and women of fertile age, so as to protect both the mother and foetus from infection. It is also intended that it will be administered to so elderly subjects at any time during their old age, and to diabetics at any point in their lifetime.

The terms 'neonate' and 'newborn', as used herein, can refer to a child from birth to around one month old. The terms apply to premature infants, postmature infants and full term infants. Before birth, the term 'foetus' is used.

The terms 'baby' and 'infant', as used herein, can refer to young children between the ages of around one month and around one or two years of age (i.e. the age when a child learns to walk and talk, when the term 'toddler' may be used instead).

The term 'child', as used herein, refers to young children, covering those from toddlers to around 12 years of age, i.e. the pre-teens.

The term 'elderly', as used herein, refers to subjects of advanced age. For example, it can refer to men and women aged 60 or over, 65 or over, 70 or over, 75 or over, or 80 or over. Non-human subjects in the corresponding later years of life are also encompassed by this term.

The term 'diabetic', as used herein, refers to a person suffering from diabetes mellitus type 1 (also known as juvenile or insulin-dependent diabetes), at any stage of the disease. This is the only type of diabetes that is associated with immune system pathology, rendering the patients immunocompromised.

A vaccine of the invention can be administered simultaneously with other existing vaccines, for example, those recommended for immunocompromised hosts such as babies, children, women of fertile age, pregnant women, the elderly and diabetics (such as, for example, tetanus and diphtheria vaccine).

A vaccine of the invention can be administered to women of fertile age by intramuscular, subcutaneous, intradermic, oral, intranasal or intra-venous route, in particular. A boost for this vaccine is intended in the third trimester of gestation. The vaccine is intended to protect women of fertile age from peri-natal infections caused by sepsis-inducing bacteria including GBS, E. coli, Staphylococcus spp., S. pneumoniae, K. pneumoniae, Pseudomonas spp. and N. meningitidis. Unborn infants (foetuses) benefit from passive immunity acquired when their mothers' antibodies cross the placenta to reach the developing child, especially in the third trimester. As illustrated by the Examples, a vaccine of the invention can also prevent premature births and stillbirths caused by in utero infections due to the ascending of bacteria (such as GBS, E. coli and Klebsiella spp.) from the genital tract into the amniotic fluid.

A suitable dosing regimen may be used depending on the organism to be vaccinated. For example, for a human subject to be vaccinated, normally three doses of 10 mg/kg as a tablet or capsule) at intervals of two months may be used. Blood may be withdrawn for analysis of serum (IgG) responses. Saliva, vaginal fluids or faeces may be taken for analysis of mucosal (secretory IgA) responses. Indirect enzyme-linked immunosorbent assay (ELISA) may be used to analyse antibody responses in serum and mucosal samples, to gauge the efficacy of the vaccination.

As described in the Examples, the inventors have shown that the peptides of the invention are able to induce a protective antibody response toward sepsis-inducing bacteria. The inventors have demonstrated in the Examples that a vaccine of the invention is able to prevent an infection by sepsis-inducing bacteria. Preferably, the vaccine is for preventing a GBS, E. coli, Staphylococcus spp., S. pneumoniae, K. pneumoniae, N. meningitidis and/or Pseudomonas spp. infection. In the development of a vaccine, and as described above, it is preferred that any or all of SEQ ID NOs: 9-69, or fragments or variants thereof, may be used as an antigen for triggering an immune response in a subject which is to be vaccinated. The vaccine is a prophylactic; that is to say, the peptides, fragments or variants described herein may be used to prevent an infection, including preventing a relapse/recolonisation of a previous infection.

Therefore, in a tenth aspect, there is provided a peptide, fragment or variant of the first aspect, for use in therapy.

In an eleventh aspect, the invention provides a peptide, fragment or variant of the first aspect or a vaccine according to the eighth aspect, for use in preventing an infection by sepsis-inducing bacteria.

Furthermore, according to a twelfth aspect of the invention, there is provided a method of preventing an infection by sepsis-inducing bacteria, the method comprising so administering, to a subject in need of such treatment, a peptide, fragment or variant according to the first aspect or a vaccine according to the eighth aspect.

A peptide, fragment, variant or vaccine of the invention can prevent systemic infections caused by one or more of at least seven different pathogens, being the most common causes of sepsis, preferably: GBS, E. coli, Staphylococcus spp., S. pneumoniae, K. pneumoniae, Pseudomonas spp. and N. meningitidis. In an embodiment, the Staphylococcus spp. is S. aureus. In another embodiment, the Pseudomonas spp. is P. aeruginosa. In another embodiment, the N. meningitidis is MenB. In an embodiment, the sepsis-inducing bacteria are not GBS. A peptide, fragment, variant or vaccine of the invention can thus prevent sepsis or any other disease, disorder or condition caused by an infection of sepsis-inducing bacteria. These other diseases, disorders or conditions include pneumonia, meningitis, endocarditis, enterocolitis, urinary tract infections, soft tissue infections, gastrointestinal infections, bloodstream infections and encephalitis.

In a preferred embodiment, a peptide, fragment, variant or vaccine of the invention is used to prevent a premature birth and/or stillbirth. As explained herein, premature births and stillbirths are caused by in utero infections due to the ascending of bacteria (such as GBS, E. coli and Klebsiella spp.) from the genital tract into the amniotic fluid. By vaccinating the expectant mother with a peptide, fragment, variant or vaccine of the invention, passive immunity with antibodies raised against such an antigen is provided in the unborn offspring. Foetuses and neonates can thus be protected against infection through a maternal vaccination.

The inventors have realised that knowledge of GAPDH being secreted by all of the sepsis-inducing bacteria, and in particular, the sequence similarity of these secreted GAPDHs, can also be harnessed in the preparation of useful therapeutic drugs for treating, preventing or ameliorating infections by sepsis-inducing bacteria. For example, any agent which blocks the binding of the secreted GADPH with a target human or animal cell can be used as a medicament to prevent, treat or ameliorate an infection in that target cell.

The agent which is capable of blocking the binding of the secreted GADPH with a human or animal cell may be an antibody. For example, an antibody exhibiting specificity to any of the peptides, fragments or variants described herein, including those having an amino acid sequence set forth in SEQ ID NOs: 9-69, would be capable of blocking binding of the secreted GAPDH to a human or animal cell. For example, if the vaccine is administered mucosally it will generate secretory IgA at the mucosal surface, and the antibody (sIgA) would block binding of the GAPDH to the host cell epithelium. If the vaccine is administered systemically it will induce the production of IgG, which will block the binding of bacterial GAPDH to TLR2 on the surface of B1 cells and prevent early IL-10 production by these cells.

Therefore, according to a thirteenth aspect of the invention, there is provided an antibody that is specific for GAPDH of one or more species of sepsis-inducing bacteria, said antibody being raised against a peptide, fragment or variant of the first aspect.

The term 'specific for', as used herein in connection with antibodies, can mean that the variable regions of the antibodies recognise and bind their targets (e.g. a peptide or polypeptide) exclusively (i.e. able to distinguish the target peptide or polypeptide from other similar peptides or polypeptides despite sequence identity, homology or similarity found in the family of peptides or polypeptides).

As above, the amino acid sequences of the peptides, fragments or variants of the first aspect of the invention may be sequences that are found within a native bacterial GAPDH sequence. Such sequences may therefore represent target epitopes on the bacterial GAPDH, which can be exploited in the blocking of the binding of the secreted GAPDH to a human or animal cell.

Accordingly, in a fourteenth aspect, there is provided an antibody that is specific for an epitope found in GAPDH of one or more species of sepsis-inducing bacteria, wherein the epitope has an amino acid sequence substantially as set out in any one of SEQ ID NOs: 9-69.

The antibodies of the thirteenth and fourteenth aspects are capable of blocking the binding of GAPDH secreted by one or more species of sepsis-inducing bacteria to a human or animal cell. As above, the cell may be an epithelial cell or a B1 cell. Other leukocytes, such as macrophages, are also envisaged. For example, the antibody may be sIgA and capable of blocking the binding of the GAPDH to a human or animal epithelial cell. Alternatively the antibody may be IgG and capable of blocking the binding of the GAPDH to TLR2 on the surface of human or animal leukocytes, such as B1 cells or macrophages. Such antibodies are consequently suitable for blocking or neutralising GAPDH-induced IL-10 production in the human or animal cells. Both monoclonal and polyclonal antibodies are encompassed by the invention.

According to a fifteenth aspect of the invention, there is provided a method of producing antibodies that are specific for GAPDH of one or more species of sepsis-inducing bacteria, the method comprising the step of contacting antibody-producing cells with a peptide, fragment or variant of the first aspect, or a vaccine according to the eighth aspect.

Preferably, the sepsis-inducing bacteria referred to in the above aspects of the invention are GBS, *E. coli, Staphylococcus* spp., *S. pneumoniae, K. pneumoniae, N. meningitidis* and/or *Pseudomonas* spp. In an embodiment, the *Staphylococcus* spp. is *S. aureus*. In another embodiment, the *Pseudomonas* spp. is *P. aeruginosa*. In another embodiment, the *N. meningitidis* is MenB. Thus, the GAPDHs for which the antibodies have specificity, or to which the antibodies bind, may be those having the amino acid sequences identified as SEQ ID NOs: 1-7. In an embodiment, the sepsis-inducing bacteria are not GBS.

The methods of the invention may be in vitro, in vivo or ex vivo methods.

Suitable in vitro and ex vivo methods are those as described in the ninth aspect of the invention, i.e. methods for the production of (monoclonal or polyclonal) antibodies that are specific for GAPDH of one or more species of sepsis-inducing bacteria.

Suitable in vivo methods are those as described in the ninth aspect of the invention, i.e. methods of vaccination.

In a sixteenth aspect, there is provided a method of treating, ameliorating or preventing an infection by sepsis-inducing bacteria, the method comprising administering, to a subject in need of such treatment, an antibody according to the thirteenth or fourteenth aspect or a vaccine according to the eighth aspect.

Preferably, the antibody is capable of treating, ameliorating or preventing an infection with GBS, *E. coli, Staphylococcus* spp., *S. pneumoniae, K. pneumoniae, N. meningitidis* and/or *Pseudomonas* spp. In an embodiment, the *Staphylococcus* spp. is *S. aureus*. In another embodiment, the *Pseudomonas* spp. is *P. aeruginosa*. In another embodiment, the *N. meningitidis* is MenB. Thus, the GAPDHs for which the antibodies have specificity are preferably those having the amino acid sequences provided as SEQ ID NOs: 1-7. In an embodiment, the sepsis-inducing bacteria are not GBS.

An antibody of the invention can thus prevent, treat or ameliorate sepsis or any other disease, disorder or condition caused by an infection of sepsis-inducing bacteria. These other diseases, disorders or conditions include pneumonia, meningitis, endocarditis, enterocolitis, urinary tract infections, soft tissue infections, gastrointestinal infections, bloodstream infections and encephalitis. Antibodies of the thirteenth and fourteenth aspects of the invention, for use in therapy, and particularly for use in preventing, treating or ameliorating an infection by sepsis-inducing bacteria, including preventing, treating or ameliorating the aforementioned diseases, disorders and conditions, are therefore also provided.

Preferably, the antibody is raised against a peptide, fragment or variant as defined in the first aspect of the invention, or a vaccine as defined in the eighth aspect of the invention.

As discussed above in connection with the twelfth aspect of the invention, antibodies raised against a peptide, fragment, variant or vaccine of the invention can pass to an unborn baby across the mother's placenta or in the mother's milk during lactation. Such passive immunity, provided in the unborn offspring, can protect against infection by sepsis-inducing bacteria and, prevent a premature birth and/or stillbirth. In a preferred embodiment, therefore, the method of the sixteenth aspect is a method of preventing infection in an unborn baby and, thus, a method of preventing a premature birth and/or stillbirth. In this embodiment, the antibody would be administered to the expectant mother, as a suitable strategy to substitute intrapartum antibiotic prophylaxis. Antibodies of the thirteenth and fourteenth aspects of the invention, for use in preventing, premature birth and/or stillbirth, are therefore also provided.

As used herein, the term 'antibody' includes not just whole IgG, but portions thereof, so including Fab and F(ab')2 fragments, too. It also includes sIgA.

Thus, in addition to vaccination using a vaccine of the invention, the antibodies elicited with the peptides, fragments, variants or vaccines described herein, whether the whole sIgA or IgG antibody or portions thereof, including Fab or F(ab')2 fragments, can be used as a treatment for infected individuals and/or in mothers that did not receive the vaccine, particularly as follows:

a) A therapeutic approach to be administered in neonates with proven or suspected sepsis or infection by sepsis-inducing bacteria—whole IgG or Fab/F(ab')2 fragments;

b) A preventive approach against infection by sepsis-inducing bacteria, to be administered in neonates born from mothers that did not receive the vaccine—whole IgG or Fab/F(ab')2 fragments;

c) A preventive approach against infection by sepsis-inducing bacteria, to be administered in mothers in the third trimester of vaccination that did not receive the vaccine or in women of fertile age—whole IgG; and d) A therapeutic approach for expectant mothers or women of fertile age with proven sepsis or invasive infections caused by sepsis-inducing bacteria.

Passive administration of anti-GAPDH antibodies constitutes a significant improvement over the current therapeutic approaches based on antibiotic administration, which causes the selection of resistant strains. Passive immunity results when a person is given another subject's antibodies. When these antibodies are introduced into the person's body, the 'loaned' antibodies help prevent or fight certain infectious diseases. The protection offered by passive immunisation is short-lived, usually lasting only a few weeks or months, but it helps protect right away.

As demonstrated herein, passive immunity can be induced artificially when antibodies are given as a medication to a non-immune individual. As above, these antibodies may come from the pooled and purified blood products of immune people or from non-human immune animals, such as horses, sheep and rabbits. As shown in the Examples, passive administration of antibodies to newborn mice confers protection from lethal so infection with GBS, *E. coli*, *S. pneumoniae* and *S. aureus*. These antibodies are to be administered to mothers who were not vaccinated with a vaccine of the invention and/or in newborns from non-vaccinated mothers. As discussed herein, passive immunity can also be induced in foetuses by administration of the peptides, agents, vaccines, antibodies and medicaments of the invention to expectant mothers. Unborn infants (foetuses) benefit from passive immunity acquired when their mothers' antibodies cross the placenta to reach the developing child, especially in the third trimester. This is therefore a suitable strategy to substitute intrapartum antibiotic prophylaxis.

It will be appreciated that peptides, agents, vaccines, antibodies and medicaments according to the invention may be used in a monotherapy (i.e. the sole use of that peptide, agent, vaccine, antibody or medicament), for treating, ameliorating or preventing an infection with sepsis-inducing bacteria. Alternatively, peptides, agents, vaccines, antibodies and medicaments according to the invention may be used as an adjunct to, or in combination with, known therapies for treating, ameliorating, or preventing infections with sepsis-inducing bacteria. For example, the peptide, agent, vaccine, antibody or medicament may be used in combination with known agents for treating with sepsis-inducing bacteria infections. For example, the peptide, agent, vaccine, antibody or medicament may be used in combination with known agents for treating neonatal sepsis caused by fungi or viruses. It can be used in combination with known anti-retroviral agents.

There is no restriction on which peptide, agent, vaccine, antibody or medicament as described herein should be administered to which patient. Rather, it is intended that any of the peptides, agents, vaccines, antibodies and medicaments described herein can be administered to any patient as described herein. It is expressly intended by the inventors, in fact, that each and every combination of peptide, agent, vaccine, antibody or medicament, and indicated patient group, is encompassed by this invention. The invention thus includes each and every possible combination of therapeutic agent and indicated patient group. The use of Neonatal Vaccine in immunocompromised hosts such as neonates, babies, children, women of fertile age, pregnant women, foetuses, the elderly and diabetics is preferred.

The peptides, agents, vaccines, antibodies and medicaments according to the invention so may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given, and preferably enables delivery of the agents across the blood-brain barrier.

Medicaments comprising peptides, agents, vaccines and antibodies of the invention may be used in a number of ways. For instance, oral administration may be required, in which case the agents may be contained within a composition that may, for example, be ingested orally in the form of a tablet, capsule or liquid. Compositions comprising peptides, agents, vaccines, antibodies and medicaments of the invention may be administered by inhalation (for example, intranasally). Compositions may also be formulated for topical use. For instance, creams or ointments may be applied to the skin.

Peptides, agents, vaccines, antibodies and medicaments according to the invention may also be incorporated within a slow- or delayed-release device. Such devices may, for example, be inserted on or under the skin, and the medicament may be released over weeks or even months. The device may be located at least adjacent the treatment site. Such devices may be particularly advantageous when long-term treatment with agents used according to the invention is required and which would normally require frequent administration (for example, at least daily injection).

In a preferred embodiment, peptides, agents, vaccines, antibodies and medicaments according to the invention may be administered to a subject by injection into the blood stream or directly into a site requiring treatment. Injections may be intravenous (bolus or infusion) or subcutaneous (bolus or infusion), or intradermal (bolus or infusion).

It will be appreciated that the amount of the peptide, agent, vaccine, antibody or medicament that is required is determined by its biological activity and bioavailability, which in turn depends on the mode of administration, the physiochemical properties of the peptide, agent, vaccine, antibody and medicament, and whether it is being used as a monotherapy or in a combined therapy. The frequency of administration will also be influenced by the half-life of the agent within the subject being treated. Optimal dosages to be administered may be determined by those skilled in the art, and will vary with the particular agent in use, the strength of the pharmaceutical composition, the mode of administration, and the advancement of the bacterial infection. Additional factors depending on the particular subject being treated will result in a need to adjust dosages, including subject age, weight, gender, diet and time of administration.

Generally, a daily dose of between 0.001 µg/kg of body weight and 10 mg/kg of body weight of peptide, agent, vaccine, antibody or medicament according to the invention may be used for treating, ameliorating, or preventing bacterial infection, depending upon which peptide, agent, vaccine, antibody or medicament is used. More preferably, the daily dose is between 0.01 µg/kg of body weight and 1 mg/kg of body weight, more preferably between 0.1 µg/kg and 100 µg/kg body weight, and most preferably between approximately 0.1 µg/kg and 10 µg/kg body weight.

The peptide, agent, vaccine, antibody or medicament may be administered before, during or after onset of the bacterial infection. Daily doses may be given as a single administration (for example, a single daily injection). Alternatively, the peptide, agent, vaccine, antibody or medicament may require administration twice or more times during a day. As an example, peptides, agents, vaccines, antibodies and medicaments may be administered as two (or more depending upon the severity of the bacterial infection being treated) daily doses of between 0.07 µg and 700 mg (i.e. assuming a body weight of 70 kg). A patient receiving treatment may take a first dose upon waking and then a second dose in the evening (if on a two-dose regime) or at 3—or 4-hourly intervals thereafter. Alternatively, a slow release device may be used to provide optimal doses of peptides, agents, vaccines, antibodies and medicaments according to the invention to a patient without the need to administer repeated doses. Known procedures, such as those conventionally employed by the pharmaceutical industry (for example, in vivo experimentation, clinical trials, etc.), may be used to form specific formulations of the peptides, agents, vaccines, antibodies and medicaments according to the invention and precise therapeutic regimes (such as daily doses of the agents and the frequency of administration).

In a seventeenth aspect of the invention, there is provided a sepsis-inducing bacteria treatment composition comprising an antibody of the thirteenth or fourteenth aspect of the invention, and optionally a pharmaceutically acceptable vehicle.

The term "sepsis-inducing bacteria treatment composition" or "anti-sepsis-inducing bacteria composition" can mean a pharmaceutical formulation used in the therapeutic amelioration, prevention or treatment of sepsis-inducing bacteria infections in a subject.

The invention also provides in a eighteenth aspect, a process for making the composition according to the seventeenth aspect, the process comprising combining a therapeutically effective amount of an antibody of the thirteenth or fourteenth aspect of the invention, with a pharmaceutically acceptable vehicle.

A "therapeutically effective amount" of an agent (for example, an antibody of the invention) is any amount which, when administered to a subject, is the amount of agent that is needed to treat the infection, or produce the desired effect.

For example, the therapeutically effective amount of agent (for example, antibody) used may be from about 0.001 mg to about 1000 mg, and preferably from about 0.01 mg to about 500 mg. It is preferred that the amount of agent is an amount from about 0.1 mg to about 100 mg, and most preferably from about 0.5 mg to about 50 mg. As a guide, the dose of antibody used in the neonatal mice in the Examples described herein was 40 mg/kg.

A "pharmaceutically acceptable vehicle" as referred to herein, is any known compound or combination of known compounds that are known to those skilled in the art to be useful in formulating pharmaceutical compositions.

A "subject", as used herein, may be a vertebrate, mammal or domestic animal. Hence, peptides, agents, vaccines, antibodies and medicaments according to the invention may be used to treat any mammal, for example livestock (for example, a horse), pets, or may be used in other veterinary applications. Most preferably, the subject is a human being.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings or tablet-disintegrating agents. The vehicle may also be an encapsulating material. In powders, the vehicle is a finely divided solid that is in admixture with the finely divided active agents according to the invention. In tablets, the active agent may be mixed with a vehicle having the necessary compression properties in suitable proportions and compacted in the shape and size desired. The powders and tablets preferably contain up to 99% of the active agents. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurised compositions. The active agent according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid vehicles for oral and parenteral administration include water (partially containing additives as above, for example, cellulose derivatives, preferably sodium carboxymethyl cellulose solution), alcohols (including monohydric alcohols and polyhydric alcohols, for example, glycols) and their derivatives, and oils (for example, fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurised compositions can be a halogenated hydrocarbon or other pharmaceutically acceptable propellant.

Liquid pharmaceutical compositions, which are sterile solutions or suspensions, can be utilised by, for example, intramuscular, intrathecal, epidural, intraperitoneal, intravenous and particularly subcutaneous injection. The agent may be prepared as a sterile solid composition that may be dissolved or suspended at the time of administration using sterile water, saline or other appropriate sterile injectable medium.

The agents and compositions of the invention may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The agents used according to the invention can also be administered orally either in liquid or solid composition form.

Compositions suitable for oral administration include solid forms, such as pills, capsules, granules, tablets and powders, and liquid forms, such as solutions, syrups, elixirs and suspensions. Forms useful for parenteral administration include sterile solutions, emulsions and suspensions.

It will be appreciated that the invention extends to any nucleic acid or peptide or variant, derivative or analogue thereof, which comprises substantially the amino acid or nucleic acid sequences of any of the sequences referred to herein, including functional variants or functional fragments thereof. The terms "substantially the amino acid/nucleotide/peptide sequence", "functional variant" and "functional fragment", can be a sequence that has at least 40% sequence identity with the amino acid/nucleotide/peptide sequences of any one of the sequences referred to herein, for example 40% identity with the sequences identified as SEQ ID NOs: 9-69.

Amino acid/nucleotide/peptide sequences with a sequence identity which is greater than 50%, more preferably greater than 65%, 70%, 75%, and still more preferably greater than 80% sequence identity to any of the sequences referred to herein are also envisaged. Preferably, the amino acid/nucleotide/peptide sequence has at least 85% identity with any of the sequences referred to, more preferably at least 90%, 92%, 95%, 97%, 98%, and most preferably at least 99% identity with any of the sequences referred to herein.

The skilled technician will appreciate how to calculate the percentage identity between two amino acid/nucleotide/peptide sequences. In order to calculate the percentage identity between two amino acid/nucleotide/peptide sequences, an alignment of the two sequences must first be prepared, followed by calculation of the sequence identity value. The percentage identity for two sequences may take different values depending on: (i) the method used to align the sequences, for example, ClustalW, BLAST, FASTA, Smith-Waterman (implemented in different programs), or structural alignment from 3D comparison; and (ii) the parameters used by the alignment method, for example, local versus global alignment, the pair-score matrix used (for example, BLOSUM62, PAM250, Gonnet etc.) and gap-penalty, for example, functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length-dependent. Therefore, the shorter a pair of sequences is, the higher the sequence identity one may expect to occur by chance.

Hence, it will be appreciated that the accurate alignment of amino acid or nucleic acid sequences is a complex process. The popular multiple alignment program ClustalW [48,49] is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: END-GAP=-1, and GAPDIST=4. Those skilled in the art will be aware that it may be necessary to vary these and other parameters for optimal sequence alignment.

Preferably, calculation of percentage identities between two amino acid/nucleotide/peptide sequences may then be calculated from such an alignment as (N/T)*100, where N is the number of positions at which the sequences share an identical residue, and T is the total number of positions compared including gaps but excluding overhangs. Hence, a most preferred method for calculating percentage identity between two sequences comprises (i) preparing a sequence alignment using the ClustalW program using a suitable set of parameters, for example, as set out above; and (ii) inserting the values of N and T into the following formula: Sequence Identity=(N/T)*100.

Alternative methods for identifying similar sequences will be known to those skilled in the art. For example, a substantially similar nucleotide sequence will be a sequence which hybridises to a nucleotide sequence encoding a peptide according to the first aspect, or a functional fragment or functional variant thereof, or their complements, under stringent conditions. By stringent conditions is meant that the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar peptide may differ by at least 1, but less than 3, 4, 5, 6, 7, 8, 9 or 10 amino acids from the sequences shown in SEQ ID NOs: 9-69.

Due to the degeneracy of the genetic code, it is clear that any nucleic acid sequence described herein could be varied or changed without substantially affecting the sequence of the peptide, polypeptide or protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence, which are altered by the substitution of different codons that encode an amino acid with a side chain of similar biophysical properties to the amino acid it substitutes, to produce a conservative change. For example, small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will know the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying diagrammatic drawings, in which:

FIG. 1 shows an amino acid sequence alignment for GAPDH of the main sepsis-inducing bacteria, GBS, E. coli, S. aureus, S. pneumoniae, K. pneumoniae, P. aeruginosa and

*N. meningitidis*. The multiple alignment was obtained from the ClustalW2 server, after submitting the amino acid sequences identified herein as SEQ ID NOs: 1-7 (according to the FASTA format of the previously indicated UniProt accession numbers). The resultant % sequence similarities are shown in Table 1.

FIG. 2 provides an example of four surface peptides that can be used in a vaccine of the invention. The table shows the amino acid sequences of the four exemplary peptides, and the respective bacteria that possess each amino acid sequence. Below the table is indicated the surface localisation of the same four peptides in the different bacterial GAPDHs. The peptides are identified herein as Peptides 1-4 (SEQ ID NOs: 9-12), and they are used in combination to form the vaccine identified herein as Neonatal Vaccine.

FIG. 3 shows an alignment of the amino acid sequence of GAPDH from *S. agalactiae* (SEQ ID NO:70), *S. pneumoniae* (SEQ ID NO:4), *S. aureus* (SEQ ID NO:3) and humans (SEQ ID NO:8). The two boxed areas show the sequences from which Peptide 1 (SEQ ID NO:9) and Peptide 2 (SEQ ID NO:71) are derived.

FIGS. 4-6 show that neonatal B1 cells are the major producers of IL-10 upon stimulus by bacterial GAPDH. Panels A and B of FIG. 4 show IL-10 concentration following the stimulation of spleen mononuclear cells (MNC), neutrophils from peripheral blood (PMNC), macrophages (FLM) or dendritic cells (FLDC) derived from the liver and B cells (total), B1 cells and B2 cells purified from the spleen of newborn mice with lipopolysaccharide (LPS), rGAPDH or Roswell Park Memorial Institute (RPMI) so medium alone. FIG. 5 shows IL-10 concentration following the stimulation of B1 cells purified from the spleen of newborn mice with rGAPDH in the presence of a TLR2 inhibitor (OxPAC) or Toll-like receptor 4 (TLR4) inhibitor (CLI095) as shown. Panels A and B of FIG. 6 show IL-10 concentration following the stimulation of total cells and B1 cells, respectively, purified from the spleen of newborn mice with rGAPDH, fixed GBS (GBSf) or RPMI medium alone. Panel C of FIG. 6 shows IL-10 concentration following the stimulation of a co-culture of dendritic cells derived from foetal liver and B1 cells purified from newborn spleen with rGAPDH, GBSf, a monoclonal antibody specific for type I interferon receptor (αIFNAR) or RPMI medium alone. Data depicted in all of the panels for FIGS. 4-6 are mean+SEM of at least two independent experiments.

FIG. 7 shows that TLR2 deficiency improves neonatal survival and confers protection to bacterial sepsis. The survival of newborn mice challenged with *S. aureus* strain NEWMAN (panel A) or *E. coli* strain IHE3034 (panel B) is shown. Both wild-type and TLR2−/− mice were included in the study. Results represent data pooled from at least two independent experiments. The numbers between parentheses represent the number of animals that survived the different infectious challenges versus the total number of infected animals. Statistical differences (P values) between TLR2-deficient pups versus controls are indicated.

FIG. 8 shows that blocking IL-10 signaling protects newborns from bacterial sepsis. The survival of newborn mice challenged with *E. coli* strain IHE3034 (panel A) or *S. aureus* strain NEWMAN (panel B) following an injection of monoclonal antibodies specific for the mouse IL-10 receptor (anti-IL10R) or isotype-matched control antibodies (isotype IgG/control) is shown. Results represent data pooled from three independent experiments. The numbers between parentheses represent the number of animals that survived the different infectious challenges versus the total number of infected animals. Statistical differences (P values) between anti-IL-10R-treated pups versus controls are indicated.

FIG. 9 shows that GAPDH secretion is a shared virulence mechanism. rGAPDH, which was used as a positive control, is shown in lane 1. Lanes 2-6 show an equivalent band for the indicated pathogens (NEM316 being a strain of GBS). The data are representative of five independent experiments.

FIG. 10 shows that antibodies elicited with rGAPDH protect newborn mice from infection by sepsis-inducing bacteria other than GBS. The survival of mice pups challenged with *S. pneumonia* strain Tigr4 (Panel A), *E. coli* strain IHE3034 (Panel B) and *S. aureus* strain NEWMAN (Panel C) following an injection of rGAPDH-induced antibodies (anti-rGAPDH IgG) or control antibodies (Control IgG) is shown. Results represent data pooled from two independent experiments. The numbers between parentheses represent the number of animals that survived the various infectious challenges versus the total number of infected animals. Statistical differences (P values) between immunised versus control groups are indicated.

FIG. 11 shows that bacterial GAPDH induces IL-10 production in human mononuclear cells. Panels A and B show IL-10 concentration following the stimulation of human mononuclear cells separated from cord-blood (panel A) or peripheral blood (panel B) with rGAPDH, a TLR2 inhibitor (TLR2 in) or RPMI medium alone. Data depicted in the figure are mean+SEM of at least two independent experiments.

Figure 12:
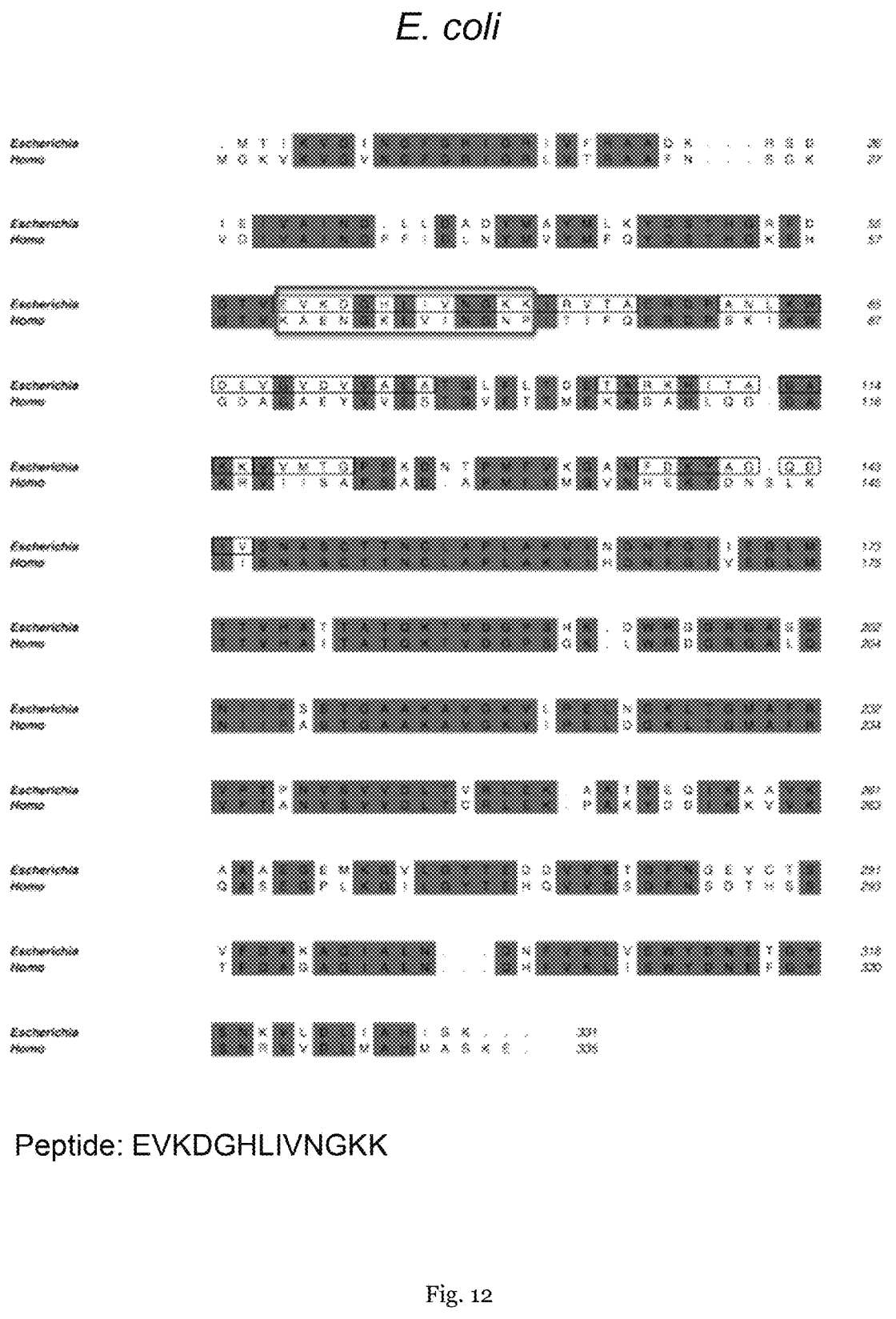

FIG. 12 shows an alignment of the amino acid sequence of GAPDH from *E. coli* (SEQ ID NO:72) and humans (SEQ ID NO:8). The boxed area shows Peptide 3 from FIG. 2. On the bottom right of FIG. 12, Peptide: EVKDGHLIVNGKK (SEQ ID NO:73).

Figure 13:
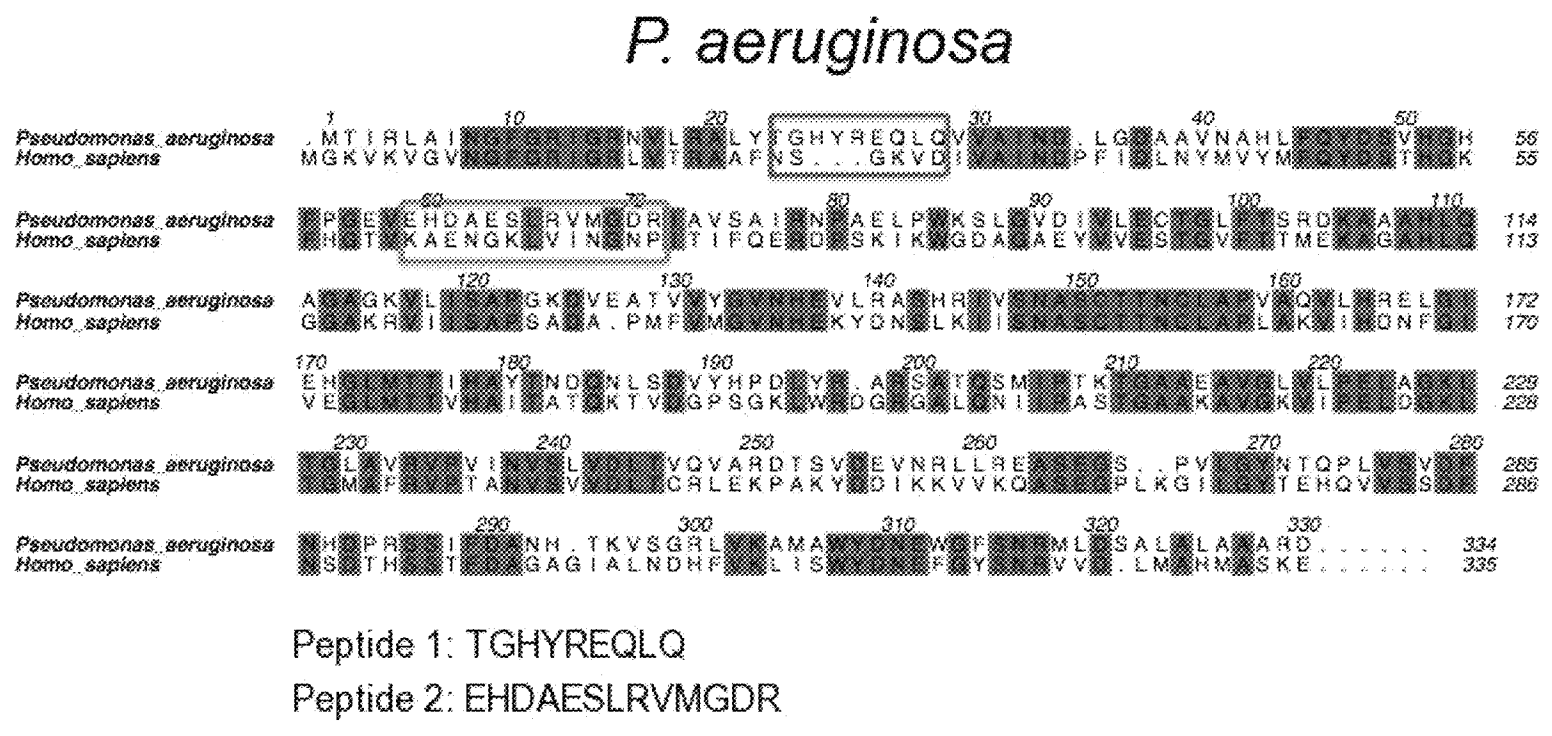

FIG. 13 shows an alignment of the amino acid sequence of GAPDH from *P. aeroginosa* (SEQ ID NO:6) and humans (SEQ ID NO:8). The boxed area at amino acid 23 shows a peptide for use in the invention (SEQ ID NO: 62). The boxed area at amino acid 59 shows Peptide 4 from FIG. 2. On the bottom of FIG. 12, Peptide 1: TGHYREQLQ (SEQ ID NO:62); and Peptide 2: EHDAESLRVMGDR (SEQ ID NO:12).

FIGS. 14, 15 and 16 show that antibodies elicited with a vaccine of the invention react with bacterial GAPDH. rGAPDH, which was used as a positive control, is shown in lane of each gel. Lanes 2-6 in FIG. 14 and lane 2 in FIGS. 15 and 16 show an equivalent band for the indicated pathogens. The data are representative of two independent experiments.

FIG. 17 shows that antibodies elicited with Neonatal Vaccine protect newborn mice from GBS infection. The survival of mice pups challenged with GBS NEM316 following an injection of Neonatal Vaccine-induced antibodies (IgG) or control IgG is shown. Results represent data pooled from two independent experiments. The numbers between parentheses represent the number of animals that survived the infectious challenge versus the total number of infected animals. Statistical differences (P values) between immunised versus control groups are indicated.

FIG. 18 shows that antibodies elicited with Neonatal Vaccine protect newborn mice from bacterial sepsis. The survival of newborn mice challenged with *S. pneumoniae* strain Tigr4 (panel A), *E. coli* strain IHE3034 (panel B) or *S. aureus* strain NEWMAN (panel C) following an injection of Neonatal Vaccine-induced antibodies (IgG) or control IgG is shown. Results represent data pooled from at least two independent experiments. The numbers between parentheses represent the number of animals that survived the different infectious challenges versus the total number of infected animals. Statistical differences (P values) between immunised versus controls are indicated.

FIG. 19 shows that the therapeutic use of anti-GAPDH antibodies can efficiently treat GBS-induced sepsis. The survival of newborn mice challenged with GBS NEM316 and subsequently receiving Neonatal Vaccine-induced antibodies (IgG), control IgG or saline is shown. Results represent data pooled from two independent experiments. The numbers between parentheses represent the number of animals that survived the infectious challenge versus the total number of infected animals. Statistical differences (P values) between immunised versus controls are indicated.

FIG. 20 shows that antibodies elicited with Neonatal Vaccine protect old mice against lethal GBS infection. The survival of old mice challenged with GBS following an injection of Neonatal Vaccine-induced antibodies (Neonatal Vaccine-IgG) or control IgG ('sham-immunized') is shown. Results represent data pooled from two independent experiments. The numbers between parentheses represent the number of animals that survived the infectious challenge versus the total number of infected animals. The statistical difference (P value) between immunised versus control groups is indicated.

FIG. 21 shows that antibodies elicited with Neonatal Vaccine protect non-obese diabetic (NOD) mice against lethal GBS infection. The survival of NOD mice challenged with GBS following injections of Neonatal Vaccine-induced antibodies (Neonatal Vaccine-IgG) or control IgG ('sham-immunized') is shown. Results represent data pooled from two independent experiments. The numbers between parentheses represent the number of animals that survived the infectious challenge versus the total number of infected animals. The statistical difference (P value) between immunised versus control groups is indicated.

EXAMPLES

The materials and methods employed in the studies described in the Examples were as follows, unless where otherwise indicated:

Mice

Six- to eight-week-old male and female BALB/c, C57BL/6, and TLR2-deficient C57BL/B6.129-Tlr2$^{tm1Lir/J}$ (TLR2$^{-/-}$) mice, and old C57Bl/6 mice (over 16 months), were purchased from The Jackson Laboratory. New Zealand White rabbits and eight-week-old non-obese diabetic (NOD) mice were purchased from Charles River Laboratories. Animals were kept at the animal facilities of the Institute Abel Salazar during the time of the experiments. All procedures were performed according to the European Convention for the Protection of Vertebrate Animals used for Experimental and Other Scientific Purposes (ETS 123) and 86/609/EEC Directive and Portuguese rules (DL 129/92). All animal experiments were planned to minimise animal suffering.

Bacteria

The bacteria used in the studies are listed in Table 4 below. All strains were clinical isolates obtained from infected newborns. E. coli, S. aureus, P. aeruginosa, GBS and S. pneumoniae were kindly provided by Professor Patrick Trieu Cuot from Pasteur Institute, Paris, France; K. pneumoniae and N. meningitidis were provided by the Microbiology Department of Hospital Geral de Santo António, Porto, Portugal. GBS and S. pneumoniae were grown in Todd-Hewitt broth or agar (Difco Laboratories) containing 0.001 mg/mL of colistin sulphate and 0.5 µg/mL of oxalinic acid (Streptococcus Selective Supplement, Oxoid). E. coli, P. aeruginosa, MenB and S. aureus were cultured on Todd-Hewitt broth or agar medium. Bacteria were grown at 37° C.

TABLE 4

Bacteria used in the studies described in the Examples

| Bacteria | Strain |
| --- | --- |
| Escherichia coli | IHE$_{3034}$ |
| Staphylococcus aureus | NEWMAN |
| Pseudomonas aeroginosa | PAO$_4$ |
| Streptococcus agalactiae, GBS | NEM$_{316}$ |
| Streptococcus pneumoniae | Tigr$_4$ |
| Neisseria meningitidis | Serogroup B (MenB) |

Antibody Treatments

Antibody treatments were performed in newborn BALB/c mice (up to 48 h old) 12 h prior to GBS infection, and in old C57Bl/6 mice (over 16 months) and NOD mice 24 h prior to GBS infection. For passive immunisations, pups were intraperitoneally injected with 100 µg of anti-rGAPDH IgG antibodies. Control animals received the same amount of control IgG antibodies. For IL-10 signaling blocking, 100 µg of anti-IL10R antibodies (1B1.3a, Schering-Plough Corporation) were administered intraperitoneally and control animals received the same amount of matched isotype control antibody. Regarding the therapeutic use of anti-GAPDH antibodies, mice pups were treated with 100 µg of anti-GAPDH IgG (or the respective control IgG) 6 h after infection.

Neonatal Mouse Model of Bacterial Infection

Neonatal (48 h old), BALB/c, C57BL/6 wild-type or TLR2$^{-/-}$ mice were infected subcutaneously with the indicated inoculum of the bacteria in a maximum volume of 40 µl. Newborns were kept with their mothers during the entire time of the experiment. Survival curves were determined over a 12-day experimental period.

rGAPDH rGAPDH was produced and purified as previously described [41].

Purification of Anti-GAPDH IgG

Adult mice or rabbits were immunised twice with 25 µg of rGAPDH in a PBS/alum suspension with a three-week interval between doses. Sera were collected 10 days after the second immunisation. Pooled serum samples were applied to a Protein G HP affinity column (HiTrap, GE Healthcare Bio-Sciences AB) and purified IgG antibodies so were then passed through an affinity column with immobilised rGAPDH (Hi-trap NHS-activated HP, GE Health-care Bio-Sciences AB). Control IgGs were obtained from sera of mice or rabbits sham-immunised with a PBS/alum suspension and purified on a Protein G HP affinity column. Purified IgG antibody fractions were further equilibrated in PBS and stored at −80° C. in frozen aliquots.

Spleen Total Cell Cultures

Cells from the spleen of newborn mice (up to 48 h old) were obtained by gently teasing the organ in RPMI 1640 supplemented with penicillin (100 IU/ml), streptomycin (50 µg/ml), 2-ME (0.05 M), and 10% foetal bovine serum (FBS) (Sigma-Aldrich)-complete RPMI (cRPMI). Cells were then distributed in 96-well plates (1×10$^6$ cells/well) and cultured for 12 h at 37° C. in a humidified atmosphere containing 5% carbon dioxide, with the medium alone, medium containing 2.5 µg/ml LPS, medium containing 25 µg/ml of rGAPDH, medium containing 1 µg/mL of the TLR2 agonist, PAM3CSK4 (Invivogen). For the experiments with the TLR inhibitors, OxPAC (TLR2 inhibitor) and CLI095 (TLR4 inhibitor) (both from Invivogen) were used at a concentration of 10 μg/mL.

B Cell Purification

B cells were purified from the spleen of neonatal mice (prepared as mentioned above) by magnetic cell sorting using a Mouse B cell Purification Kit (Miltenyi Biotech) according to manufacturer's instructions.

CD5+ B Cell Purification

B1 cells were purified from the spleen of neonatal mice (prepared as mentioned above) by magnetic cell sorting, using a Mouse B1 cell Purification Kit (Miltenyi Biotech) according to manufacturer's instructions.

Neonatal Liver-Derived Macrophages Macrophages were obtained from the liver of one-day old mice. Livers were removed under aseptic conditions and homogenised in Hanks' balanced salt solution (HBSS).

The resulting cell suspension was centrifuged at 500×g and resuspended in cRPMI supplemented with 10% L929 cell conditioned medium. To remove fibroblasts or differentiated macrophages, cells were cultured, on cell culture dishes, overnight at 37° C. in a 5% carbon dioxide atmosphere. Then, non-adherent cells were collected with warm cRPMI, centrifuged at 500×g, distributed in 96-well plates at a density of $1 \times 10^5$ cells/well, and incubated at 37° C. in a 5% carbon dioxide atmosphere. Four days after seeding, 10% of L929 cell conditioned medium was added, and the medium was renewed on the seventh day. After 10 days in culture, cells were completely differentiated into macrophages. This method allows for the differentiation of a homogenous primary culture of macrophages that retain the morphological, physiological and surface markers characteristics of these phagocytic cells [50].

Neonatal liver-derived dendritic cells Dendritic cells were obtained from the liver of one-day old mice. Livers were removed under aseptic conditions and homogenised in HBSS. The resulting cell suspension was centrifuged at 500×g and resuspended in cRPMI supplemented with 30 ng/ml of granulocyte macrophage colony-stimulating factor (GM-CSF) (Immunotools) (Primary DC media). To remove fibroblasts or differentiated macrophages, cells were cultured, on cell culture dishes, overnight at 37° C. in a 5% carbon dioxide atmosphere. At day 3, 75% of the medium (along with non-adherent cells) was removed, and Primary DC media was added. At day 6, cells were removed from the plate by gently pipetting media up and down against the bottom of the plate to gently dislodge non-adherent cells. After several minutes of this, the cell mixture was transferred to 50 mL polystyrene tubes. Cells were then centrifuged at 500×g for 5-7 min and re-suspended in Primary DC media. The cells were counted and plated at a concentration of $5 \times 10^5$ cells/well. For the co-culture experiments, $5 \times 10^4$ dendritic cells were plated per well.

In the co-culture experiments, and where indicated, 20 μg/mL of a monoclonal antibody specific for Type I interferon receptor (anti-IFNAR) (Biolegend) was used.

Purification of Blood Neutrophils

For neutrophil isolation, blood was collected from retroorbital bleeding of neonatal mice (up to 48 h old) and diluted 1:2 in HBSS containing BSA (0.1% w/v) and glucose (1% w/v). Cells were pelleted, and erythrocytes were removed by hypotonic lysis. The blood preparation was suspended in Dulbecco's PBS (GIBCO), layered on a three-layer Percoll (GE-Healthcare) gradient (80, 65, and 55% in Dulbecco's PBS), and centrifuged at 1200×g for 30 min at 10° C. Mature neutrophils were recovered at the interface of the 65 and 80% fractions, and purity was 85%, as determined by FACS analysis, using anti-Ly6G antibodies (Biolegend). Isolated neutrophils were plated on 96-well plates and stimulated for 12 h as indicated.

IL-10 Quantification

IL-10 from newborn or adult cell cultures was quantified by ELISA (R&D Systems), according to the manufacturer's instructions.

Human Blood Samples

Human blood samples were obtained at Hospital Geral de Santo António after informed approval. For the isolation of mononuclear cells, 5 ml aliquots of total blood diluted 1:2 in RPMI 1640 were layered on 2.5 ml of Histopaque (Sigma-Aldrich) and centrifuged at 1000 g for 20 min at room temperature. The cells were then gently removed from the medium-Histopaque interface, transferred to a sterile container, and washed in 10 ml of cRPMI. The isolated mononuclear cells were re-suspended in cRPMI, plated at a concentration of $5 \times 10^5$ cells/well and stimulated with 25 μg/mL of rGAPDH, with 10 μg/mL of OxPAC or with medium alone (RPMI) for 12 h at 37° C. with 5% carbon dioxide.

Neonatal Vaccine

Peptides 1-4 (SEQ ID NOs: 9-12) were conjugated with KLH or OVA as carrier proteins. For the immunisation protocols, 20 μg of each peptide conjugated with the carrier protein was injected intraperitoneally in female BALB/c mice. Alum was used as adjuvant in a 1:20 PBS suspension. Adult female BALB/c mice were immunised three times with a three-week interval between doses. 10 days after the last immunisation, blood was collected and the "Neonatal Vaccine" anti-serum was obtained after blood clotting at 4° C. for 24 hours.

The same immunisation protocol was used in rats for the *N. meningitidis* work (Example 8).

Example 1—a Sub-Population of Neonatal B Cells is Responsible for IL-10 Production Upon Bacterial GAPDH Stimulus Previous published information revealed the role of GAPDH in disabling the neonatal so immune system to combat GBS infections [24]. Although a role for IL-10 was already unveiled in the mechanism of GAPDH-induced immunosuppression, the cellular mechanism remained unknown. In order to uncover which cellular population(s) was contributing to early IL-10 production observed in neonatal GBS infections, different leukocyte populations were purified from neonatal mice and treated in vitro with rGAPDH from GBS.

Materials and Methods

Specifically, and as described above, dendritic cells and macrophages were obtained from neonatal liver precursors, B cells and mononuclear cells were obtained from neonatal spleens and neutrophils were purified from neonatal peripheral blood. A more refined separation of B cells obtained from neonatal spleen, based on surface expression of CD5, allowed the separation of B1 (CD5+) cells.

The different leukocyte populations were stimulated in vitro with 0.5 μg/mL of LPS (as a positive control; LPS is a structural microbial antigen known to induce polyclonal B cell activation), 25 μg/mL of rGAPDH or RPMI medium alone (as a negative control) for 12 h at 37° C. with 5% carbon dioxide. In all conditions $5 \times 10^5$ cells/well were used, except for the separated B cell study, where $2.5 \times 10^5$ cells/well were used.

After incubation of the cells, IL-10 concentration was measured in the supernatants as described above.

At least two independent experiments were performed in each case.

Results

As observed in FIG. 4A, when comparing the ability of mononuclear cells, neutrophils, macrophages, dendritic cells and total B cells to produce IL-10 upon GAPDH stimulus, only B cells retained the ability to produce significant amounts of IL-10.

Following the separation of neonatal B cells, the inventors observed that B1 cells retained the ability to produce IL-10 while B2 cells produced only traceable amounts of this cytokine (FIG. 4B).

Discussion

This study indicates that neonatal B1 cells are the main source of IL-10 upon bacterial GAPDH stimulus.

Example 2—TLR2 is the Surface Receptor for Bacterial GAPDH

In order to establish the cellular receptor responsible for bacterial GAPDH recognition and induction of IL-10 expression, the inventors compared the ability of GAPDH to induce IL-10 production in cultures of purified B1 cells in the presence of specific inhibitors of different pattern recognition receptors.

Materials and Methods

B1 cells were purified from the spleen of newborn mice as described above.

$2.5 \times 10^5$ B1 cells/well were stimulated in vitro with 25 µg/mL of rGAPDH in the presence of 10 µg/ml of TLR2 or TLR4 inhibitors for 12 h at 37° C. with 5% carbon dioxide. The TLR2 and TLR4 inhibitors used were OxPAC and CLI095, respectively.

After incubation of the cells, IL-10 was quantified in the supernatants as described above.

At least two independent experiments were performed.

Results

The inventors found that GAPDH-induced IL-10 production was completely abrogated in the presence of a TLR2 inhibitor (FIG. 5).

Discussion

This result indicates that bacterial GAPDH acts on B1 cells through TLR2 in order to induce IL-10 production.

Example 3—TLR2 Deficiency Improves Neonatal Survival and Confers Protection to Bacterial Sepsis This study aimed to confirm the importance of TLR2 as a receptor for GAPDH, and a cause for neonatal susceptibility to sepsis.

Materials and Methods 48 hours after birth, newborn wild-type and TLR2$^{-/-}$ mice were infected subcutaneously with $5 \times 10^5$ CFU of *S. aureus* strain NEWMAN or with 500 CFU of *E. coli* strain IHE3034. Survival of the mice following infection was monitored on a daily basis.

At least two independent experiments were performed.

Results

Wild-type mice were unable to survive infection with the indicated bacteria beyond 48 hours post-infection (FIG. 7). In contrast, the majority of TLR2$^{-/-}$ mice were still alive at 12 days after infection.

Discussion

The results shows that TLR2-deficient neonatal mice have increased survival against challenging infections with *E. coli* and *S. aureus* compared to wild-type mice. TLR2 thus plays an important role in neonatal susceptibility to sepsis; that is to say, TLR2 deficiency improves neonatal survival and confers protection to bacterial sepsis. In addition to the results obtained in Example 2, these data thus confirm the importance of TLR2 as a receptor for GAPDH, across the different species of sepsis-inducing bacteria.

Example 4—Type I Interferon Production by Dendritic Cells Induced by Bacteria Synergises with GAPDH to Increase IL-10 Production on B1 Cells This study aimed to identify whether B1 cells are assisted in the production of IL-10 upon GAPDH recognition by other leukocyte populations, and in what capacity.

Materials and Methods

Total spleen cells were obtained from newborn mice, and B1 cells were purified from the total spleen cell population, as described above.

The different spleen cell populations were stimulated in vitro with 25 µg/mL of rGAPDH, $10^7$ cells of GBS fixed in isopropanol (GBSf) or with RPMI medium alone for 12 h at 37° C. with 5% carbon dioxide. In all conditions $5 \times 10^5$ cells/well were used, except for the purified B1 cell study where $2.5 \times 10^5$ cells/well were used.

Dendritic cells were derived from foetal liver as described above. The dendritic cells were co-cultured with $2.5 \times 10^5$ of the B1 cells purified from newborn spleen in a 1:10 ratio and stimulated with 25 µg/mL of rGAPDH, $10^7$ cells of GBSf, 20 µg/mL of anti-IFNAR or with RPMI medium alone for 12 h at 37° C. with 5% carbon dioxide.

After incubation of the different cell types, IL-10 was quantified in the supernatants as described above.

At least two independent experiments were performed in each case.

Results & Discussion

The ability of GAPDH to induce IL-10 production in total spleen cells was strongly increased in the presence of fixed bacteria (FIG. 6A). Nevertheless, this effect was lost in purified B1 cells, where adding fixed bacteria did not increase the IL-10 production induced by GAPDH (FIG. 6B).

This result indicates that different leukocyte population(s) other than B1 cells are stimulated by bacterial antigens and help B1 cells to produce IL-10 upon GAPDH recognition.

The co-culture study enabled understanding of the role of other sub-populations of leukocytes in the influence of B1 cells to produce IL-10. The inventors observed that in the presence of dendritic cells, B1 cells produced elevated amounts of IL-10 when stimulated simultaneously with GAPDH plus GBSf (FIG. 6C). Interestingly, this effect was abrogated when type I interferon signalling was blocked (FIG. 6C).

This result indicates that upon bacterial recognition, dendritic cells produce type I interferon that increase IL-10 production in B1 cells stimulated with GAPDH.

Example 5—Early IL-10 Production is a Generalised Mechanism Used by Sepsis-Inducing Bacteria to Colonise the Neonatal Host The ability to produce high amounts of IL-10 was demonstrated to be the main reason for the susceptibility of neonates against GBS infections [24]. The present study aimed to investigate whether the same happens in neonatal infections caused by bacteria other than GBS, specifically *E.* coli or *S. aureus*. Together with GBS, *E. coli* and Staphylococcal spp. are responsible for up to 87% of the cases of sepsis in human neonates.

The study also aimed to investigate whether other bacteria also possess extracellular GAPDH, as an indication of a generalised IL-10-dependent mechanism used by sepsis-inducing bacteria to colonise the neonatal host.

Materials and Methods

Neonatal mice were treated with blocking antibodies specific for the mouse IL-10 receptor (anti-IL10R) before challenge with *E. coli* or *S. aureus*, as follows.

Newborn mice were intraperitoneally injected with 100 µg of anti-IL10R monoclonal antibodies or 100 µg of isotype control IgG as described above. 12 h later the mice were challenged subcutaneously with 500 CFU of *E. coli* strain IHE3034 or with $5 \times 10^5$ CFU of *S. aureus* strain. Survival of the mice following infection was monitored on a daily basis.

Three independent experiments were performed.

To investigate whether other sepsis-inducing pathogens also possess extracellular GAPDH, extracellular proteins from culture supernatants of pathogens of interest were obtained, separated by SDS-PAGE and analysed by western-blot using anti-rGAPDH antibodies, as follows.

Cultures of GBS strain NEM316, *P. aeruginosa*, *S. pneumoniae*, *S. aureus* and *E. coli* were prepared as described above, and extracellular proteins purified from the culture supernatants in accordance with standard procedures. SDS-PAGE and Western-blot analysis were performed according to standard procedures using anti-rGAPDH antibodies (IgG) obtained from rGAPDH-immunised rabbits as described above. rGAPDH was used as a positive control.

Five independent experiments were performed.

The effect of neutralising GAPDH secreted by these bacteria, to assess whether these pathogens also use GAPDH secretion as a virulence mechanism, was investigated as follows.

Mice pups were intraperitoneally injected with 80 µg of anti-rGAPDH antibodies (IgG) or 80 µg of control IgG as described above. 12 h later the mice were challenged subcutaneously with $5 \times 10^6$ CFU of *S. pneumoniae* strain Tigr4, 500 CFU of *E. coli* strain IHE3034 or $5 \times 10^5$ CFU of *S. aureus* strain NEWMAN. Survival of the mice following infection was monitored on a daily basis.

Two independent experiments were performed.

Results

Interestingly, blocking IL-10 signalling significantly improved survival of neonates to infections caused by *E. coli* and *S. aureus*, when compared with pups that received isotype-matched control antibodies (FIG. 8).

Other sepsis-inducing bacteria were also shown to possess extracellular GAPDH (FIG. 9). Neutralisation of this secreted GAPDH using anti-rGAPDH antibodies was shown to protect newborn mice from infection by *S. pneumoniae*, *E. coli* and *S. aureus* (FIG. 10A-C, respectively).

Discussion

The results indicate that the mechanism observed for the susceptibility of neonates against GBS-induced sepsis is transversal to other sepsis-inducing bacteria. Although IL-10 data for neonatal infections caused by *E. coli* and *S. aureus* are provided here, the fact that other bacteria also secrete GAPDH is a strong indicator that the propensity of neonates to produce high amounts of IL-10 in response to bacterial GAPDH is a global mechanism used by different bacterial pathogens, which leads to the development of sepsis. This result validates the fact that a GAPDH-based vaccine against GBS will also be viable against other sepsis-inducing bacteria too.

Example 6—GAPDH-Induced IL-10 Production is a Mechanism Conserved in Human Cells This study aimed to investigate whether human cells also produce IL-10 in response to GAPDH.

Materials and Methods

Mononuclear cells were separated from human cord-blood or adult peripheral blood as described above.

The cells were stimulated in vitro with 25 µg/mL of rGAPDH, 10 µg/mL of OxPAC (a TLR2 inhibitor) or RPMI medium alone for 12 h at 37° C. with 5% carbon dioxide.

After incubation of the cells, IL-10 was quantified in the supernatants as described above.

At least two independent experiments were performed.

Results

In agreement with what was observed in neonatal mice, the stimulation of mononuclear cells purified from human cord-blood or adult peripheral blood with rGAPDH induced the production of high amounts of IL-10 (FIG. 11A and FIG. 11B, respectively).

Interestingly, GAPDH-induced IL-10 production in human leukocytes was completely abrogated in the presence of a TLR2 inhibitor.

Discussion

This result shows that the mechanism for IL-10 production induced by GAPDH in mouse cells is also true for humans.

Moreover, the fact that the same virulence mechanism studied in mice can be readily translated to humans strongly supports the use of mice as an excellent model to study bacterial sepsis in man.

Example 7—Production of Neonatal Vaccine

Based on their discovery that the propensity of neonates to produce high amounts of IL-10 in response to bacterial GAPDH is a global mechanism used by different bacterial pathogens, the inventors set out to produce a vaccine against such pathogens using GAPDH-derived peptides as the antigen.

Materials and Methods

Neonatal Vaccine was prepared as described above.

Results Vaccines of the invention are composed from surface peptides of GAPDH from the different sepsis-inducing bacteria, which have amino acid sequences that are absent from human GAPDH. As such, the inventors have developed vaccines composed of peptides belonging to conserved sequences of microbial GAPDH that are not shared by human GAPDH.

FIG. 2 includes a table identifying the amino acid sequences of four exemplary peptides that were found in the present study, using the above method, and the respective bacteria that possess each amino acid sequence. Below the table are images showing the surface localisation of the same four peptides in the different bacterial GAPDHs.

FIGS. 12 and 13 illustrate how two further peptides from *E. coli* and *P. aeruginosa* (identified as Peptides 3 and 4, respectively, in FIG. 2) have (bacterially conserved) amino acid sequences which are not found in man.

Figure 2:
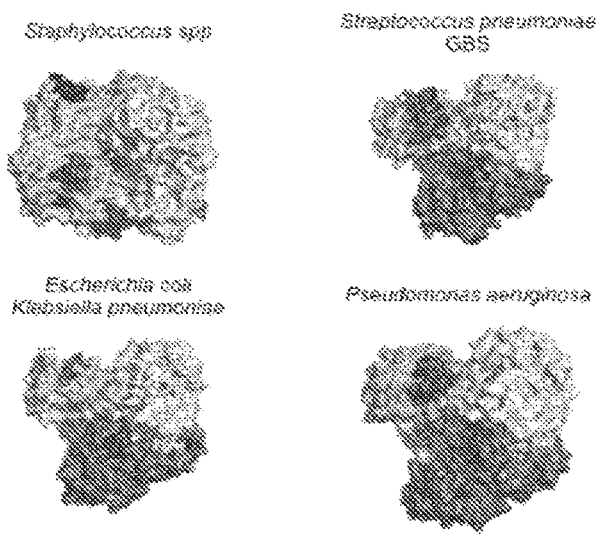
Figure 3:
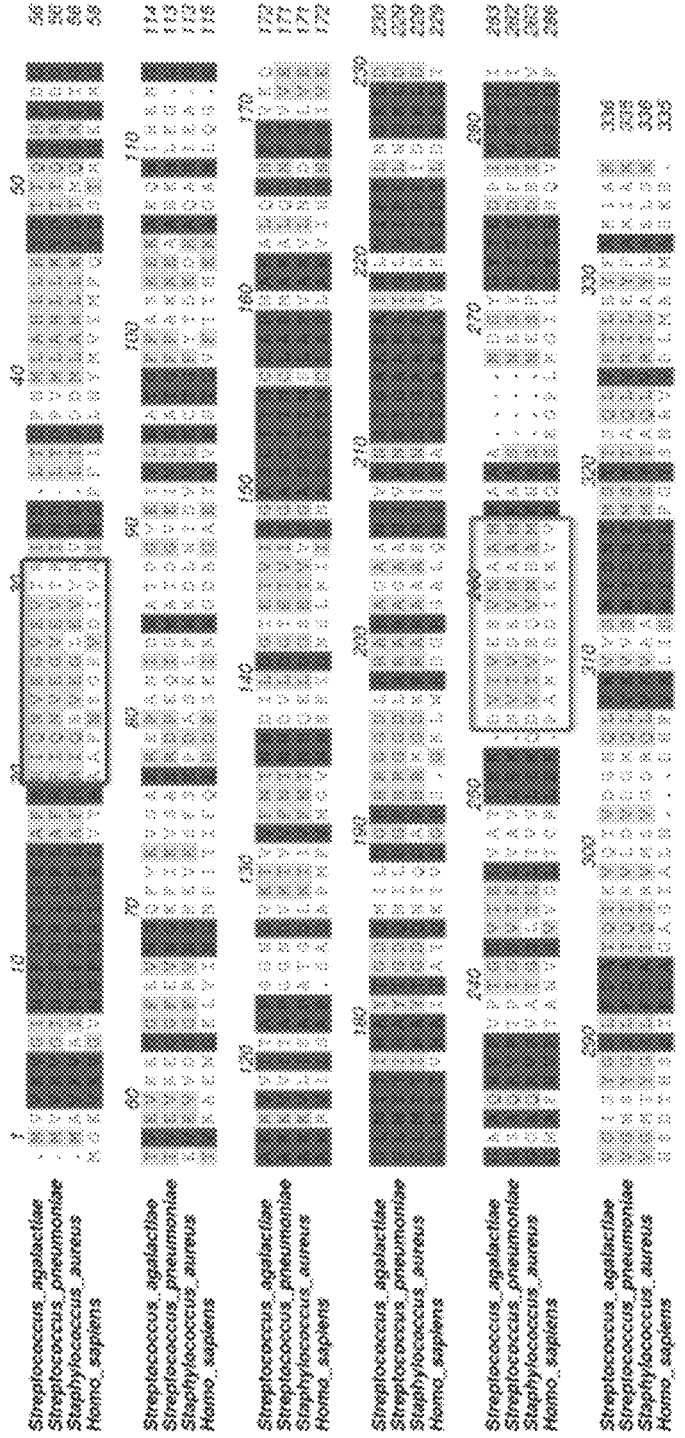
FIG. 3 illustrates how two of the peptides (identified as Peptides 1 and 2 in FIGS. 2 and 3) have amino acid sequences which are conserved amongst certain bacterial species, but not in humans.
Figure 5:
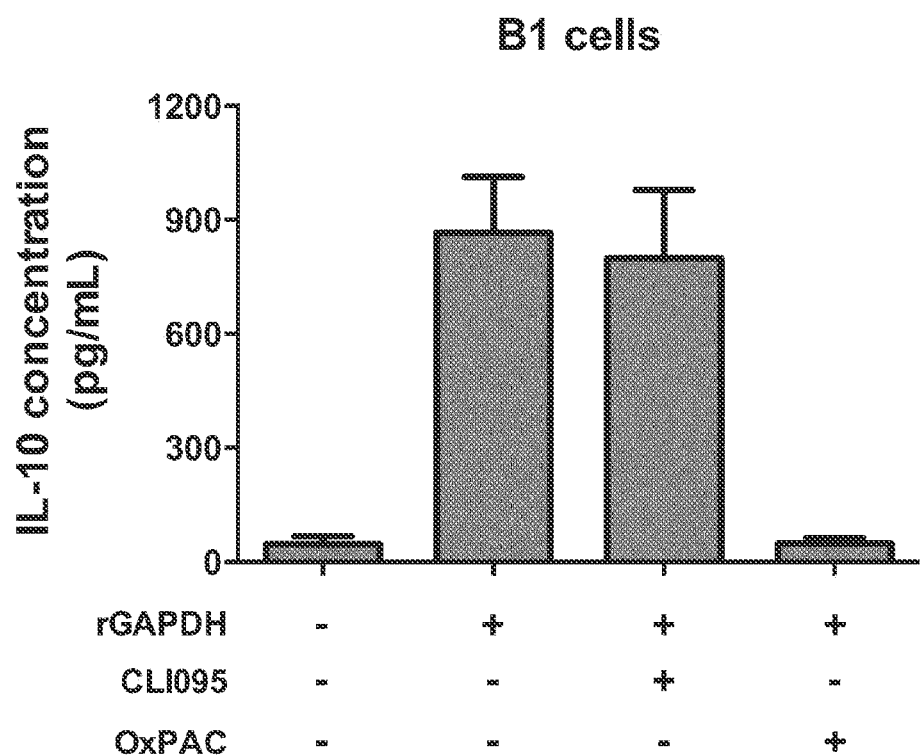
Figure 6:
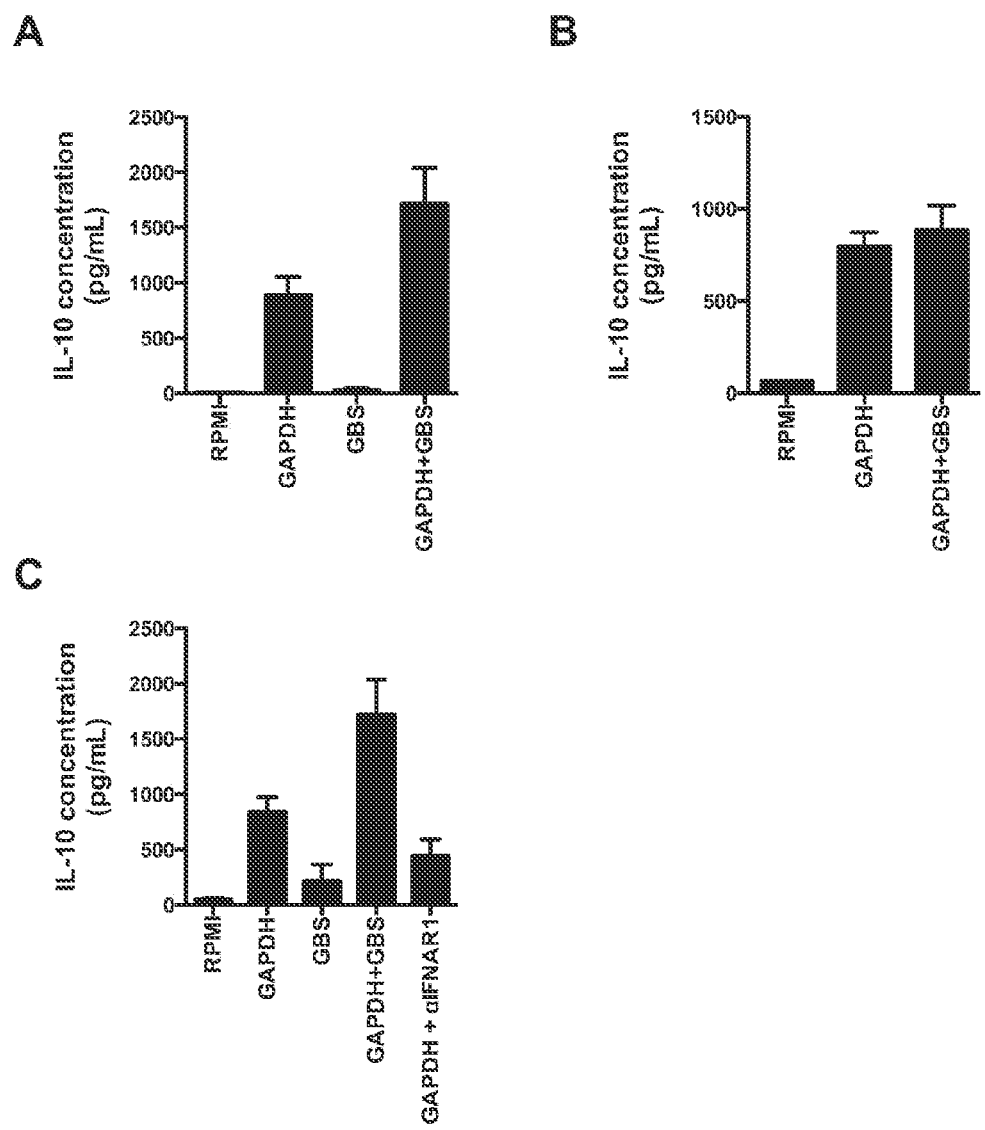
Figure 7:
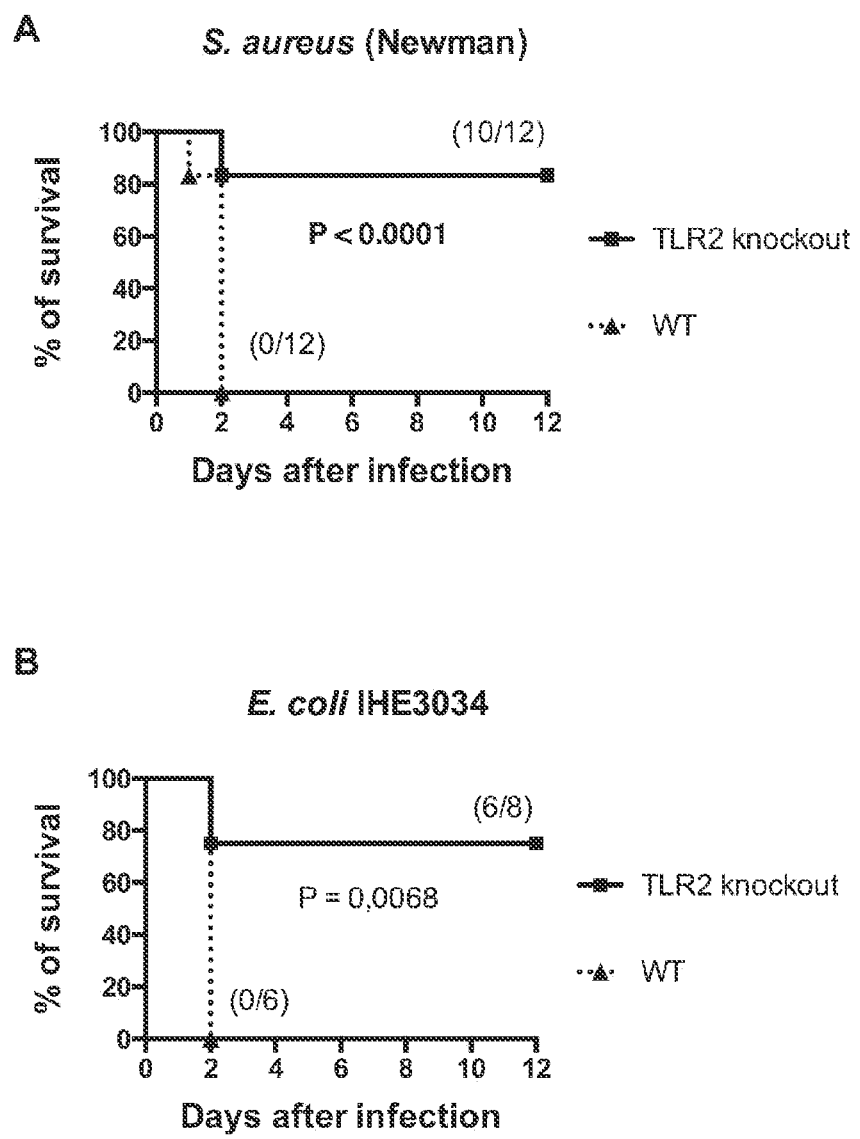
Figure 9:
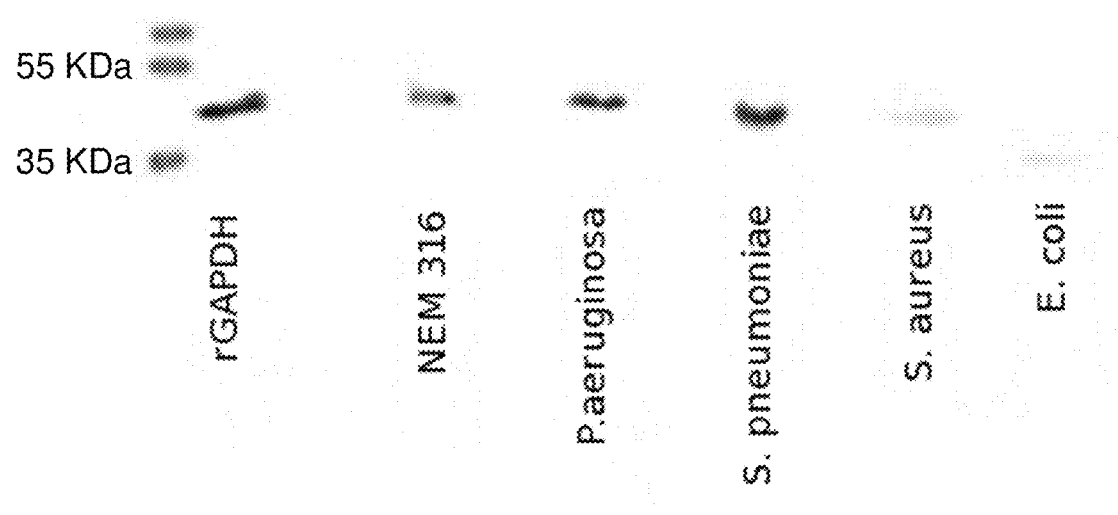
Figure 10:
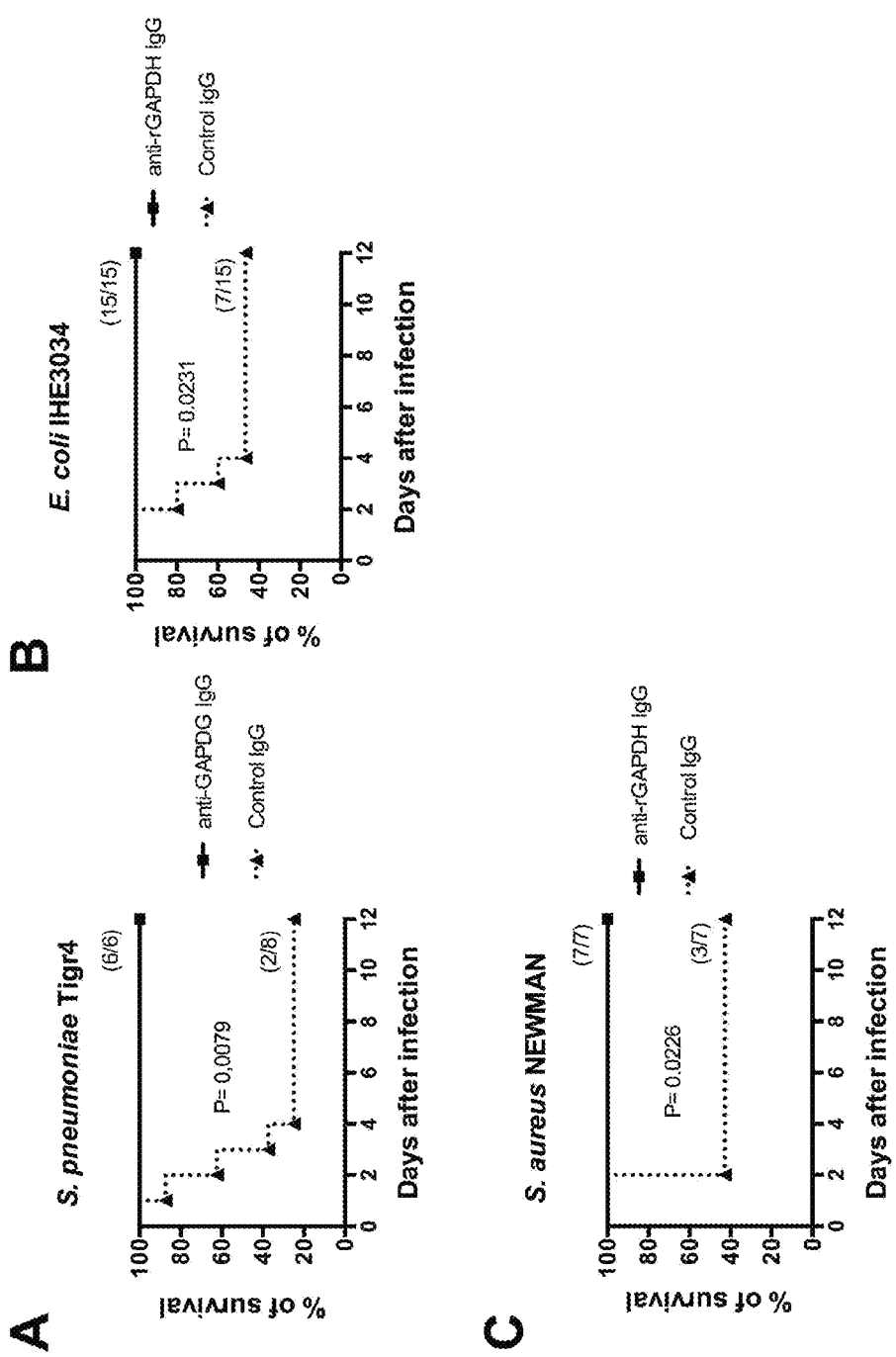
Figure 11:
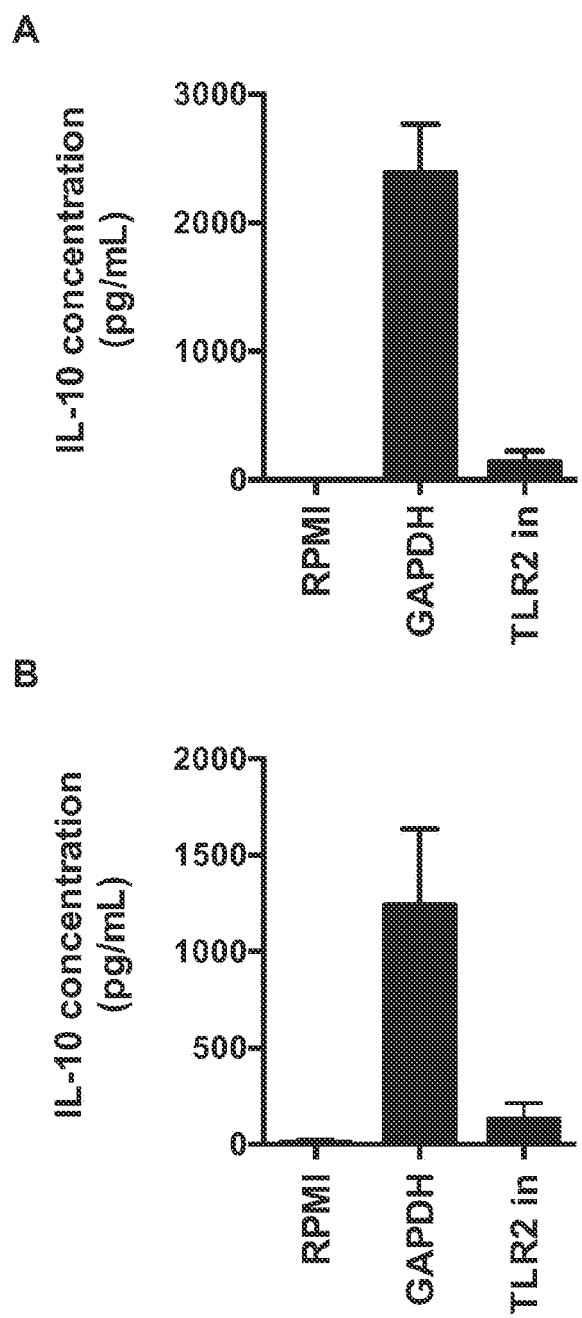

Peptides 1-4 were used in combination in the preparation of a preferred vaccine of the invention, referred to herein as Neonatal Vaccine. Thus, Neonatal Vaccine is suitable for use against all of the bacteria listed in the table in FIG. 2.

Peptides 1-4, however, are mere examples; that is to say, other peptides that are suitable for use in a vaccine of the invention can be identified by sequence alignment in the same way as set out above. Any other amino acid sequence can be used from GAPDHs of the referred pathogens. As explained herein, however, it is preferable to avoid any sequences that are also found in man, so as to avoid any autoimmune pathologies.

As described herein, any number of peptides, in any combination, can be used instead so of Peptides 1-4 of Neonatal Vaccine. That is to say, the number and identity of peptides that constitute a vaccine of the invention can vary.

Discussion

As explained herein, bacterial GAPDH plays a role in causing immunosuppression in neonates and immunocompromised hosts and promoting bacterial sepsis. The vaccines described herein, including the specific Neonatal Vaccine described in this example, are thus directed to protect susceptible hosts (including neonates, the elderly and other such immunocompromised individuals) from infections caused by GBS, *E. coli, Staphylococcus* spp., *S. pneumoniae, K. pneumoniae* and *Pseudomonas* spp. The approach taken by the inventors allows the possibility to "tailor" a vaccine of the invention for any sepsis-inducing bacteria, simply by selecting the surface-exposed peptides of its GAPDH that are absent from human GAPDH.

Example 8—Antibodies Elicited with Neonatal Vaccine React with Bacterial GAPDH

This study aimed to show that the vaccine produced in Example 7 could be used to produce antibodies that recognise bacterial GAPDH.

Materials and Methods

Mice and rats were immunised with Neonatal Vaccine as described above.

Cultures of GBS strain NEM316, *P. aeruginosa, S. pneumoniae, S. aureus, E. coli, K. pneumoniae* and MenB were prepared as described above, and extracellular proteins purified from the culture supernatants in accordance with standard procedures. SDS-PAGE and Western-blot analysis were performed according to standard procedures using anti-GAPDH antibodies (IgG) obtained from the rGAPDH-immunised mice and rats as described above. rGAPDH was used as a positive control.

Two independent experiments were performed.

Results

Figure 14:
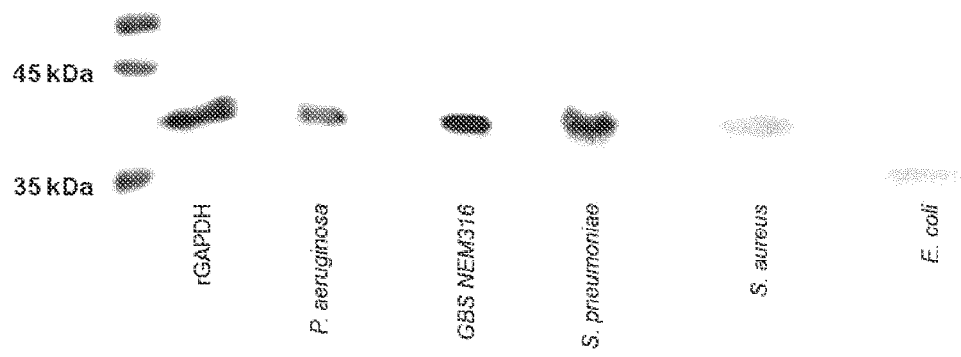
Figure 15:
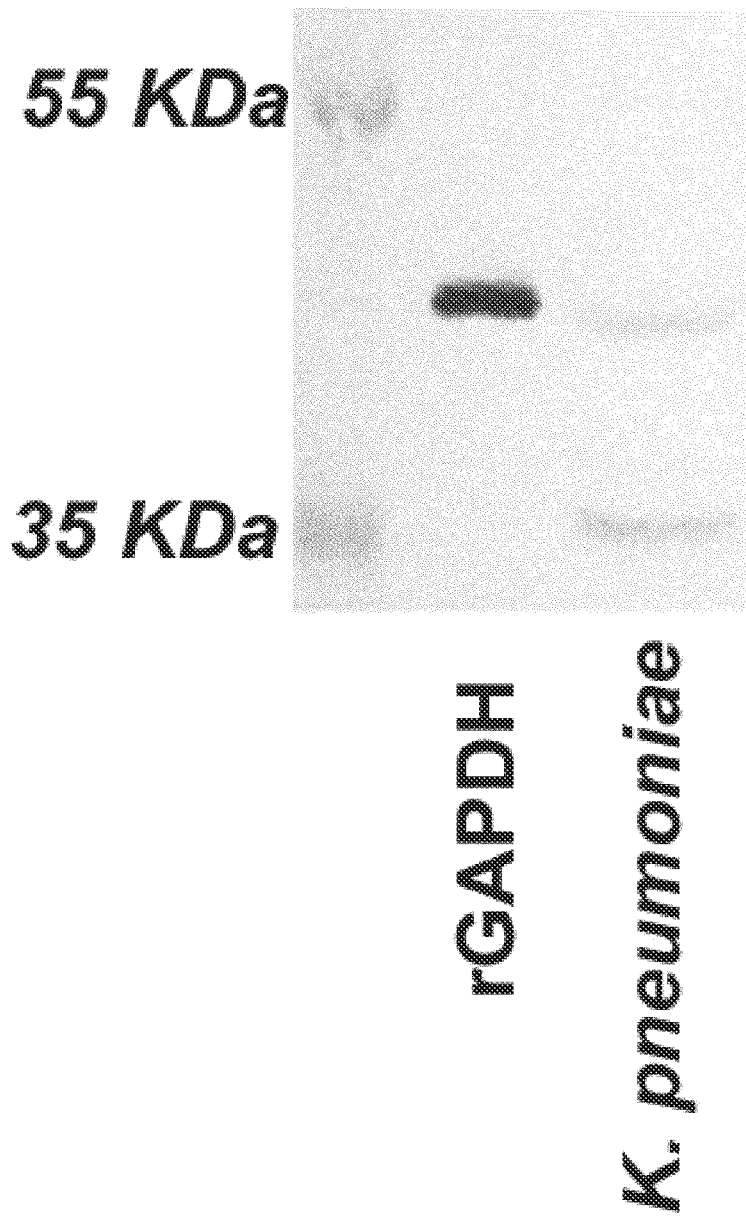
Figure 16:
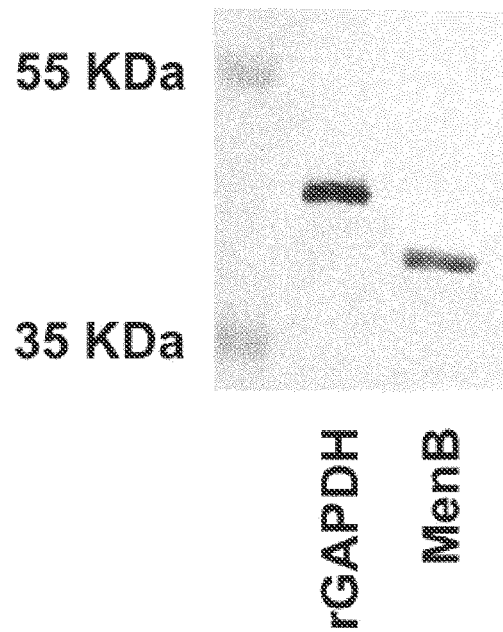

As shown in FIGS. 14-16, antibodies purified from mice and rats immunised with Neonatal Vaccine react with extracellular GAPDH from the different bacteria.

FIG. 15 (showing results from *K. pneumoniae*) reveals two bands that are recognised by anti-GAPDH antibodies elicited with Neonatal Vaccine. Interestingly, the band of ~45 KDa corresponds to exactly the same molecular weight of GBS GAPDH. The other band (~35 KDa) corresponds to the predicted molecular weight of *K. pneumoniae* GAPDH (http://www.uniprot.org/uniprot/C4X7S6).

FIG. 16 (showing results from MenB) reveals a band of ~37 kDa, which corresponds to the predicted molecular weight of MenB GAPDH [51].

Discussion

This study shows that antibodies elicited with Neonatal Vaccine recognise GAPDH from GBS strain NEM316, *P. aeruginosa, S. pneumoniae, S. aureus, E. coli, K. pneumoniae* and MenB. These data therefore provide proof-of-concept that bacterial peptide sequences in common can be used in a vaccine to recognise bacterial GAPDH.

Although only serotype B of *N. meningitidis* has been tested here, similar results would be expected for all other serotypes of this bacterium. In this regard, GAPDHs from the different serotypes of *N. meningitidis* share high (97.668%) homology (http://www.uniprot.org/align/A20150610146R80D4XR) and antibodies elicited with Neonatal Vaccine would therefore be expected to recognise GAPDH from them all. It is consequently believed that the vaccines described herein are advantageous for all the serotypes of *N. meningitidis*.

The result illustrated in FIG. 15 also shows that, interestingly, *K. pneumoniae* may possess two isoforms of GAPDH.

Example 9—Neonatal Vaccine Protects Neonates from GBS Infection

This study aimed to show that the antibodies produced in Example 8 could be used to protect newborn mice from GBS infection.

Materials and Methods

Mice pups were intraperitoneally injected with 80 µg of Neonatal Vaccine-induced IgG or 80 µg of control IgG as described above. 12 h later the mice were challenged subcutaneously with $5 \times 10^6$ CFU of GBS NEM316. Survival of the mice following infection was monitored on a daily basis.

Two independent experiments were performed.

Results

Figure 17:
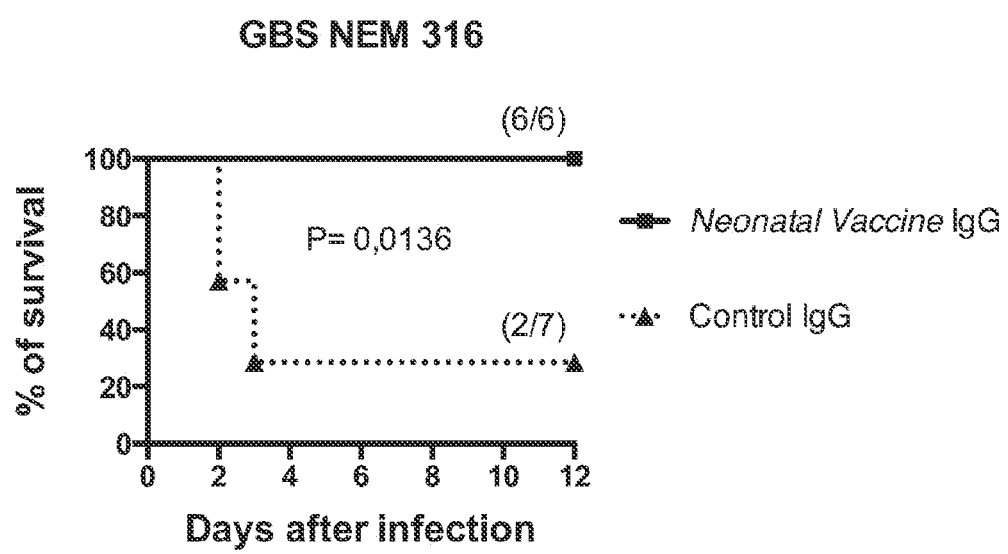

Maternal vaccination with rGAPDH (whole protein) has previously proven to be an efficient strategy to prevent neonatal infections caused by GBS [24]. However, when antibodies elicited with Neonatal Vaccine were used for passive immunisations of pups before GBS infection, the protection was even more effective. Indeed, the protection conferred with Neonatal Vaccine was 100% (FIG. 17).

Discussion

This result shows that the new approach used to develop the vaccines of the invention, including Neonatal Vaccine, (i.e. using select peptide sequences, as described herein, instead of the whole protein) directs the immune system of neonates to a more robust and specific response towards sepsis-inducing agents, exemplified by GBS, compared to that previously described.

This result also shows that the immunity provided by Neonatal Vaccine is reproducible (1000% effective), which is clearly advantageous.

Although this study only looked at GBS infection, it is understood that the same result would be observed upon infection by other sepsis-inducing bacteria (not least because Example 8 shows that antibodies elicited with Neonatal Vaccine recognise GAPDH from GBS strain NEM316, *P. aeruginosa, S. pneumoniae, S. aureus, E. coli, K. pneumoniae* and *N. meningitidis* (as exemplified by MenB)).

Moreover, the results presented in FIG. 17 provide evidence that maternal vaccination with Neonatal Vaccine (or, therefore, maternal treatment with the anti-GAPDH antibodies of the invention), will significantly reduce stillbirths and premature births caused by intra-vaginal GBS infection. Indeed, as discussed above in connection with the twelfth aspect of the invention, antibodies raised against a peptide, fragment, variant or vaccine of the invention can pass to an unborn baby across the mother's placenta. In addition, and as shown in FIG. 17, the protection against GBS conferred on pups following immunisation with Neonatal Vaccine-induced antibodies was 100%.

Owing to the high sequence similarity and functional homology between GAPDH of GBS and the other sepsis-inducing bacteria as described herein, the presented data also indicate that Neonatal Vaccine will effectively prevent stillbirths and pre-term births caused by other sepsis-inducing bacteria too. This is an important finding, as bacterial infections are responsible for approximately 650,000 stillbirths per year worldwide [52,53]. In addition, about 50% of preterm births at less than 32 weeks of gestation are also caused by bacterial infections [9,14,53-56]. The vast majority are caused by maternal commensal bacteria that ascend from the vaginal tract into the amniotic fluid. GBS, *E. coli* and *K. pneumoniae* are the most common pathogens found in autopsies of stillbirth babies caused by ascending bacterial infections.

Example 10—Neutralisation of Bacterial GAPDH is a Global Approach to Protect Neonates from Bacterial Sepsis This study aimed to extend the work described in Example 9, by investigating whether antibody-mediated neutralisation of bacterial GAPDH could prevent neonatal infections caused by the other relevant sepsis-inducing bacteria.

Materials and Methods

Mice pups were intraperitoneally injected with 80 μg of Neonatal Vaccine-induced IgG or 80 μg of control IgG as described above. 12 h later the mice were challenged subcutaneously with $10^7$ CFU of *S. pneumoniae* strain Tigr4, 500 CFU of *E. coli* strain IHE3034 or $5 \times 10^5$ CFU of *S. aureus* strain NEWMAN. Survival of the mice following infection was monitored on a daily basis.

Results

As shown in FIG. 18, the use of antibodies elicited with Neonatal Vaccine in passive immunisations of neonates significantly improve survival upon bacterial challenge. Here are shown results for *S. pneumoniae*, *E. coli* and *S. aureus* (see FIG. 18A-C, respectively).

Discussion

As discussed herein, currently there is no available vaccine directed to any of the most so relevant sepsis-inducing bacteria. Presented here are data demonstrating that antibody-mediated neutralisation of bacterial GAPDH prevents neonatal infections caused by the most relevant sepsis-inducing bacteria.

Example 11—Therapeutic Administration of Neonatal Vaccine IgG Antibodies Protects Newborn Mice from GBS Infection This study aimed to investigate whether antibodies elicited with Neonatal Vaccine could treat an existing neonatal infection caused by sepsis-inducing bacteria.

Materials and Methods

Neonatal Vaccine IgG, control IgG (80 μg) or saline solution (0.9% NaCl) were intraperitoneally injected into mice pups (up to 48 h old) 6 h after subcutaneous infection with $5 \times 10^6$ GBS NEM316 CFU. At the time of treatment all mice presented clear signs of infection, assessed by intense rash at the site of infection. Survival of the mice following infection was monitored on a 12-hourly basis.

Results

Figure 19:
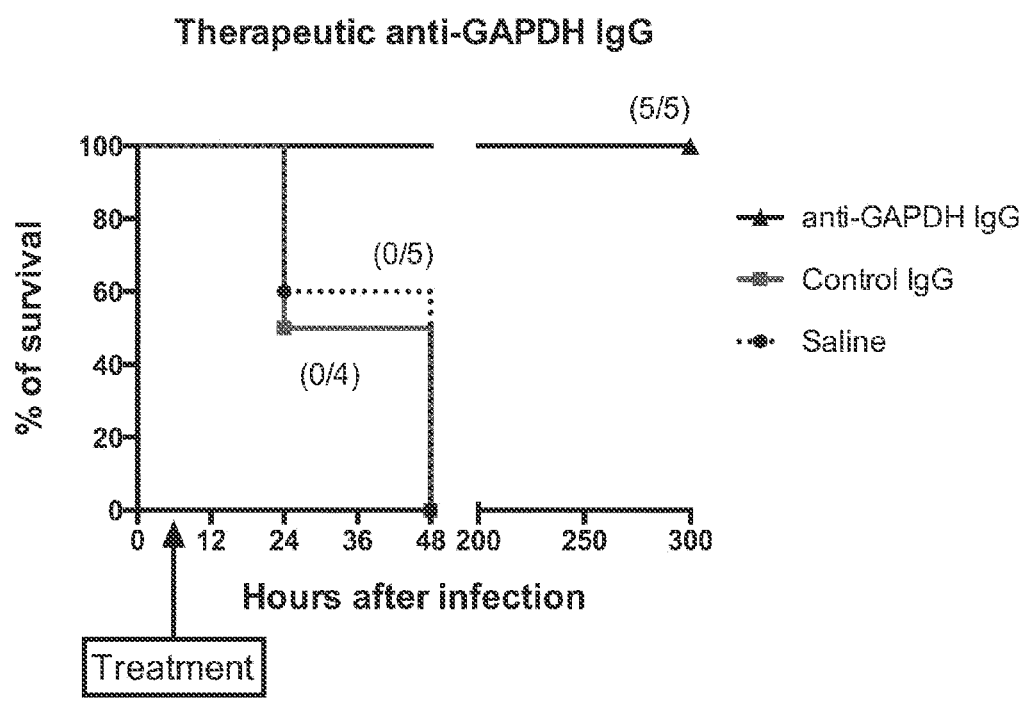

As shown in FIG. 19, only the mice that received Neonatal Vaccine-induced IgG antibodies were able to survive GBS infection. In fact, treatment of mice pups with anti-GAPDH IgG antibodies after GBS infection resulted in complete survival of the animals. In contrast, none of the controls survived the infection.

Discussion

As discussed herein, the current treatment available for neonatal sepsis is based only on antibiotic administration. Presented here are data demonstrating that antibodies induced by Neonatal Vaccine can be used to treat existing neonatal infections caused by GBS, one of the most relevant sepsis-inducing bacteria.

Although this study only looked at GBS infection, it is understood that the same result would be observed upon infection by other sepsis-inducing bacteria (not least because Example 8 shows that antibodies elicited with Neonatal Vaccine recognise GAPDH from GBS strain NEM316, *P. aeruginosa*, *S. pneumoniae*, *S. aureus*, *E. coli*, *K. pneumoniae* and *N. meningitidis* (as exemplified by MenB)).

The peptides, fragments and variants of the first aspect of the invention thus have significant utility in creating a variety of useful and much-needed antibody-based therapeutics for the indicated patient populations.

Example 12—Neonatal Vaccine Protects Old Mice from GBS Infection

This study aimed to show that the antibodies produced in Example 8 could be used to protect old mice from GBS infection.

Materials and Methods

Old C57Bl/6 mice (aged over 16 months) were intraperitoneally injected with 1 mg/kg of Neonatal Vaccine-induced IgG or the same amount of isotyped matched IgG as a control daily for three days. 24 h after the last dose the mice were challenged subcutaneously with $2 \times 10^7$ CFU of GBS NEM316. Survival of the mice following infection was monitored on a daily basis for 12 days.

Two independent experiments were performed.

Results

Figure 20:
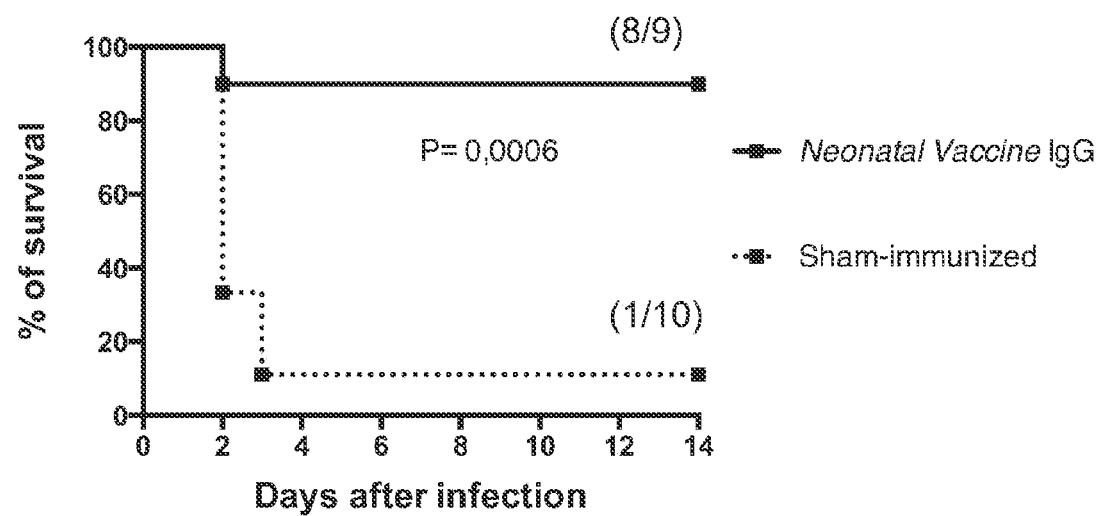

Vaccination with Neonatal Vaccine was shown to protect old mice against lethal GBS infection. Indeed, eight out of nine mice (90%) injected with Neonatal Vaccine survived the bacterial challenge compared to only one of ten (10%) controls (FIG. 20).

Discussion

This result shows that the vaccines of the invention, including Neonatal Vaccine, can direct the immune system of old mice to a robust and specific response towards sepsis-inducing agents, as exemplified by GBS, in a parallel fashion to that demonstrated in neonates (see Example 9).

The inventors firmly believe, therefore, that susceptibility to infection by sepsis-inducing bacteria in the elderly is underpinned by the same mechanism as they have discovered in neonates (i.e. GAPDH, which is secreted by the GBS bacteria, acts on B1 cells through TLR2 in order to induce IL-10 production). Indeed, the data provided herein show that Neonatal Vaccine can be used to produce antibodies that recognise bacterial GAPDH produced by GBS, and this is clearly having a protective effect in the so old mice, just as has been observed in neonates. The inventors therefore also firmly believe that the same would be true for other such immunocompromised hosts.

Although this study only looked at GBS infection, it is understood that the same result would be observed upon infection by other sepsis-inducing bacteria (not least because Example 8 shows that antibodies elicited with Neonatal Vaccine recognise GAPDH from GBS strain NEM316, *P. aeruginosa*, *S. pneumoniae*, *S. aureus*, *E. coli*, *K. pneumoniae* and *N. meningitidis* (as exemplified by MenB)). The results seen with Neonatal Vaccine in neonatal mice challenged with the different bacterial strains (see Example 10)

could therefore reasonably be expected in other immunocompromised hosts, such as old mice, too.

As described herein, currently there is no available vaccine that efficiently protects the elderly against infections caused by any of the most relevant sepsis-inducing bacteria. Therapeutic strategies to combat sepsis in this group are also far from effective. Presented herein are data demonstrating that antibody-mediated neutralisation of bacterial GAPDH prevents infections caused by the most relevant sepsis-inducing bacteria in the elderly. Vaccination is the most cost-effective treatment for infectious diseases, even more so when the same vaccine could prevent infections caused by different human pathogens in different age groups, as has been demonstrated here.

The data obtained in the old mice are proof-of-concept that the other results obtained in the neonates would be obtained in the elderly and other such immunocompromised hosts too. The administration of Neonatal Vaccine IgG antibodies to old mice suffering an existing infection caused by sepsis-inducing bacteria is therefore expected to result in their treatment, just as has been observed in the neonates (see Example 11). As the current treatment available for sepsis is based only on antibiotic administration, the fact that antibodies induced by Neonatal Vaccine could be used to treat existing infections caused by the most relevant sepsis-inducing bacteria in the elderly, as well as in neonates and the other patient populations indicated herein, is clearly advantageous.

Example 13—Neonatal Vaccine Protects NOD Mice Against GBS Infection

This study aimed to show that the antibodies produced in Example 8 could be used to protect a transgenic mouse model of diabetes (NOD mice) from GBS infection.

Materials and Methods

NOD mice (eight weeks of age) were intraperitoneally injected with 1 mg/kg of Neonatal Vaccine-induced IgG or the same amount of isotyped matched IgG as a control daily for three days. 24 h after the last dose the mice were challenged subcutaneously with $5 \times 10^7$ CFU of GBS NEM316. Survival of the mice following infection was monitored on a daily basis for 12 days.

Two independent experiments were performed.

Results

Figure 21:
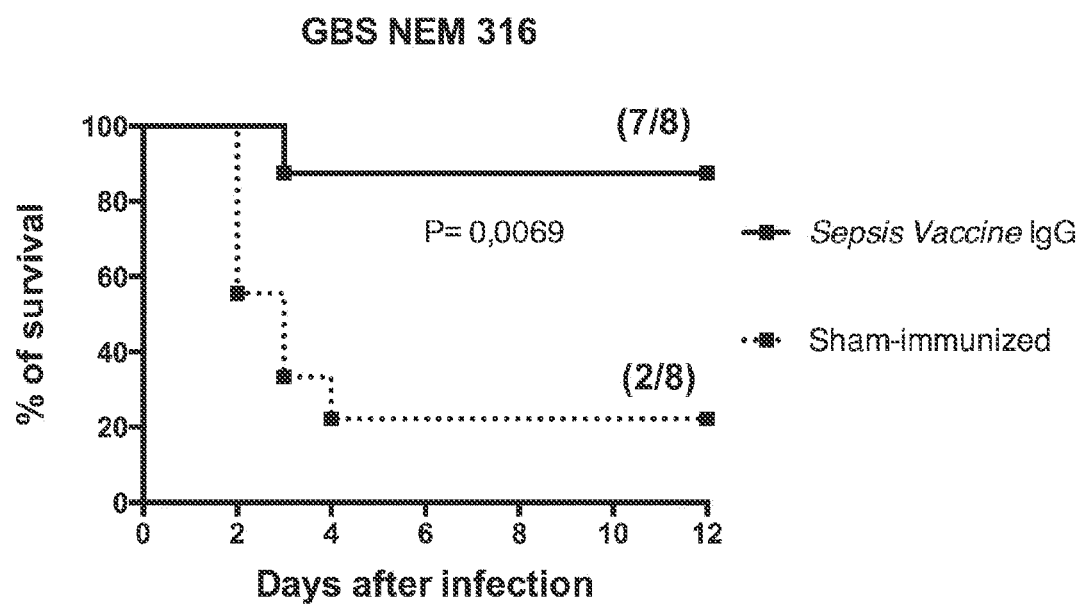

Passive immunisation using Neonatal Vaccine-induced IgG was shown to protect NOD mice against lethal GBS infection. Indeed, seven out of eight mice (90%) injected with Neonatal Vaccine-induced IgG survived the bacterial challenge compared to only two of eight (25%) sham-immunised controls (FIG. 21).

Discussion

This result shows that the vaccines of the invention, including Neonatal Vaccine, can direct the immune system of a transgenic mouse model of diabetes to a robust and specific response towards sepsis-inducing agents, as exemplified by GBS, in a parallel fashion to that demonstrated in neonates (see Example 9) and the elderly (see Example 12).

The inventors firmly believe, therefore, that susceptibility to infection by sepsis-inducing bacteria in diabetics, as per the elderly, is underpinned by the same mechanism as they have discovered in neonates (i.e. GAPDH, which is secreted by the GBS bacteria, acts on B1 cells through TLR2 in order to induce IL-10 production).

Indeed, the data provided herein show that Neonatal Vaccine can be used to produce antibodies that recognise bacterial GAPDH produced by GBS, and this is clearly having a protective effect in the diabetic mice, just as has been observed in neonates (and the elderly). The inventors therefore also firmly believe that the same would be true for other such immunocompromised hosts.

Again, although this study only looked at GBS infection, it is understood that the same result would be observed upon infection by other sepsis-inducing bacteria (not least because Example 8 shows that antibodies elicited with Neonatal Vaccine recognise GAPDH from GBS strain NEM316, *P. aeruginosa, S. pneumoniae, S. aureus, E. coli, K. pneumoniae* and *N. meningitidis* (as exemplified by MenB)). The results seen with Neonatal Vaccine in neonatal mice challenged with the different bacterial strains (see Example 10) could therefore reasonably be expected in other immunocompromised hosts, such as diabetics, too.

As described herein, diabetic patients have increased susceptibility to infection by sepsis-inducing bacteria. Presented herein are data demonstrating that antibody-mediated neutralisation of bacterial GAPDH prevents infections caused by the most relevant sepsis-inducing bacteria in this patient group. As explained, vaccination is the most cost-effective treatment for infectious diseases, even more so when the same vaccine could prevent infections caused by different human pathogens in different age groups and across different diseases, conditions and disorders, as has been demonstrated here.

The data obtained in the diabetic mice are also proof-of-concept that the other results obtained in the neonates would be obtained in diabetics and other such immunocompromised hosts too. The administration of Neonatal Vaccine IgG antibodies to diabetic mice suffering an existing infection caused by sepsis-inducing bacteria is therefore expected to result in their treatment, just as has been observed in the neonates (see Example 11).

As the current treatment available for sepsis is based only on antibiotic administration, the fact that antibodies induced by Neonatal Vaccine could be used to treat existing infections caused by the most relevant sepsis-inducing bacteria in diabetics, as well as in neonates, the elderly and other patient populations indicated herein, is clearly advantageous.

CONCLUDING REMARKS

The data presented in the Examples show the relevance of vaccines and treatments of the invention, including Neonatal Vaccine, to protect immunocompromised hosts such as neonates, babies, children, women of fertile age, pregnant women, foetuses and the elderly, in particular, from bacterial sepsis.

Moreover, the rationale of Neonatal Vaccine and the other vaccines and treatments described herein represents significant new inventive steps regarding the previous published results [24,25], namely:

a) The mechanism by which bacterial GAPDH induces IL-10 in the neonatal host;

b) GAPDH-induced IL-10 production is associated with susceptibility to bacterial sepsis caused by different pathogens;

c) GAPDH-induced IL-10 production is a mechanism conserved in human cord-blood cells;

d) GAPDH-induced IL-10 production is a mechanism conserved in leukocytes isolated from the peripheral blood of adult humans;

e) The efficacy of anti-GAPDH antibodies in preventing stillbirths caused by GBS;

f) Antibodies elicited by Neonatal Vaccine (and other vaccines described herein) recognise extracellular GAPDH from GBS, *P. aeruginosa, E. coli, S. pneumoniae, K. pneumoniae, S. aureus* and *N. meningitidis*.

g) Neutralisation of bacterial GAPDH by means of passive immunisation with antibodies elicited with Neonatal Vaccine (and other vaccines described herein), protects newborns from sepsis caused by GBS, *E. coli, S. pneumoniae* and *S. aureus*;

h) The use of peptides derived from GAPDH of sepsis-inducing bacteria and the use of anti-GAPDH IgG antibodies, either as a preventive strategy or as a treatment for neonatal sepsis and sepsis in other patient groups as indicated herein.

REFERENCES

1. Edmond K, Zaidi A (2010) PLoS Med 7: e1000213.
2. Lukacs S L, Schrag S J (2012) J Pediatr 160: 960-965 e961.
3. van den Hoogen A, Gerards L J, Verboon-Maciolek M A, et al. (2010) Neonatology 97: 22-28.
4. Stoll B J, Hansen N I, Adams-Chapman I, et al. (2004) JAMA 292: 2357-2365.
5. Edmond K M, Kortsalioudaki C, Scott S, et al. (2012) Lancet 379: 547-556.
6. Smith A, Saiman L, Zhou J, et al. (2010) Pediatr Infect Dis J 29: 831-835.
7. Stoll B J, Hansen N I, Sanchez P J, et al. (2011) Pediatrics 127: 817-826.
8. Tazi A, Disson O, Bellais S, et al. (2010) J Exp Med 207: 313-2322.
9. Hornik C P, Fort P, Clark R H, et al. (2012) Early Hum Dev 88 Suppl 2: S69-74.
10. Kronforst K D, Mancuso C J, Pettengill M, et al. (2012) PLoS One 7: e43897.
11. Bourgeois-Nicolaos N, Cordier A G, Guillet-Caruba C, et al. (2013) J Clin Microbiol 51(4): 1305-6.
12. Watson R S, Carcillo J A, Linde-Zwirble W T, et al. (2003) Am J Respir Crit Care Med 167: 695-701.
13. Carr R, Brocklehurst P, Dore C J, et al. (2009) Lancet 373: 226-233.
14. Goldenberg R L, Hauth J C, Andrews W W (2000) N Engl J Med 342: 1500-1507.
15. Kaufman D, Fairchild K D (2004) Clin Microbiol Rev 17: 638-680, table of contents.
16. Stoll B J, Hansen N, Fanaroff A A, et al. (2002) N Engl J Med 347: 240-247.
17. Stoll B J, Hansen N I, Higgins R D, et al. (2005) Pediatr Infect Dis J 24: 635-639.
18. Bishton M, Chopra R (2004) Br J Haematol 127: 501-508.
19. Groselj-Grenc M, Ihan A, Pavenik-Arnol M, et al. (2009) Intensive Care Med 35: 1950-1958.
20. Melvan J N, Bagby G J, Welsh D A, et al. (2010) Int Rev Immunol 29: 315-348.
21. Pammi M, Brocklehurst P (2011) Cochrane Database Syst Rev: CDoo3956.
22. Shann F (2009) Lancet 373: 188-190.
23. Wynn J L, Levy O (2010) Clin Perinatol 37: 307-337.
24. Madureira P, Andrade E B, Gama B, et al. (2011) PLoS Pathog 7: e1002363.
25. Madureira P, Baptista M, Vieira M, et al. (2007) J Immunol 178: 1379-1387.
26. Heppner H J, Cornel S, Peter W, et al. (2013) Crit Clin Care 29: 757-774.
27. Dellinger R P, Levy M M, Carlet J M, et al. (2008) Crit Care Med 36: 296-327.
28. Linden P K (2009) Infect Dis Clin North Am 23: 535-556.
29. Brun-Buisson C, Doyon F, Carlet J, et al. (1995) JAMA 274: 968-974.
30. Jacobsson G, Dashti S, Wahlberg T, et al. (2007) Scand J Infect Dis 39: 6-13.
31. Skoff T H, Farley M M, Petit S, et al. (2009) Clin Infect Dis 49: 85-92.
32. Lin Y T, Wang F D, Wu P F, et al. (2013) BMC Infect Dis 13: 56.
33. Seifert K N, McArthur W P, Bleiweis A S, et al. (2003) Can J Microbiol (5): 350-6.
34. Aguilera L, Ferreira E, Gimenez R, et al. (2012) Int J Biochem Cell Biol 44(6): 955-962.
35. Aguilera L, Gimenez R, Badia J, et al. (2009) Int Microbiol 12(3): 187-192.
36. Egea L, Aguilera L, Gimenez R, et al. (2007) Int J Biochem Cell Biol 39(6): 1190-1203
37. Kerro-Dego O, Prysliak T, Perez-Casal J, et al. (2012) Vet Microbiol 156(3-4): 443-447.
38. Purves J, Cockayne A, Moody P C, et al. (2010) Infect Immun 78(12): 5223-5232.
39. Goji N, Potter A A, Perez-Casal J (2004) Vet Microbiol 99(3-4): 269-279.
40. Ling E, Feldman G, Portnoi M, et al. (2004) Clin Exp Immunol 138(2): 290-298.
41. Madureira P, Baptista M, Vieira M, et al. (2007) J Immunol 178(3): 1379-87.
42. Andrade E B, Alves J, Madureira P, et al. (2013) J Immunol 191(9): 4759-4768.
43. Henneke P, Dramsi S, Mancuso G, et al. (2008) J Immunol 180: 6149-6158.
44. Machata S, Tchatalbachev S, Mohamed W, et al. (2008) J Immunol 181: 2028-2035.
45. Vosshenrich C A, Cumano A, Muller W, et al. (2003) Nat Immunol 4(8): 773-779.
46. Johri A K, Paoletti L C, Glaser P, et al. (2006) Nat Rev Microbiol 4: 932-942.
47. Doran K S, Nizet V (2004) Mol Microbiol 54: 23-31.
48. Thompson J D, Higgins D G, Gibson T J (1994) Nucleic Acids Res 22(22): 4673-4680.
49. Thompson J D, Gibson T J, Plewniak F, et al. (1997) Nucleic Acids Res 25(24): 4876-4882.
50. Tushinski R J, Oliver I T, Guilbert L J, et al. (1982) Cell 28: 71-81.
51. Tunio S A, Oldfield N J, Ala'Aldeen D A, et al. (2010) BMC Microbiol 10:280.
52. Goldenberg R L, McClure E M, Saleem S, et al. (2010) Lancet 375: 1482-1490.
53. Lawn J E, Cousens S, Zupan J (2005) Lancet 365: 891-900.
54. Barton L, Hodgman J E, Pavlova Z (1999) Pediatrics 103: 446-451.
55. Mulholland E K, Adegbola R A (2005) N Engl J Med 352: 75-77.
56. Schrag S J (2011) Lancet 378: 11-12.

The invention claimed is:

1. An isolated peptide that has at least 95% amino acid sequence identity to any one of SEQ ID NOs: 26-33.

2. The isolated peptide of claim 1, wherein the isolated peptide is conjugated to a carrier protein.

* * * * *

SEQUENCE LISTING

<160> NUMBER OF SEQ ID NOS: 74

<210> SEQ ID NO 1
<211> LENGTH: 336
<212> TYPE: PRT
<213> ORGANISM: Streptococcus agalactiae

<400> SEQUENCE: 1

Met Val Val Lys Val Gly Ile Asn Gly Phe Gly Arg Ile Gly Arg Leu
1               5                   10                  15

Ala Phe Arg Arg Ile Gln Asn Val Glu Gly Val Glu Val Thr Arg Ile
            20                  25                  30

Asn Asp Leu Thr Asp Pro Asn Met Leu Ala His Leu Leu Lys Tyr Asp
        35                  40                  45

Thr Thr Gln Gly Arg Phe Asp Gly Thr Val Glu Val Lys Glu Gly Gly
    50                  55                  60

Phe Glu Val Asn Gly Gln Phe Val Lys Val Ser Ala Glu Arg Glu Pro
65                  70                  75                  80

Ala Asn Ile Asp Trp Ala Thr Asp Gly Val Glu Ile Val Leu Glu Ala
                85                  90                  95

Thr Gly Phe Phe Ala Ser Lys Glu Lys Ala Glu Gln His Ile His Glu
            100                 105                 110

Asn Gly Ala Lys Lys Val Val Ile Thr Ala Pro Gly Gly Asn Asp Val
        115                 120                 125

Lys Thr Val Val Phe Asn Thr Asn His Asp Ile Leu Asp Gly Thr Glu
    130                 135                 140

Thr Val Ile Ser Gly Ala Ser Cys Thr Thr Asn Cys Leu Ala Pro Met
145                 150                 155                 160

Ala Lys Ala Leu Gln Asp Asn Phe Gly Val Lys Gln Gly Leu Met Thr
                165                 170                 175

Thr Ile His Ala Tyr Thr Gly Asp Gln Met Ile Leu Asp Gly Pro His
            180                 185                 190

Arg Gly Gly Asp Leu Arg Arg Ala Arg Ala Gly Ala Ala Asn Ile Val
        195                 200                 205

Pro Asn Ser Thr Gly Ala Ala Lys Ala Ile Gly Leu Val Ile Pro Glu
    210                 215                 220

Leu Asn Gly Lys Leu Asp Gly Ala Ala Gln Arg Val Pro Val Pro Thr
225                 230                 235                 240

Gly Ser Val Thr Glu Leu Val Ala Thr Leu Glu Lys Asp Val Thr Val
                245                 250                 255

Glu Glu Val Asn Ala Ala Met Lys Ala Ala Ala Asn Asp Ser Tyr Gly
            260                 265                 270

Tyr Thr Glu Asp Pro Ile Val Ser Ser Asp Ile Val Gly Ile Ser Tyr
        275                 280                 285

Gly Ser Leu Phe Asp Ala Thr Gln Thr Lys Val Gln Thr Val Asp Gly
    290                 295                 300

Asn Gln Leu Val Lys Val Val Ser Trp Tyr Asp Asn Glu Met Ser Tyr
305                 310                 315                 320

Thr Ser Gln Leu Val Arg Thr Leu Glu Tyr Phe Ala Lys Ile Ala Lys
                325                 330                 335

<210> SEQ ID NO 2
<211> LENGTH: 333
<212> TYPE: PRT
<213> ORGANISM: Escherichia coli

<400> SEQUENCE: 2

Met Ser Lys Val Gly Ile Asn Gly Phe Gly Arg Ile Gly Arg Leu Val
1               5                   10                  15

Leu Arg Arg Leu Leu Glu Val Lys Ser Asn Ile Asp Val Val Ala Ile
            20                  25                  30

Asn Asp Leu Thr Ser Pro Lys Ile Leu Ala Tyr Leu Leu Lys His Asp
        35                  40                  45

Ser Asn Tyr Gly Pro Phe Pro Trp Ser Val Asp Tyr Thr Glu Asp Ser
    50                  55                  60

Leu Ile Val Asn Gly Lys Ser Ile Ala Val Tyr Ala Glu Lys Glu Ala
65                  70                  75                  80

Lys Asn Ile Pro Trp Lys Ala Lys Gly Ala Glu Ile Ile Val Glu Cys
            85                  90                  95

Thr Gly Phe Tyr Thr Ser Ala Glu Lys Ser Gln Ala His Leu Asp Ala
        100                 105                 110

Gly Ala Lys Lys Val Leu Ile Ser Ala Pro Ala Gly Glu Met Lys Thr
    115                 120                 125

Ile Val Tyr Asn Val Asn Asp Asp Thr Leu Asp Gly Asn Asp Thr Ile
130                 135                 140

Val Ser Val Ala Ser Cys Thr Thr Asn Cys Leu Ala Pro Met Ala Lys
145                 150                 155                 160

Ala Leu His Asp Ser Phe Gly Ile Glu Val Gly Thr Met Thr Thr Ile
            165                 170                 175

His Ala Tyr Thr Gly Thr Gln Ser Leu Val Asp Gly Pro Arg Gly Lys
        180                 185                 190

Asp Leu Arg Ala Ser Arg Ala Ala Ala Glu Asn Ile Ile Pro His Thr
    195                 200                 205

Thr Gly Ala Ala Lys Ala Ile Gly Leu Val Ile Pro Glu Leu Ser Gly
210                 215                 220

Lys Leu Lys Gly His Ala Gln Arg Val Pro Val Lys Thr Gly Ser Val
225                 230                 235                 240

Thr Glu Leu Val Ser Ile Leu Gly Lys Lys Val Thr Ala Glu Glu Val
            245                 250                 255

Asn Asn Ala Leu Lys Lys Ala Thr Asn Asn Glu Ser Phe Gly Tyr
        260                 265                 270

Thr Asp Glu Glu Ile Val Ser Ser Asp Ile Ile Gly Ser His Phe Gly
    275                 280                 285

Ser Val Phe Asp Ala Thr Gln Thr Glu Ile Thr Ala Val Gly Asp Leu
290                 295                 300

Gln Leu Val Lys Thr Val Ala Trp Tyr Asp Asn Glu Tyr Gly Phe Val
305                 310                 315                 320

Thr Gln Leu Ile Arg Thr Leu Glu Lys Phe Ala Lys Leu
            325                 330

<210> SEQ ID NO 3
<211> LENGTH: 336
<212> TYPE: PRT
<213> ORGANISM: Staphylococcus aureus

<400> SEQUENCE: 3

Met Ala Val Lys Val Ala Ile Asn Gly Phe Gly Arg Ile Gly Arg Leu
1               5                   10                  15

Ala Phe Arg Arg Ile Gln Glu Val Glu Gly Leu Glu Val Val Ala Val
            20                  25                  30

```
Asn Asp Leu Thr Asp Asp Met Leu Ala His Leu Leu Lys Tyr Asp
            35                  40                  45

Thr Met Gln Gly Arg Phe Thr Gly Glu Val Glu Val Asp Gly Gly
 50                  55                  60

Phe Arg Val Asn Gly Lys Glu Val Lys Ser Phe Ser Glu Pro Asp Ala
 65                  70                  75                  80

Ser Lys Leu Pro Trp Lys Asp Leu Asn Ile Asp Val Val Leu Glu Cys
                 85                  90                  95

Thr Gly Phe Tyr Thr Asp Lys Asp Lys Ala Gln Ala His Ile Glu Ala
               100                 105                 110

Gly Ala Lys Lys Val Leu Ile Ser Ala Pro Ala Thr Gly Asp Leu Lys
               115                 120                 125

Thr Ile Val Phe Asn Thr Asn His Gln Glu Leu Asp Gly Ser Glu Thr
130                 135                 140

Val Val Ser Gly Ala Ser Cys Thr Thr Asn Ser Leu Ala Pro Val Ala
145                 150                 155                 160

Lys Val Leu Asn Asp Asp Phe Gly Leu Val Glu Gly Leu Met Thr Thr
                165                 170                 175

Ile His Ala Tyr Thr Gly Asp Gln Asn Thr Gln Asp Ala Pro His Arg
                180                 185                 190

Lys Gly Asp Lys Arg Arg Ala Arg Ala Ala Ala Glu Asn Ile Ile Pro
                195                 200                 205

Asn Ser Thr Gly Ala Ala Lys Ala Ile Gly Lys Val Ile Pro Glu Ile
    210                 215                 220

Asp Gly Lys Leu Asp Gly Gly Ala Gln Arg Val Pro Val Ala Thr Gly
225                 230                 235                 240

Ser Leu Thr Glu Leu Thr Val Val Leu Glu Lys Gln Asp Val Thr Val
                245                 250                 255

Glu Gln Val Asn Glu Ala Met Lys Asn Ala Ser Asn Glu Ser Phe Gly
                260                 265                 270

Tyr Thr Glu Asp Glu Ile Val Ser Ser Asp Val Val Gly Met Thr Tyr
                275                 280                 285

Gly Ser Leu Phe Asp Ala Thr Gln Thr Arg Val Met Ser Val Gly Asp
290                 295                 300

Arg Gln Leu Val Lys Val Ala Ala Trp Tyr Asp Asn Glu Met Ser Tyr
305                 310                 315                 320

Thr Ala Gln Leu Val Arg Thr Leu Ala Tyr Leu Ala Glu Leu Ser Lys
                325                 330                 335

<210> SEQ ID NO 4
<211> LENGTH: 335
<212> TYPE: PRT
<213> ORGANISM: Streptococcus pneumoniae

<400> SEQUENCE: 4

Met Val Val Lys Val Gly Ile Asn Gly Phe Gly Arg Ile Gly Arg Leu
  1               5                  10                  15

Ala Phe Arg Arg Ile Gln Asn Val Glu Gly Val Glu Val Thr Arg Ile
                 20                  25                  30

Asn Asp Leu Thr Asp Pro Val Met Leu Ala His Leu Leu Lys Tyr Asp
                 35                  40                  45

Thr Thr Gln Gly Arg Phe Asp Gly Thr Val Glu Val Lys Glu Gly Gly
 50                  55                  60

Phe Glu Val Asn Gly Lys Phe Ile Lys Val Ser Ala Glu Arg Asp Pro
 65                  70                  75                  80
```

Glu Gln Ile Asp Trp Ala Thr Asp Gly Val Glu Ile Val Leu Glu Ala
                85                  90                  95

Thr Gly Phe Phe Ala Lys Lys Glu Ala Ala Glu Lys His Leu Lys Gly
            100                 105                 110

Gly Ala Lys Lys Val Val Ile Thr Ala Pro Gly Gly Asn Asp Val Lys
        115                 120                 125

Thr Val Val Phe Asn Thr Asn His Asp Val Leu Asp Gly Thr Glu Thr
    130                 135                 140

Val Ile Ser Gly Ala Ser Cys Thr Thr Asn Cys Leu Ala Pro Met Ala
145                 150                 155                 160

Lys Ala Leu Gln Asp Asn Phe Gly Val Val Glu Gly Leu Met Thr Thr
                165                 170                 175

Ile His Ala Tyr Thr Gly Asp Gln Met Ile Leu Asp Gly Pro His Arg
            180                 185                 190

Gly Gly Asp Leu Arg Arg Ala Arg Ala Gly Ala Ala Asn Ile Val Pro
        195                 200                 205

Asn Ser Thr Gly Ala Ala Lys Ala Ile Gly Leu Val Ile Pro Glu Leu
    210                 215                 220

Asn Gly Lys Leu Asp Gly Ser Ala Gln Arg Val Pro Thr Pro Thr Gly
225                 230                 235                 240

Ser Val Thr Glu Leu Val Ala Val Leu Glu Lys Asn Val Thr Val Asp
                245                 250                 255

Glu Val Asn Ala Ala Met Lys Ala Ala Ser Asn Glu Ser Tyr Gly Tyr
            260                 265                 270

Thr Glu Asp Pro Ile Val Ser Ser Asp Ile Val Gly Met Ser Tyr Gly
        275                 280                 285

Ser Leu Phe Asp Ala Thr Gln Thr Lys Val Leu Asp Val Asp Gly Lys
    290                 295                 300

Gln Leu Val Lys Val Val Ser Trp Tyr Asp Asn Glu Met Ser Tyr Thr
305                 310                 315                 320

Ala Gln Leu Val Arg Thr Leu Glu Tyr Phe Ala Lys Ile Ala Lys
                325                 330                 335

<210> SEQ ID NO 5
<211> LENGTH: 332
<212> TYPE: PRT
<213> ORGANISM: Klebsiella pneumoniae

<400> SEQUENCE: 5

Met Ser Lys Leu Gly Ile Asn Gly Phe Gly Arg Ile Gly Arg Leu Val
1               5                   10                  15

Leu Arg Arg Leu Leu Glu Val Asp Ser Ser Leu Glu Val Val Ala Ile
            20                  25                  30

Asn Asp Leu Thr Ser Pro Lys Val Leu Ala Tyr Leu Leu Lys His Asp
        35                  40                  45

Ser Asn Tyr Gly Pro Phe Pro Trp Ser Val Asp Phe Thr Glu Asp Ala
    50                  55                  60

Leu Ile Val Asn Gly Lys Thr Ile Thr Val Tyr Ala Glu Lys Glu Ala
65                  70                  75                  80

Gln His Ile Pro Trp Gln Ala Ala Gly Ala Glu Val Ile Val Glu Cys
                85                  90                  95

Thr Gly Phe Tyr Thr Ser Ala Glu Lys Ser Gln Ala His Ile Gln Ala
            100                 105                 110

Gly Ala Arg Lys Val Leu Ile Ser Ala Pro Ala Gly Glu Met Lys Thr

```
            115                 120                 125
Ile Val Tyr Asn Val Asn Asp Asp Thr Leu Thr Pro Asp Asp Thr Ile
130                 135                 140

Ile Ser Val Ala Ser Cys Thr Thr Asn Cys Leu Ala Pro Met Ala Lys
145                 150                 155                 160

Val Leu Gln Asp Ala Phe Gly Ile Thr Val Gly Thr Met Thr Thr Ile
                    165                 170                 175

His Ala Tyr Thr Gly Thr Gln Ser Leu Val Asp Gly Pro Arg Gly Lys
                180                 185                 190

Asp Leu Arg Ala Ser Arg Ala Ala Glu Asn Val Ile Pro His Thr
            195                 200                 205

Thr Gly Ala Ala Lys Ala Ile Gly Leu Val Ile Pro Ala Leu Ser Gly
210                 215                 220

Lys Leu Lys Gly His Ala Gln Arg Val Pro Thr Lys Thr Gly Ser Val
225                 230                 235                 240

Thr Glu Leu Val Ser Val Leu Glu Lys Val Thr Ala Asp Glu Val
                    245                 250                 255

Asn Gln Ala Met Lys Gln Ala Ala Glu Gly Asn Glu Ser Phe Gly Tyr
                260                 265                 270

Thr Glu Glu Ile Val Ser Ser Asp Ile Ile Gly Ser His Phe Gly
                275                 280                 285

Ser Ile Tyr Asp Ala Thr Gln Leu Glu Ile Val Glu Ala Gly Gly Val
            290                 295                 300

Gln Leu Val Lys Thr Val Ala Trp Tyr Asp Asn Glu Tyr Gly Phe Val
305                 310                 315                 320

Thr Gln Leu Ile Arg Val Leu Glu Lys Phe Ala Arg
                    325                 330

<210> SEQ ID NO 6
<211> LENGTH: 334
<212> TYPE: PRT
<213> ORGANISM: Pseudomonas aeruginosa

<400> SEQUENCE: 6

Met Thr Ile Arg Leu Ala Ile Asn Gly Phe Gly Arg Ile Gly Arg Asn
1               5                   10                  15

Val Leu Arg Ala Leu Tyr Thr Gly His Tyr Arg Glu Gln Leu Gln Val
                20                  25                  30

Val Ala Ile Asn Asp Leu Gly Asp Ala Ala Val Asn Ala His Leu Phe
            35                  40                  45

Gln Tyr Asp Ser Val His Gly His Phe Pro Gly Glu Val His Asp
50                  55                  60

Ala Glu Ser Leu Arg Val Met Gly Asp Arg Ile Ala Val Ser Ala Ile
65                  70                  75                  80

Arg Asn Pro Ala Glu Leu Pro Trp Lys Ser Leu Gly Val Asp Ile Val
                85                  90                  95

Leu Glu Cys Thr Gly Leu Phe Thr Ser Arg Asp Lys Ala Ala Ala His
                100                 105                 110

Leu Gln Ala Gly Ala Gly Lys Val Leu Ile Ser Ala Pro Gly Lys Asp
            115                 120                 125

Val Glu Ala Thr Val Val Tyr Gly Val Asn His Glu Val Leu Arg Ala
            130                 135                 140

Ser His Arg Ile Val Ser Asn Ala Ser Cys Thr Thr Asn Cys Leu Ala
145                 150                 155                 160
```

```
Pro Val Ala Gln Val Leu His Arg Glu Leu Gly Ile Glu His Gly Leu
                165                 170                 175

Met Thr Thr Ile His Ala Tyr Thr Asn Asp Gln Asn Leu Ser Asp Val
            180                 185                 190

Tyr His Pro Asp Leu Tyr Arg Ala Arg Ser Ala Thr Gln Ser Met Ile
        195                 200                 205

Pro Thr Lys Thr Gly Ala Ala Glu Ala Val Gly Leu Val Leu Pro Glu
    210                 215                 220

Leu Ala Gly Lys Leu Thr Gly Leu Ala Val Arg Val Pro Val Ile Asn
225                 230                 235                 240

Val Ser Leu Val Asp Leu Thr Val Gln Val Ala Arg Asp Thr Ser Val
                245                 250                 255

Asp Glu Val Asn Arg Leu Leu Arg Glu Ala Ser Glu Gly Ser Pro Val
            260                 265                 270

Leu Gly Tyr Asn Thr Gln Pro Leu Val Ser Val Asp Phe Asn His Asp
        275                 280                 285

Pro Arg Ser Ser Ile Phe Asp Ala Asn His Thr Lys Val Ser Gly Arg
    290                 295                 300

Leu Val Lys Ala Met Ala Trp Tyr Asp Asn Glu Trp Gly Phe Ser Asn
305                 310                 315                 320

Arg Met Leu Asp Ser Ala Leu Ala Leu Ala Ala Arg Asp
                325                 330

<210> SEQ ID NO 7
<211> LENGTH: 334
<212> TYPE: PRT
<213> ORGANISM: Neisseria meningitidis (group B)

<400> SEQUENCE: 7

Met Ser Ile Lys Val Ala Ile Asn Gly Phe Gly Arg Ile Gly Arg Leu
1               5                   10                  15

Ala Leu Arg Gln Ile Glu Lys Ala His Asp Ile Glu Val Val Ala Val
                20                  25                  30

Asn Asp Leu Thr Pro Ala Glu Met Leu Leu His Leu Phe Lys Tyr Asp
            35                  40                  45

Ser Thr Gln Gly Arg Phe Gln Gly Thr Ala Glu Leu Lys Asp Asp Ala
        50                  55                  60

Ile Val Val Asn Gly Lys Glu Ile Lys Val Phe Ala Asn Pro Asn Pro
65                  70                  75                  80

Glu Glu Leu Pro Trp Gly Glu Leu Gly Val Asp Val Ile Leu Glu Cys
                85                  90                  95

Thr Gly Phe Phe Thr Asn Lys Thr Lys Ala Glu Ala His Ile Arg Ala
            100                 105                 110

Gly Ala Arg Lys Val Val Ile Ser Ala Pro Gly Gly Asn Asp Val Lys
        115                 120                 125

Thr Val Val Tyr Gly Val Asn Gln Asp Ile Leu Asp Gly Ser Glu Thr
    130                 135                 140

Val Ile Ser Ala Ala Ser Cys Thr Thr Asn Cys Leu Ala Pro Met Ala
145                 150                 155                 160

Ala Val Leu Gln Lys Glu Phe Gly Val Val Glu Gly Leu Met Thr Thr
                165                 170                 175

Ile His Ala Tyr Thr Gly Asp Gln Asn Thr Leu Asp Ala Pro His Arg
            180                 185                 190

Lys Gly Asp Leu Arg Arg Ala Arg Ala Ala Ala Leu Asn Ile Val Pro
        195                 200                 205
```

```
Asn Ser Thr Gly Ala Ala Lys Ala Ile Gly Leu Val Ile Pro Glu Leu
    210                 215                 220

Asn Gly Lys Leu Asp Gly Ser Ala Gln Arg Val Pro Val Ala Ser Gly
225                 230                 235                 240

Ser Leu Thr Glu Leu Val Ser Ile Leu Glu Arg Pro Val Thr Lys Glu
            245                 250                 255

Glu Ile Asn Ala Ala Met Lys Ala Ala Ala Ser Glu Ser Tyr Gly Tyr
        260                 265                 270

Asn Glu Asp Gln Ile Val Ser Ser Asp Val Val Gly Ile Glu Tyr Gly
    275                 280                 285

Ser Leu Phe Asp Ala Thr Gln Thr Arg Val Met Thr Val Gly Gly Lys
290                 295                 300

Gln Leu Val Lys Thr Val Ala Trp Tyr Asp Asn Glu Met Ser Tyr Thr
305                 310                 315                 320

Cys Gln Leu Val Arg Thr Leu Glu Tyr Phe Ala Gly Lys Ile
            325                 330
```

<210> SEQ ID NO 8
<211> LENGTH: 335
<212> TYPE: PRT
<213> ORGANISM: Homo sapiens

<400> SEQUENCE: 8

```
Met Gly Lys Val Lys Val Gly Val Asn Gly Phe Gly Arg Ile Gly Arg
1               5                   10                  15

Leu Val Thr Arg Ala Ala Phe Asn Ser Gly Lys Val Asp Ile Val Ala
            20                  25                  30

Ile Asn Asp Pro Phe Ile Asp Leu Asn Tyr Met Val Tyr Met Phe Gln
        35                  40                  45

Tyr Asp Ser Thr His Gly Lys Phe His Gly Thr Val Lys Ala Glu Asn
    50                  55                  60

Gly Lys Leu Val Ile Asn Gly Asn Pro Ile Thr Ile Phe Gln Glu Arg
65                  70                  75                  80

Asp Pro Ser Lys Ile Lys Trp Gly Asp Ala Gly Ala Glu Tyr Val Val
                85                  90                  95

Glu Ser Thr Gly Val Phe Thr Thr Met Glu Lys Ala Gly Ala His Leu
            100                 105                 110

Gln Gly Gly Ala Lys Arg Val Ile Ile Ser Ala Pro Ser Ala Asp Ala
        115                 120                 125

Pro Met Phe Val Met Gly Val Asn His Glu Lys Tyr Asp Asn Ser Leu
    130                 135                 140

Lys Ile Ile Ser Asn Ala Ser Cys Thr Thr Asn Cys Leu Ala Pro Leu
145                 150                 155                 160

Ala Lys Val Ile His Asp Asn Phe Gly Ile Val Glu Gly Leu Met Thr
                165                 170                 175

Thr Val His Ala Ile Thr Ala Thr Gln Lys Thr Val Asp Gly Pro Ser
            180                 185                 190

Gly Lys Leu Trp Arg Asp Gly Arg Gly Ala Leu Gln Asn Ile Ile Pro
        195                 200                 205

Ala Ser Thr Gly Ala Ala Lys Ala Val Gly Lys Val Ile Pro Glu Leu
    210                 215                 220

Asn Gly Lys Leu Thr Gly Met Ala Phe Arg Val Pro Thr Ala Asn Val
225                 230                 235                 240

Ser Val Val Asp Leu Thr Cys Arg Leu Glu Lys Pro Ala Lys Tyr Asp
```

```
                    245                 250                 255

Asp Ile Lys Lys Val Val Lys Gln Ala Ser Glu Gly Pro Leu Lys Gly
            260                 265                 270

Ile Leu Gly Tyr Thr Glu His Gln Val Val Ser Ser Asp Phe Asn Ser
        275                 280                 285

Asp Thr His Ser Ser Thr Phe Asp Ala Gly Ala Gly Ile Ala Leu Asn
    290                 295                 300

Asp His Phe Val Lys Leu Ile Ser Trp Tyr Asp Asn Glu Phe Gly Tyr
305                 310                 315                 320

Ser Asn Arg Val Val Asp Leu Met Ala His Met Ala Ser Lys Glu
                325                 330                 335

<210> SEQ ID NO 9
<211> LENGTH: 12
<212> TYPE: PRT
<213> ORGANISM: Artificial Sequence
<220> FEATURE:
<223> OTHER INFORMATION: Peptide 1

<400> SEQUENCE: 9

Arg Ile Gln Glu Val Glu Gly Leu Glu Val Thr Arg
1               5                   10

<210> SEQ ID NO 10
<211> LENGTH: 10
<212> TYPE: PRT
<213> ORGANISM: Streptococcus agalactiae

<400> SEQUENCE: 10

Asp Val Thr Val Glu Glu Asn Ala Ala Met
1               5                   10

<210> SEQ ID NO 11
<211> LENGTH: 13
<212> TYPE: PRT
<213> ORGANISM: Artificial Sequence
<220> FEATURE:
<223> OTHER INFORMATION: Peptide 3

<400> SEQUENCE: 11

Glu Val Lys Asp Gly His Leu Ile Val Asn Gly Lys Val
1               5                   10

<210> SEQ ID NO 12
<211> LENGTH: 13
<212> TYPE: PRT
<213> ORGANISM: Pseudomonas aeruginosa

<400> SEQUENCE: 12

Glu His Asp Ala Glu Ser Leu Arg Val Met Gly Asp Arg
1               5                   10

<210> SEQ ID NO 13
<211> LENGTH: 15
<212> TYPE: PRT
<213> ORGANISM: Streptococcus agalactiae

<400> SEQUENCE: 13

Ala Phe Arg Arg Ile Gln Asn Val Glu Gly Val Glu Val Thr Arg
1               5                   10                  15

<210> SEQ ID NO 14
<211> LENGTH: 18
```

```
<212> TYPE: PRT
<213> ORGANISM: Streptococcus agalactiae

<400> SEQUENCE: 14

Glu Val Lys Glu Gly Gly Phe Glu Val Asn Gly Gln Phe Val Lys Val
1               5                   10                  15

Ser Ala

<210> SEQ ID NO 15
<211> LENGTH: 15
<212> TYPE: PRT
<213> ORGANISM: Streptococcus agalactiae

<400> SEQUENCE: 15

Thr Gln Thr Lys Val Gln Thr Val Asp Gly Asn Gln Leu Val Lys
1               5                   10                  15

<210> SEQ ID NO 16
<211> LENGTH: 14
<212> TYPE: PRT
<213> ORGANISM: Streptococcus agalactiae

<400> SEQUENCE: 16

His Arg Gly Gly Asp Leu Arg Arg Ala Arg Ala Gly Ala Ala
1               5                   10

<210> SEQ ID NO 17
<211> LENGTH: 16
<212> TYPE: PRT
<213> ORGANISM: Streptococcus agalactiae

<400> SEQUENCE: 17

Val Glu Glu Val Asn Ala Ala Met Lys Ala Ala Ala Asn Asp Ser Tyr
1               5                   10                  15

<210> SEQ ID NO 18
<211> LENGTH: 15
<212> TYPE: PRT
<213> ORGANISM: Streptococcus agalactiae

<400> SEQUENCE: 18

Ser Gln Leu Val Arg Thr Leu Glu Tyr Phe Ala Lys Ile Ala Lys
1               5                   10                  15

<210> SEQ ID NO 19
<211> LENGTH: 14
<212> TYPE: PRT
<213> ORGANISM: Escherichia coli

<400> SEQUENCE: 19

Leu Arg Arg Leu Leu Glu Val Lys Ser Asn Ile Asp Val Val
1               5                   10

<210> SEQ ID NO 20
<211> LENGTH: 14
<212> TYPE: PRT
<213> ORGANISM: Escherichia coli

<400> SEQUENCE: 20

Pro Trp Ser Val Asp Tyr Thr Glu Asp Ser Leu Ile Val Asn
1               5                   10

<210> SEQ ID NO 21
<211> LENGTH: 16
```

<212> TYPE: PRT
<213> ORGANISM: Escherichia coli

<400> SEQUENCE: 21

Ala Gly Glu Met Lys Thr Ile Val Tyr Asn Val Asn Asp Asp Thr Leu
1               5                   10                  15

<210> SEQ ID NO 22
<211> LENGTH: 14
<212> TYPE: PRT
<213> ORGANISM: Escherichia coli

<400> SEQUENCE: 22

Gly Lys Lys Val Thr Ala Glu Glu Val Asn Asn Ala Leu Lys
1               5                   10

<210> SEQ ID NO 23
<211> LENGTH: 14
<212> TYPE: PRT
<213> ORGANISM: Escherichia coli

<400> SEQUENCE: 23

Thr Asn Asn Asn Glu Ser Phe Gly Tyr Thr Asp Glu Glu Ile
1               5                   10

<210> SEQ ID NO 24
<211> LENGTH: 18
<212> TYPE: PRT
<213> ORGANISM: Escherichia coli

<400> SEQUENCE: 24

Thr Gln Thr Glu Ile Thr Ala Val Gly Asp Leu Gln Leu Val Lys Thr
1               5                   10                  15

Val Ala

<210> SEQ ID NO 25
<211> LENGTH: 17
<212> TYPE: PRT
<213> ORGANISM: Escherichia coli

<400> SEQUENCE: 25

Tyr Gly Phe Val Thr Gln Leu Ile Arg Thr Leu Glu Lys Phe Ala Lys
1               5                   10                  15

Leu

<210> SEQ ID NO 26
<211> LENGTH: 16
<212> TYPE: PRT
<213> ORGANISM: Staphylococcus aureus

<400> SEQUENCE: 26

Leu Thr Asp Asp Asp Met Leu Ala His Leu Leu Lys Tyr Asp Thr Met
1               5                   10                  15

<210> SEQ ID NO 27
<211> LENGTH: 16
<212> TYPE: PRT
<213> ORGANISM: Staphylococcus aureus

<400> SEQUENCE: 27

Glu Val Val Asp Gly Gly Phe Arg Val Asn Gly Lys Glu Val Lys Ser
1               5                   10                  15

```
<210> SEQ ID NO 28
<211> LENGTH: 13
<212> TYPE: PRT
<213> ORGANISM: Staphylococcus aureus

<400> SEQUENCE: 28

Ala Thr Gly Asp Leu Lys Thr Ile Val Phe Asn Thr Asn
1               5                   10

<210> SEQ ID NO 29
<211> LENGTH: 13
<212> TYPE: PRT
<213> ORGANISM: Staphylococcus aureus

<400> SEQUENCE: 29

His Arg Lys Gly Asp Lys Arg Arg Ala Arg Ala Ala Ala
1               5                   10

<210> SEQ ID NO 30
<211> LENGTH: 20
<212> TYPE: PRT
<213> ORGANISM: Staphylococcus aureus

<400> SEQUENCE: 30

Gln Asp Val Thr Val Glu Gln Val Asn Glu Ala Met Lys Asn Ala Ser
1               5                   10                  15

Asn Glu Ser Phe
            20

<210> SEQ ID NO 31
<211> LENGTH: 16
<212> TYPE: PRT
<213> ORGANISM: Staphylococcus aureus

<400> SEQUENCE: 31

Val Glu Gln Val Asn Glu Ala Met Lys Asn Ala Ser Asn Glu Ser Phe
1               5                   10                  15

<210> SEQ ID NO 32
<211> LENGTH: 18
<212> TYPE: PRT
<213> ORGANISM: Staphylococcus aureus

<400> SEQUENCE: 32

Thr Gln Thr Arg Val Met Ser Val Gly Asp Arg Gln Leu Val Lys Val
1               5                   10                  15

Ala Ala

<210> SEQ ID NO 33
<211> LENGTH: 18
<212> TYPE: PRT
<213> ORGANISM: Staphylococcus aureus

<400> SEQUENCE: 33

Ser Tyr Thr Ala Gln Leu Val Arg Thr Leu Ala Tyr Leu Ala Glu Leu
1               5                   10                  15

Ser Lys

<210> SEQ ID NO 34
<211> LENGTH: 15
<212> TYPE: PRT
<213> ORGANISM: Streptococcus pneumoniae

<400> SEQUENCE: 34
```

Ala Phe Arg Arg Ile Gln Asn Val Glu Gly Val Glu Val Thr Arg
1               5                   10                  15

<210> SEQ ID NO 35
<211> LENGTH: 14
<212> TYPE: PRT
<213> ORGANISM: Streptococcus pneumoniae

<400> SEQUENCE: 35

Asp Leu Thr Asp Pro Val Met Leu Ala His Leu Leu Lys Tyr
1               5                   10

<210> SEQ ID NO 36
<211> LENGTH: 18
<212> TYPE: PRT
<213> ORGANISM: Streptococcus pneumoniae

<400> SEQUENCE: 36

Glu Val Lys Glu Gly Gly Phe Glu Val Asn Gly Lys Phe Ile Lys Val
1               5                   10                  15

Ser Ala

<210> SEQ ID NO 37
<211> LENGTH: 17
<212> TYPE: PRT
<213> ORGANISM: Streptococcus pneumoniae

<400> SEQUENCE: 37

Gly Gly Asn Asp Val Lys Thr Val Val Phe Asn Thr Asn His Asp Val
1               5                   10                  15

Leu

<210> SEQ ID NO 38
<211> LENGTH: 15
<212> TYPE: PRT
<213> ORGANISM: Streptococcus pneumoniae

<400> SEQUENCE: 38

Pro His Arg Gly Gly Asp Leu Arg Arg Ala Arg Ala Gly Ala Ala
1               5                   10                  15

<210> SEQ ID NO 39
<211> LENGTH: 19
<212> TYPE: PRT
<213> ORGANISM: Streptococcus pneumoniae

<400> SEQUENCE: 39

Asn Val Thr Val Asp Glu Val Asn Ala Ala Met Lys Ala Ala Ser Asn
1               5                   10                  15

Glu Ser Tyr

<210> SEQ ID NO 40
<211> LENGTH: 13
<212> TYPE: PRT
<213> ORGANISM: Streptococcus pneumoniae

<400> SEQUENCE: 40

Thr Gln Thr Lys Val Leu Asp Val Asp Gly Lys Gln Leu
1               5                   10

<210> SEQ ID NO 41
<211> LENGTH: 19

```
<212> TYPE: PRT
<213> ORGANISM: Streptococcus pneumoniae

<400> SEQUENCE: 41

Met Ser Tyr Thr Ala Gln Leu Val Arg Thr Leu Glu Tyr Phe Ala Lys
1               5                   10                  15

Ile Ala Lys

<210> SEQ ID NO 42
<211> LENGTH: 13
<212> TYPE: PRT
<213> ORGANISM: Klebsiella pneumoniae

<400> SEQUENCE: 42

Leu Arg Arg Leu Leu Glu Val Asp Ser Ser Leu Glu Val
1               5                   10

<210> SEQ ID NO 43
<211> LENGTH: 14
<212> TYPE: PRT
<213> ORGANISM: Klebsiella pneumoniae

<400> SEQUENCE: 43

Asp Leu Thr Ser Pro Lys Val Leu Ala Tyr Leu Leu Lys His
1               5                   10

<210> SEQ ID NO 44
<211> LENGTH: 15
<212> TYPE: PRT
<213> ORGANISM: Klebsiella pneumoniae

<400> SEQUENCE: 44

Pro Phe Pro Trp Ser Val Asp Phe Thr Glu Asp Ala Leu Ile Val
1               5                   10                  15

<210> SEQ ID NO 45
<211> LENGTH: 15
<212> TYPE: PRT
<213> ORGANISM: Klebsiella pneumoniae

<400> SEQUENCE: 45

Thr Val Tyr Ala Glu Lys Glu Ala Gln His Ile Pro Trp Gln Ala
1               5                   10                  15

<210> SEQ ID NO 46
<211> LENGTH: 21
<212> TYPE: PRT
<213> ORGANISM: Klebsiella pneumoniae

<400> SEQUENCE: 46

Ala Gly Glu Met Lys Thr Ile Val Tyr Asn Val Asn Asp Asp Thr Leu
1               5                   10                  15

Thr Pro Asp Asp Thr
                20

<210> SEQ ID NO 47
<211> LENGTH: 17
<212> TYPE: PRT
<213> ORGANISM: Klebsiella pneumoniae

<400> SEQUENCE: 47

Val Ser Val Leu Glu Lys Lys Val Thr Ala Asp Glu Val Asn Gln Ala
1               5                   10                  15
```

Met

<210> SEQ ID NO 48
<211> LENGTH: 14
<212> TYPE: PRT
<213> ORGANISM: Klebsiella pneumoniae

<400> SEQUENCE: 48

Ile Ile Gly Ser His Phe Gly Ser Ile Tyr Asp Ala Thr Gln
1               5                   10

<210> SEQ ID NO 49
<211> LENGTH: 16
<212> TYPE: PRT
<213> ORGANISM: Klebsiella pneumoniae

<400> SEQUENCE: 49

Leu Glu Ile Val Glu Ala Gly Gly Val Gln Leu Val Lys Thr Val Ala
1               5                   10                  15

<210> SEQ ID NO 50
<211> LENGTH: 16
<212> TYPE: PRT
<213> ORGANISM: Klebsiella pneumoniae

<400> SEQUENCE: 50

Tyr Gly Phe Val Thr Gln Leu Ile Arg Val Leu Glu Lys Phe Ala Arg
1               5                   10                  15

<210> SEQ ID NO 51
<211> LENGTH: 15
<212> TYPE: PRT
<213> ORGANISM: Pseudomonas spp

<400> SEQUENCE: 51

Leu Arg Ala Leu Tyr Thr Gly His Tyr Arg Glu Gln Leu Gln Val
1               5                   10                  15

<210> SEQ ID NO 52
<211> LENGTH: 13
<212> TYPE: PRT
<213> ORGANISM: Pseudomonas spp

<400> SEQUENCE: 52

Asp Leu Gly Asp Ala Ala Val Asn Ala His Leu Phe Gln
1               5                   10

<210> SEQ ID NO 53
<211> LENGTH: 22
<212> TYPE: PRT
<213> ORGANISM: Pseudomonas spp

<400> SEQUENCE: 53

Gly Glu Val Glu His Asp Ala Glu Ser Leu Arg Val Met Gly Asp Arg
1               5                   10                  15

Ile Ala Val Ser Ala Ile
            20

<210> SEQ ID NO 54
<211> LENGTH: 18
<212> TYPE: PRT
<213> ORGANISM: Pseudomonas spp

<400> SEQUENCE: 54

```
Ser Ala Ile Arg Asn Pro Ala Glu Leu Pro Trp Lys Ser Leu Gly Val
1               5                   10                  15

Asp Ile

<210> SEQ ID NO 55
<211> LENGTH: 13
<212> TYPE: PRT
<213> ORGANISM: Pseudomonas spp

<400> SEQUENCE: 55

Val Ala Gln Val Leu His Arg Glu Leu Gly Ile Glu His
1               5                   10

<210> SEQ ID NO 56
<211> LENGTH: 18
<212> TYPE: PRT
<213> ORGANISM: Pseudomonas spp

<400> SEQUENCE: 56

Thr Ile His Ala Tyr Thr Asn Asp Gln Asn Leu Ser Asp Val Tyr His
1               5                   10                  15

Pro Asp

<210> SEQ ID NO 57
<211> LENGTH: 20
<212> TYPE: PRT
<213> ORGANISM: Pseudomonas spp

<400> SEQUENCE: 57

Val Tyr His Pro Asp Leu Tyr Arg Ala Arg Ser Ala Thr Gln Ser Met
1               5                   10                  15

Ile Pro Thr Lys
            20

<210> SEQ ID NO 58
<211> LENGTH: 18
<212> TYPE: PRT
<213> ORGANISM: Pseudomonas spp

<400> SEQUENCE: 58

Val Gln Val Ala Arg Asp Thr Ser Val Asp Glu Val Asn Arg Leu Leu
1               5                   10                  15

Arg Glu

<210> SEQ ID NO 59
<211> LENGTH: 15
<212> TYPE: PRT
<213> ORGANISM: Pseudomonas spp

<400> SEQUENCE: 59

Gly Ser Pro Val Leu Gly Tyr Asn Thr Gln Pro Leu Val Ser Val
1               5                   10                  15

<210> SEQ ID NO 60
<211> LENGTH: 15
<212> TYPE: PRT
<213> ORGANISM: Pseudomonas spp

<400> SEQUENCE: 60

Ala Asn His Thr Lys Val Ser Gly Arg Leu Val Lys Ala Met Ala
1               5                   10                  15
```

```
<210> SEQ ID NO 61
<211> LENGTH: 13
<212> TYPE: PRT
<213> ORGANISM: Pseudomonas spp

<400> SEQUENCE: 61

Met Leu Asp Ser Ala Leu Ala Leu Ala Ala Ala Arg Asp
1               5                   10

<210> SEQ ID NO 62
<211> LENGTH: 9
<212> TYPE: PRT
<213> ORGANISM: Pseudomonas spp

<400> SEQUENCE: 62

Thr Gly His Tyr Arg Glu Gln Leu Gln
1               5

<210> SEQ ID NO 63
<211> LENGTH: 13
<212> TYPE: PRT
<213> ORGANISM: Neisseria meningitidis (group B)

<400> SEQUENCE: 63

Ala Leu Arg Gln Ile Glu Lys Ala His Asp Ile Glu Val
1               5                   10

<210> SEQ ID NO 64
<211> LENGTH: 13
<212> TYPE: PRT
<213> ORGANISM: Neisseria meningitidis (group B)

<400> SEQUENCE: 64

Asp Leu Thr Pro Ala Glu Met Leu Leu His Leu Phe Lys
1               5                   10

<210> SEQ ID NO 65
<211> LENGTH: 13
<212> TYPE: PRT
<213> ORGANISM: Neisseria meningitidis (group B)

<400> SEQUENCE: 65

Glu Leu Lys Asp Asp Ala Ile Val Val Asn Gly Lys Glu
1               5                   10

<210> SEQ ID NO 66
<211> LENGTH: 14
<212> TYPE: PRT
<213> ORGANISM: Neisseria meningitidis (group B)

<400> SEQUENCE: 66

His Arg Lys Gly Asp Leu Arg Arg Ala Arg Ala Ala Ala Leu
1               5                   10

<210> SEQ ID NO 67
<211> LENGTH: 13
<212> TYPE: PRT
<213> ORGANISM: Neisseria meningitidis (group B)

<400> SEQUENCE: 67

Asn Ala Ala Met Lys Ala Ala Ala Ser Glu Ser Tyr Gly
1               5                   10

<210> SEQ ID NO 68
<211> LENGTH: 13
```

-continued

```
<212> TYPE: PRT
<213> ORGANISM: Neisseria meningitidis (group B)

<400> SEQUENCE: 68

Thr Gln Thr Arg Val Met Thr Val Gly Gly Lys Gln Leu
1               5                   10

<210> SEQ ID NO 69
<211> LENGTH: 15
<212> TYPE: PRT
<213> ORGANISM: Neisseria meningitidis (group B)

<400> SEQUENCE: 69

Thr Cys Gln Leu Val Arg Thr Leu Glu Tyr Phe Ala Gly Lys Ile
1               5                   10                  15

<210> SEQ ID NO 70
<211> LENGTH: 336
<212> TYPE: PRT
<213> ORGANISM: Streptococcus agalactiae

<400> SEQUENCE: 70

Met Val Val Lys Val Gly Ile Asn Gly Phe Gly Arg Ile Gly Arg Leu
1               5                   10                  15

Ala Phe Arg Arg Ile Gln Asn Val Glu Gly Val Glu Val Thr Arg Ile
                20                  25                  30

Asn Asp Leu Thr Asp Pro Asn Met Leu Ala His Leu Leu Lys Tyr Asp
            35                  40                  45

Thr Thr Gln Gly Arg Phe Asp Gly Thr Val Glu Val Lys Glu Gly Gly
        50                  55                  60

Phe Glu Val Asn Gly Gln Phe Val Lys Val Ser Ala Glu Arg Glu Pro
65                  70                  75                  80

Ala Asn Ile Asp Trp Ala Thr Asp Gly Val Glu Ile Val Leu Glu Ala
                85                  90                  95

Thr Gly Phe Phe Ala Ser Lys Glu Lys Ala Glu Gln His Ile His Glu
                100                 105                 110

Asn Gly Ala Lys Lys Val Val Ile Thr Ala Phe Gly Gly Asn Asp Val
            115                 120                 125

Lys Thr Val Val Phe Asn Thr Asn His Asp Ile Leu Asp Gly Thr Glu
        130                 135                 140

Thr Val Ile Ser Gly Ala Ser Cys Thr Thr Asn Cys Leu Ala Pro Met
145                 150                 155                 160

Ala Lys Ala Leu Gln Asp Asn Phe Gly Val Lys Gln Gly Leu Met Thr
                165                 170                 175

Thr Ile His Ala Tyr Thr Gly Asp Gln Met Ile Leu Asp Gly Pro His
            180                 185                 190

Arg Gly Gly Asp Leu Arg Arg Ala Arg Ala Gly Ala Ala Asn Ile Val
        195                 200                 205

Pro Asn Ser Thr Gly Ala Ala Lys Ala Ile Gly Leu Val Ile Pro Glu
    210                 215                 220

Leu Asn Gly Lys Leu Asp Gly Ala Ala Gln Arg Val Pro Val Pro Thr
225                 230                 235                 240

Gly Ser Val Thr Glu Leu Val Ala Thr Leu Glu Lys Asp Val Thr Val
                245                 250                 255

Glu Glu Val Asn Ala Ala Met Lys Ala Ala Asn Asp Ser Tyr Gly
            260                 265                 270

Tyr Thr Glu Asp Pro Ile Val Ser Ser Asp Ile Val Gly Ile Ser Tyr
```

```
            275                 280                 285
Gly Ser Leu Phe Asp Ala Thr Gln Thr Lys Val Gln Thr Val Asp Gly
    290                 295                 300

Asn Gln Leu Val Lys Val Val Ser Trp Tyr Asp Asn Glu Met Ser Tyr
305                 310                 315                 320

Thr Ser Gln Leu Val Arg Thr Leu Glu Tyr Phe Ala Lys Ile Ala Lys
                325                 330                 335

<210> SEQ ID NO 71
<211> LENGTH: 11
<212> TYPE: PRT
<213> ORGANISM: Streptococcus agalactiae

<400> SEQUENCE: 71

Asp Val Thr Val Glu Glu Val Asn Ala Ala Met
1               5                   10

<210> SEQ ID NO 72
<211> LENGTH: 331
<212> TYPE: PRT
<213> ORGANISM: Escherichia coli

<400> SEQUENCE: 72

Met Thr Ile Lys Val Gly Ile Asn Gly Phe Gly Arg Ile Gly Arg Ile
1               5                   10                  15

Val Phe Arg Ala Ala Gln Lys Arg Ser Asp Ile Glu Ile Val Ala Ile
                20                  25                  30

Asn Asp Leu Leu Asp Ala Asp Tyr Met Ala Tyr Met Leu Lys Tyr Asp
            35                  40                  45

Ser Thr His Gly Arg Phe Asp Gly Thr Val Glu Val Lys Asp Gly His
        50                  55                  60

Leu Ile Val Asn Gly Lys Lys Ile Arg Val Thr Ala Glu Arg Asp Pro
65                  70                  75                  80

Ala Asn Leu Lys Trp Asp Glu Val Gly Val Asp Val Val Ala Glu Ala
                85                  90                  95

Thr Gly Leu Phe Leu Thr Asp Glu Thr Ala Arg Lys His Ile Thr Ala
            100                 105                 110

Gly Ala Lys Lys Val Val Met Thr Gly Pro Ser Lys Asp Asn Thr Pro
        115                 120                 125

Met Phe Val Lys Gly Ala Asn Phe Asp Lys Tyr Ala Gly Gln Asp Ile
130                 135                 140

Val Ser Asn Ala Ser Cys Thr Thr Asn Cys Leu Ala Pro Leu Ala Lys
145                 150                 155                 160

Val Ile Asn Asp Asn Phe Gly Ile Ile Glu Gly Leu Met Thr Thr Val
                165                 170                 175

His Ala Thr Thr Ala Thr Gln Lys Thr Val Asp Gly Pro Ser His Lys
            180                 185                 190

Asp Trp Arg Gly Gly Arg Gly Ala Ser Gln Asn Ile Ile Pro Ser Ser
        195                 200                 205

Thr Gly Ala Ala Lys Ala Val Gly Lys Val Leu Pro Glu Leu Asn Gly
    210                 215                 220

Lys Leu Thr Gly Met Ala Phe Arg Val Pro Thr Pro Asn Val Ser Val
225                 230                 235                 240

Val Asp Leu Thr Val Arg Leu Glu Lys Ala Ala Thr Tyr Glu Gln Ile
                245                 250                 255

Lys Ala Ala Val Lys Ala Ala Ala Glu Gly Glu Met Lys Gly Val Leu
```

```
                    260                 265                 270
Gly Tyr Thr Glu Asp Val Val Ser Thr Asp Phe Asn Gly Glu Val
            275                 280                 285

Cys Thr Ser Val Phe Asp Ala Lys Ala Gly Ile Ala Leu Asn Asp Asn
        290                 295                 300

Phe Val Lys Leu Val Ser Trp Tyr Asp Asn Glu Thr Gly Tyr Ser Asn
305                 310                 315                 320

Lys Val Leu Asp Leu Ile Ala His Ile Ser Lys
                325                 330

<210> SEQ ID NO 73
<211> LENGTH: 13
<212> TYPE: PRT
<213> ORGANISM: Escherichia coli

<400> SEQUENCE: 73

Glu Val Lys Asp Gly His Leu Ile Val Asn Gly Lys Lys
1               5                   10

<210> SEQ ID NO 74
<211> LENGTH: 13
<212> TYPE: PRT
<213> ORGANISM: Artificial Sequence
<220> FEATURE:
<223> OTHER INFORMATION: FIG. 12 Peptide

<400> SEQUENCE: 74

Glu Val Lys Asp Gly His Leu Ile Val Asn Gly Lys Lys
1               5                   10
```